(12) United States Patent
Huang et al.

(10) Patent No.: US 10,961,278 B2
(45) Date of Patent: Mar. 30, 2021

(54) VANCOMYCIN DERIVATIVE, PREPARATION METHOD, PHARMACEUTICAL COMPOSITION AND USE THEREOF

(71) Applicant: SHANGHAI INSTITUTE OF MATERIA MEDICA, CHINESE ACADEMY OF SCIENCES, Shanghai (CN)

(72) Inventors: Wei Huang, Shanghai (CN); Lefu Lan, Shanghai (CN); Lun Xiong, Shanghai (CN); Dongliang Guan, Shanghai (CN); Feifei Chen, Shanghai (CN); Iiyun Yang, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 27 days.

(21) Appl. No.: 16/093,518

(22) PCT Filed: Apr. 26, 2017

(86) PCT No.: PCT/CN2017/081941
§ 371 (c)(1),
(2) Date: Oct. 12, 2018

(87) PCT Pub. No.: WO2017/186110
PCT Pub. Date: Nov. 2, 2017

(65) Prior Publication Data
US 2019/0153036 A1    May 23, 2019

(30) Foreign Application Priority Data
Apr. 29, 2016 (CN) .......................... 201610283830.9

(51) Int. Cl.
| | | |
|---|---|---|
| C07K 9/00 | (2006.01) | |
| A61P 31/04 | (2006.01) | |
| A61K 38/14 | (2006.01) | |
| A61K 38/00 | (2006.01) | |

(52) U.S. Cl.
CPC .............. *C07K 9/008* (2013.01); *A61K 38/14* (2013.01); *A61P 31/04* (2018.01); *A61K 38/00* (2013.01)

(58) Field of Classification Search
None
See application file for complete search history.

(56) References Cited

U.S. PATENT DOCUMENTS

2003/0008812 A1   1/2003  Christensen et al.

FOREIGN PATENT DOCUMENTS

| CN | 1315961 | 10/2001 |
|---|---|---|
| CN | 102307903 | 1/2012 |
| WO | WO 00/39156 | * 7/2000 |
| WO | 01/57071 | 8/2001 |
| WO | 01/98327 | 12/2001 |
| WO | 2006/057303 | 6/2006 |

OTHER PUBLICATIONS

Pena et al. ('The shape of D-glucosamine' Phys. Chem. Chem. Phys. v16 2014 pp. 23244-23250) (Year: 2014).*
Yarlagadda et al. ("Tackling vancomycin-resistant bacteria with 'lipophilic-vancomycin-carbohydrate conjugates'" The Journal of Antibiotics v68 2015 pp. 302-312) (Year: 2015).*
Zhanel et al. ('Oritivancin: mechanism of action' Clinical Infectious Diseases v54(S3) 2012 pp. S214-S219) (Year: 2012).*

(Continued)

*Primary Examiner* — Ronald T Niebauer
(74) *Attorney, Agent, or Firm* — Ping Wang; Morris, Manning & Martin LLP

(57) ABSTRACT

Provided are a class of vancomycin derivatives with a structure as shown in the general formula below and pharmaceutically acceptable salts thereof, a preparation method, a pharmaceutical composition containing the compound thereof, and the use of these compounds in preparing drugs for treating and/or preventing bacterial infection diseases, in particular drugs for treating infection diseases caused by Gram-positive bacteria.

(I)

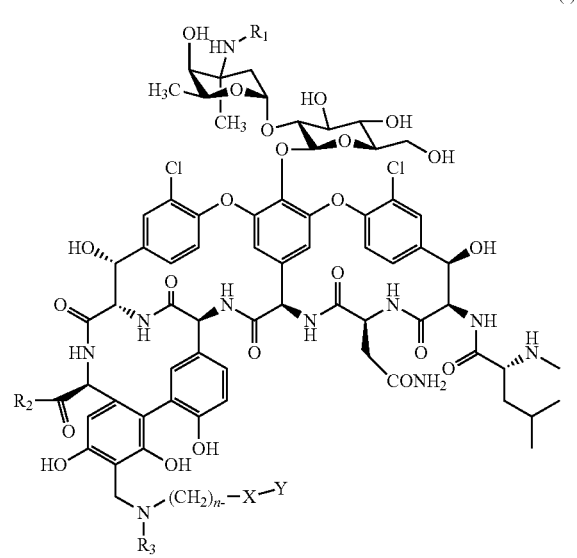

10 Claims, 2 Drawing Sheets

(56) References Cited

OTHER PUBLICATIONS

International Search Report of International Application No. PCT/CN2017/081941 dated Jul. 28, 2017.
Leadbetter, M. R. et al., "Hydrophobic Vancomycin Derivatives with Improved ADME Properties: Discovery of Telavancin (TD-6424)," The Journal of Antibiotics, vol. 57(5), 2004, pp. 326-336.

* cited by examiner

VANCOMYCIN DERIVATIVE, PREPARATION METHOD, PHARMACEUTICAL COMPOSITION AND USE THEREOF

This application is a national stage application of International Patent Application No. PCT/CN2017/081941, filed Apr. 26, 2017, which claims priority to China Patent Application No. 201610283830.9, filed Apr. 29, 2016. The entirety of the aforementioned applications is incorporated herein by reference.

FIELD

The present invention belongs to the field of medicinal chemistry and medical technology, and relates to vancomycin derivatives represented by Formula (I) and pharmaceutically acceptable salts thereof, a method for preparing the same, a pharmaceutical composition comprising the vancomycin derivative or the pharmaceutically acceptable salt thereof, and use thereof in the preparation of a medicament for prevention and treatment of a disease or condition associated with Gram-positive bacterial infection.

BACKGROUND

Antibiotics have achieved great success in the treatment of bacterial infectious diseases in the past half century. However, their widespread use also makes drug-resistant bacterial strains become the common pathogens to cause clinical infections. While traditional infectious diseases have not yet been fully controlled, new infectious diseases and pathogens are still emerging, and the situations caused by multi-resistant microorganisms are becoming more and more serious, which has become a problem in clinical treatment. Therefore, it is very urgent and important to develop a new generation of antibiotics that are effective against drug resistant strains.

Vancomycin and norvancomycin are natural glycopeptide antibiotics extracted from actinomycete fermentation broth. Glycopeptide antibiotics have a heptapeptide core structure, and their mechanism of action is mainly to bind to a dipeptide residue of D-alanyl-D-alanine (Acyl-D-Ala-D-Ala) of bacterial cell wall precursors so as to inhibit the synthesis of peptidoglycan, and thereby prevent maturation of the bacterial cell wall. Since the first clinical use in the 1960s, glycopeptide antibiotics have been used as the last resort against Gram-positive bacteria in the treatment of bacterial infections for the past 50 years. However, since the first reported vancomycin-resistant enterococci (VRE) in clinic in 1986, the vancomycin-resistance of enterococci has become more common (>20%) and spreads to other organisms. Recently, it has been reported abroad that a new methicillin and penicillin-resistant *Staphylococcus* aureus highly resistant to vancomycin (VRSA) was detected in an anti-infective therapy of a hemodialysis patient. Therefore, the importance and urgency to develop a second-generation glycopeptide antibiotic effective against drug-resistant pathogenic strains is self-evident. In the past decades, some important advances have been made in the preparation of synthetic active vancomycin analogs using structural modification strategies. Several compounds obtained by chemical modification of different natural vancomycin analogs have been approved by the US FDA, for example, oritavancin, dalbavancin and telavancin have shown good antibacterial effects against vancomycin-sensitive and resistant bacteria, MRSA (methicillin-resistant *Staphylococcus aureus*), VRSA (vancomycin-resistant *Staphylococcus aureus*) and VRE (vancomycin-resistant enterococci).

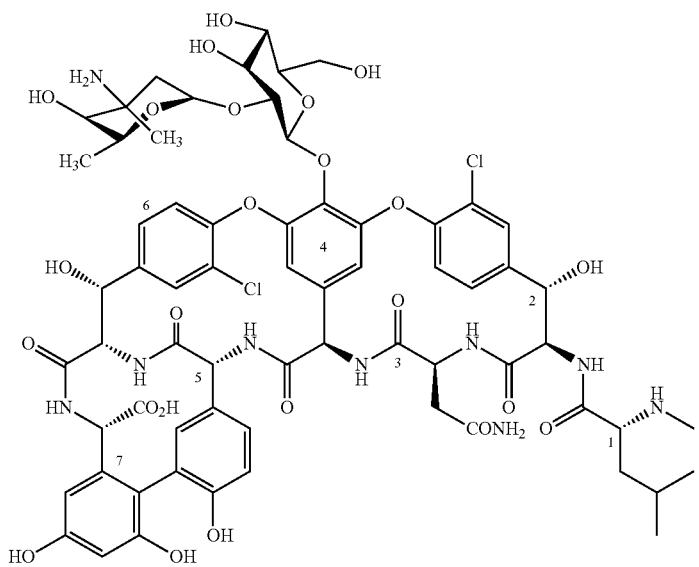

R = H norvancomycin
R = CH3 vancomycin

-continued
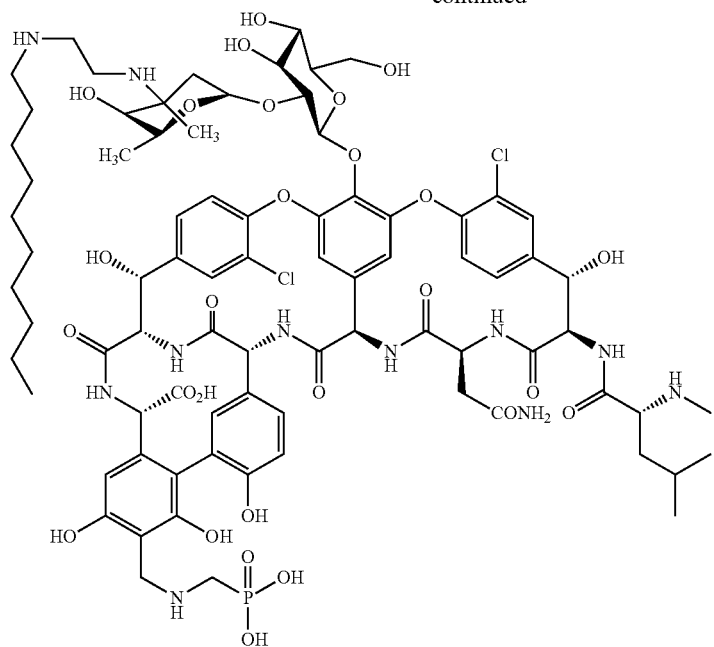
Telavancin
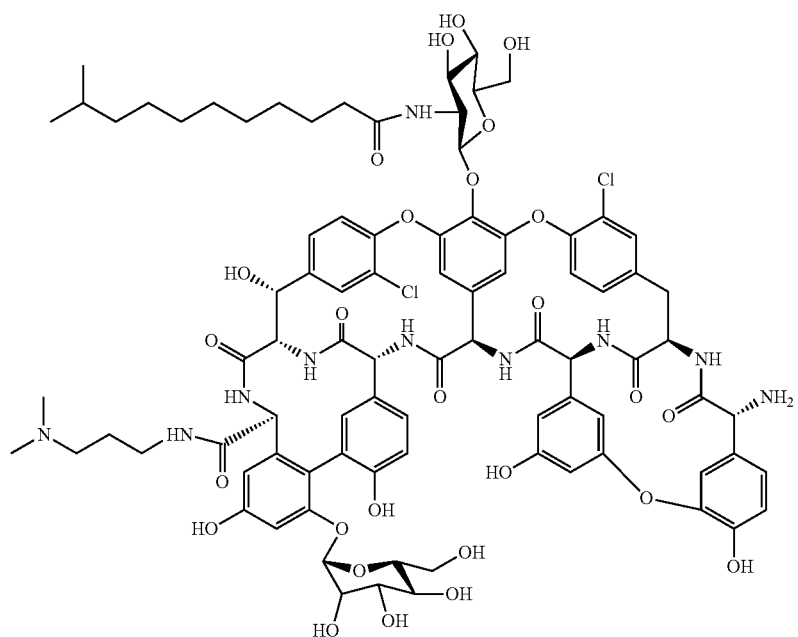
Dalbavancin

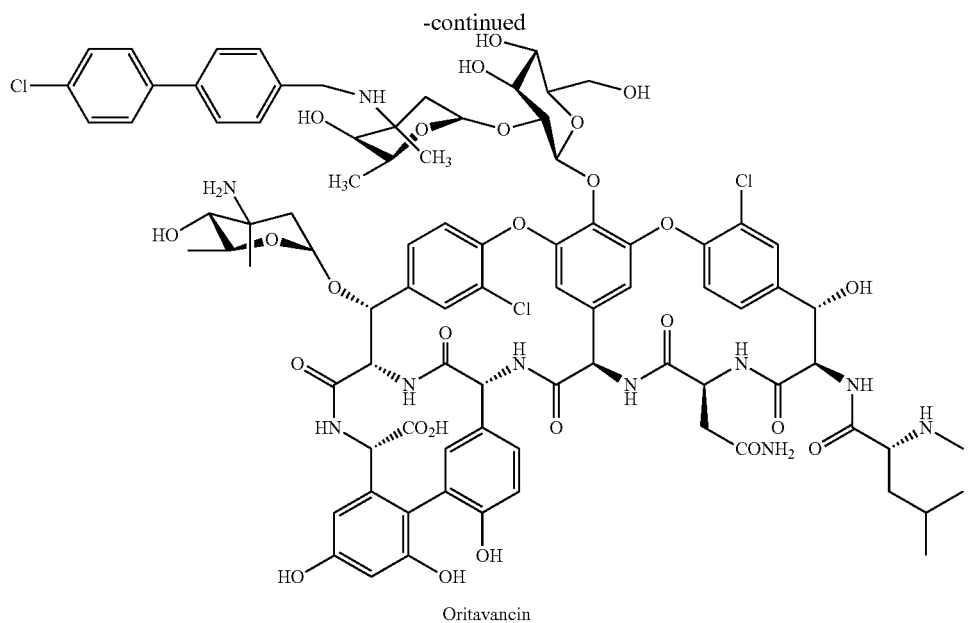
Oritavancin

SUMMARY OF THE INVENTION

One object of the present invention is to provide a vancomycin derivative or pharmaceutically acceptable salt thereof.

Another object of the present invention is to provide a method for preparing the above vancomycin derivative.

Another object of the present invention is to provide a pharmaceutical composition comprising the vancomycin derivative and/or pharmaceutically acceptable salt thereof.

Another object of the present invention is to provide use of the above vancomycin derivative and/or pharmaceutically acceptable salt thereof or the pharmaceutical composition thereof in the preparation of an antibacterial medicament.

The present invention provides a vancomycin derivative represented by the following Formula (I):

The present invention provides a vancomycin derivative represented by the following Formula (I):

(I)

or a pharmaceutically acceptable salt thereof, wherein:
$R_1$ is H, —$CH_2$—$R_4$, —CO—$R_4$ or —$(CH_2)_m$-A-$R_4$, wherein
m is an integer of 1 to 4, preferably 2, 3 or 4,
A is selected from the group consisting of NH—, —O— and S—,
$R_4$ is selected from the group consisting of substituted or unsubstituted $C_8$-$C_{16}$ straight or branched alkyl, substituted or unsubstituted $C_8$-$C_{16}$ straight or branched alkenyl, substituted or unsubstituted $C_8$-$C_{16}$ straight or branched alkynyl, substituted or unsubstituted $C_3$-$C_{10}$ cycloalkyl, substituted or unsubstituted $C_6$-$C_{20}$ aryl, substituted or unsubstituted 3-10 member non-aromatic heterocyclyl comprising one or more heteroatoms selected from the group consisting of N, O and S, substituted or unsubstituted 3-10 membered heteroaryl comprising one or more heteroatoms selected from the group consisting of N, O and S.
wherein, the substituent(s) in the above substituted groups may be one or more selected from the group consisting of halogen, —OH, —$NH_2$, cyano, $C_1$-$C_{10}$ straight or branched alkyl (preferably methyl, ethyl, butyl, pentyl, heptyl), $C_1$-$C_{10}$ straight or branched alkoxy, $C_1$-$C_{10}$ straight or branched alkylamino, $C_1$-$C_{10}$ straight or branched alkylacyl, $C_3$-$C_{10}$ cycloalkyl, halogenated $C_1$-$C_{10}$ straight or branched alkyl (preferably trifluoromethyl), trimethylsilyl $C_2$-$C_{10}$ straight or branched alkynyl (preferably trimethylsilylethynyl), $C_2$-$C_{10}$ straight or branched alkynyl (preferably ethynyl), trifluoromethyl $C_6$-$C_{20}$ aryl (preferably trifluoromethylphenyl), $C_6$-$C_{20}$ aryl substituted by halogen, —OH, —$NH_2$, cyano, $C_1$-$C_{10}$ straight or branched alkyl, $C_1$-$C_{10}$ straight or branched alkoxy, $C_1$-$C_{10}$ straight or branched alkylacyl, $C_2$-$C_6$ straight or branched alkynyl, phenylethynyl, trimethylsilylethynyl, pyridyl, phenyl, cyanophenyl, $C_1$-$C_6$ straight or branched alkylphenyl, trifluoromethylphenyl, chlorophenyl or $C_1$-$C_6$ straight or branched alkyl biphenyl methoxy, $C_3$-$C_{10}$ cycloalkyl substituted by halogen, —OH, —$NH_2$, cyano, $C_1$-$C_{10}$ straight or branched alkyl, $C_1$-$C_{10}$ straight or branched alkoxy, pyridyl, phenyl, $C_1$-$C_6$ straight or branched alkylphenyl, trifluoromethylphenyl or chlorophenyl, $C_1$-$C_{10}$ straight or branched alkylcarbonyl, phenyl $C_1$-$C_{10}$ straight or branched alkylcarbonyl, and the like, in a preferred embodiment of the invention, R₄ is selected from the group consisting of:
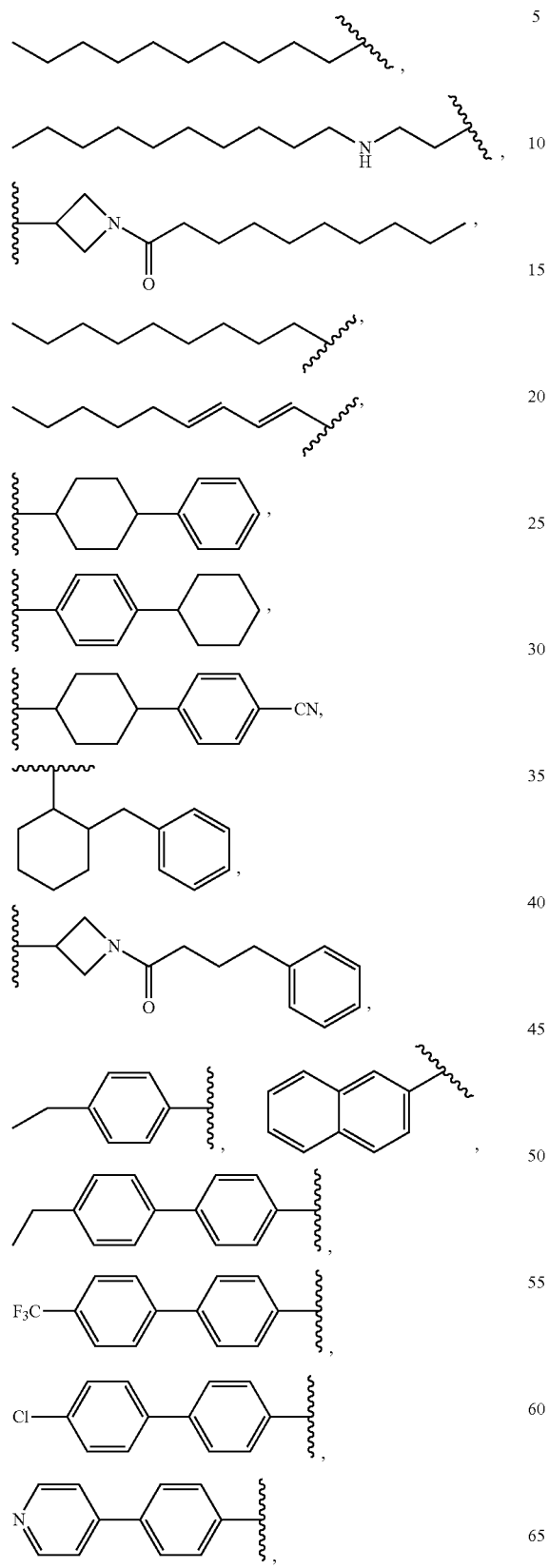
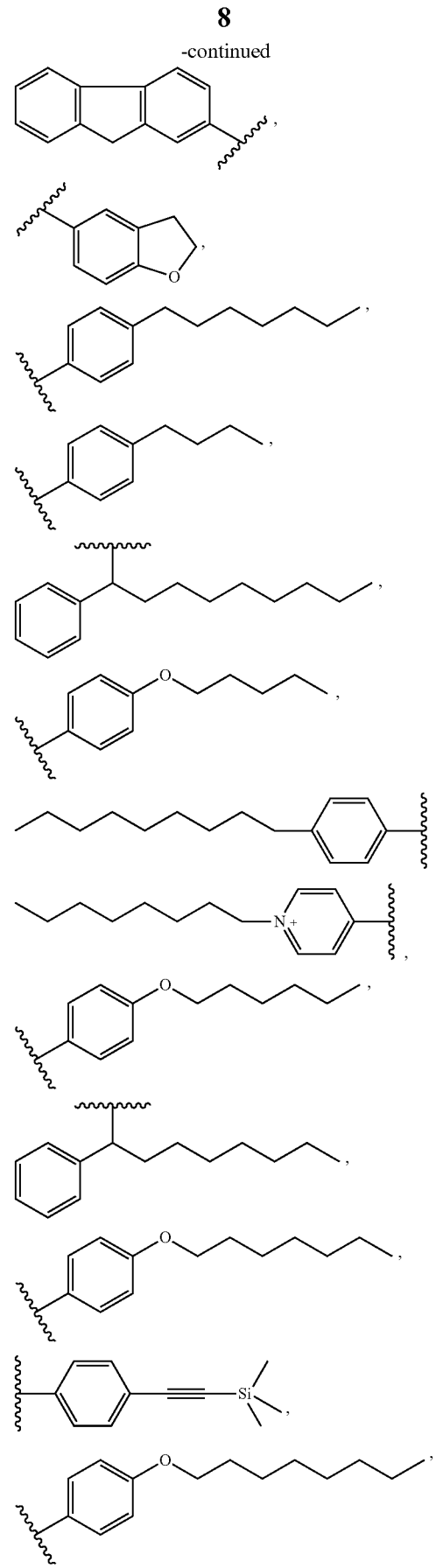

-continued

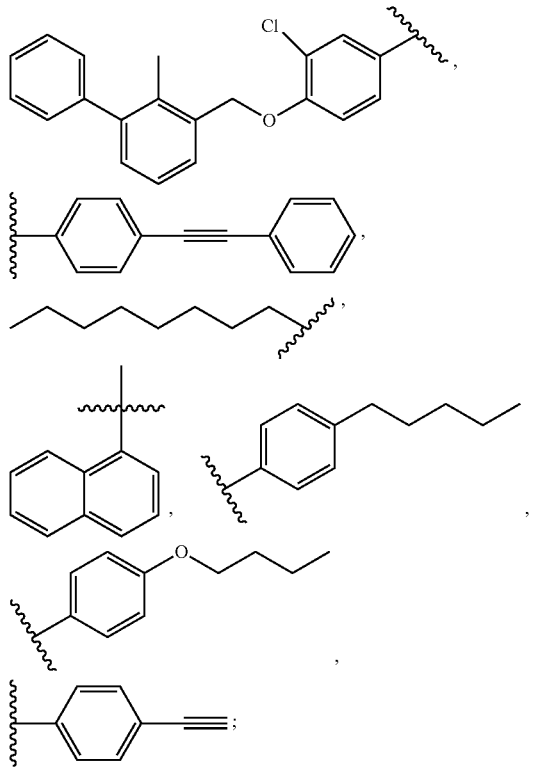

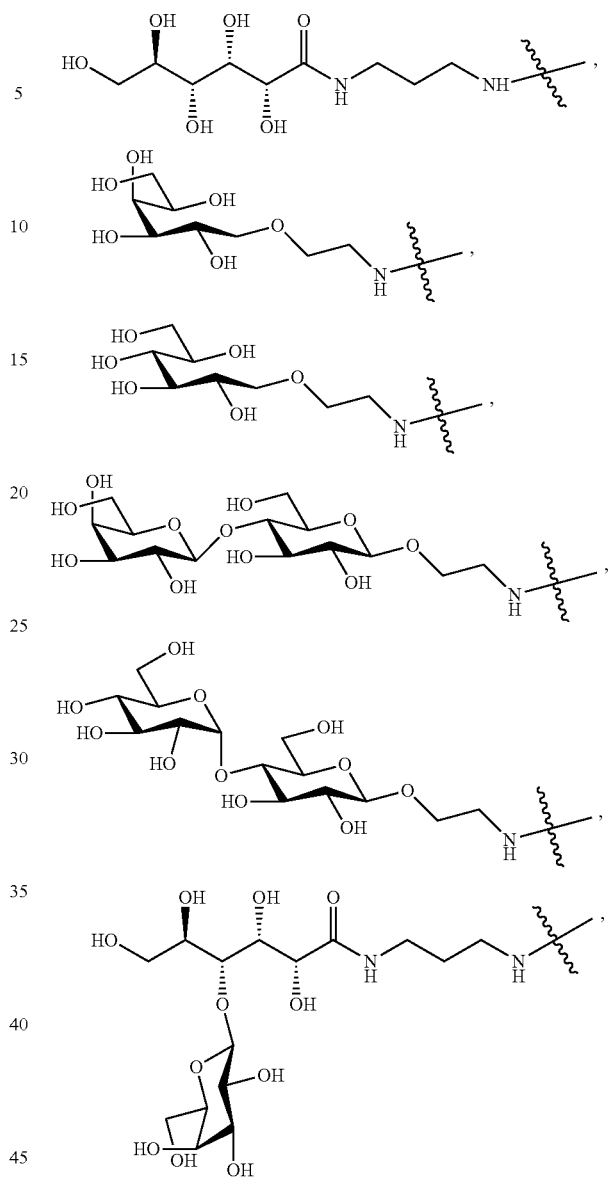

$R_2$ is OH or —NH(CH$_2$)$_p$R$_5$, wherein,
p is an integer between 0 and 6,
$R_5$ is independently selected from the group consisting of a glycosyl group and a substituted amino group; the substituent(s) in the above substituted group may be one or two selected from the group consisting of $C_1$-$C_6$ straight or branched alkyl groups;
preferred $R_2$ is selected from the group consisting of:

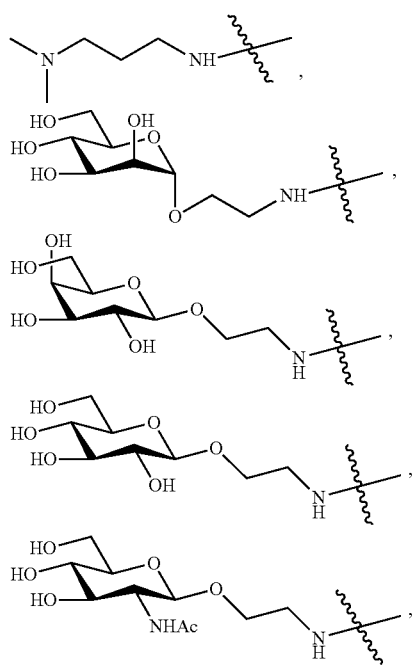

further preferably, $R_2$ is selected from the group consisting of:

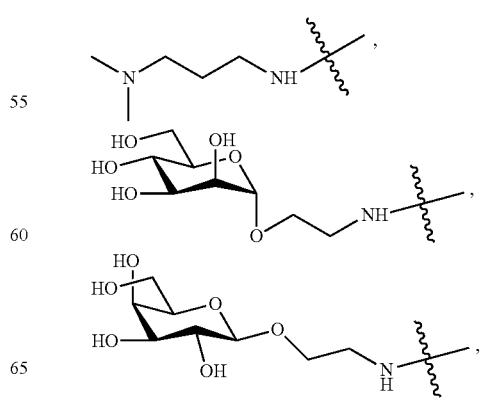

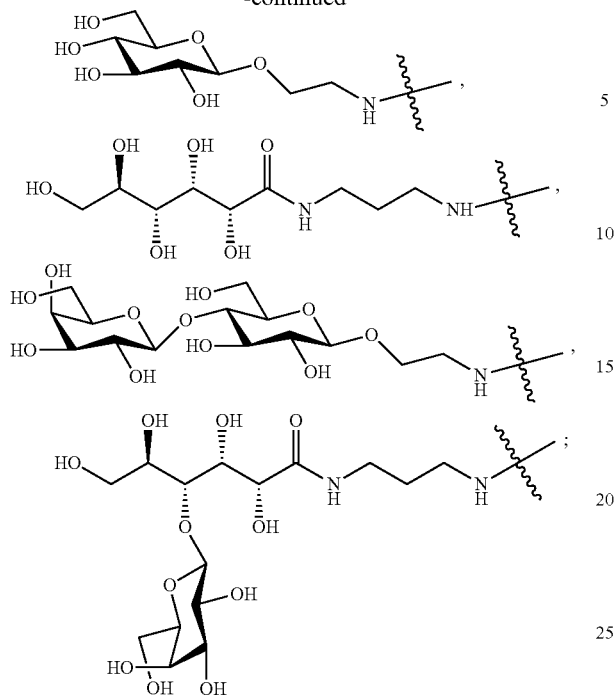

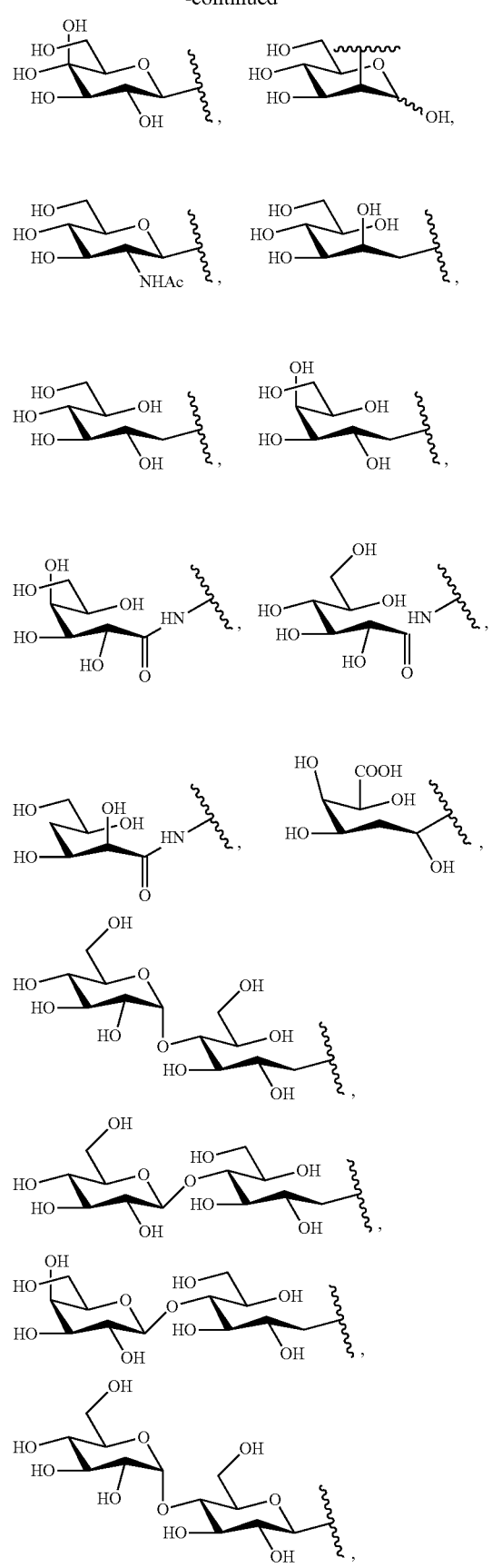

R$_3$ is hydrogen;

n is 2 or 3;

X is —O—, —NH—, —C(O)NH—, —NHC(O)— or —(CH$_2$)$_q$—, wherein q is an integer between 0 and 2; preferably, X is O—, NH—, —C(O)NH— or —(CH$_2$)$_2$—;

Y is a glycosyl.

The above glycosyl is a structural moiety derived from a monosaccharide and/or a disaccharide having carbohydrate characteristics, which is a residue obtained by a glycosidation reaction of the monosaccharide and/or disaccharide. The above glycosidation reaction includes O-glycosylation, N-glycosylation and C-glycosylation reaction of a cyclic or acyclic glycosyl group. In one embodiment of the invention, the glycosyl is selected from the group consisting of glycosyls derived from cyclic monosaccharide, cyclic disaccharide, acyclic monosaccharide, or acyclic disaccharide. In another embodiment of the invention, the glycosyl is selected from the group consisting of glycosyls derived from deoxymonosaccharide, carboxyl monosaccharide, oxidized monosaccharide, and reduced monosaccharide. More particularly, the glycosyl may be preferably selected from the group consisting of glycosyls derived from xylose, mannose, N-acetylglucosamine, galactose, sorbose, arabinose, glucose, fructose, rhamnose, fucose, sialic acid, ribose, deoxyribose, allose, ring-opening structures of above monosaccharides, and disaccharides formed by a combination of above monosaccharides and/or the ring-opening structures of above monosaccharides.

Further preferably, the glycosyl is selected from the group consisting of:

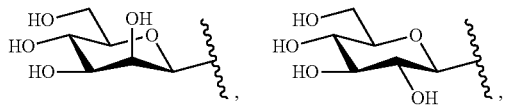

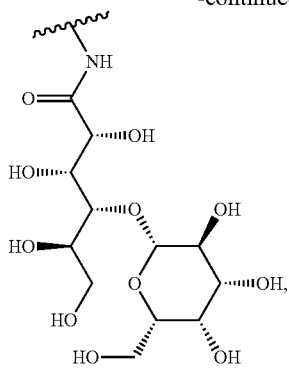

As used herein, the term "acyclic monosaccharide" refers to a monosaccharide in which the aldehyde group at the 1-position of the pyranose is reductively hydrogenated, reductively aminated or amidated. The acyclic monosaccharide is preferably a galactose in which the aldehyde group at the 1-position is reductively aminated or amidated, a glucose in which the aldehyde group at the 1-position is amidated, or a mannose in which the aldehyde group at the 1-position is amidated.

As used herein, the term "acyclic disaccharide" refers to a disaccharide in which the aldehyde group at the 1-position of one or two pyranoses is reductively hydrogenated, reductively aminated or amidated. The said acyclic disaccharide is preferably a lactose in which the aldehyde group at the 1-position is reductively aminated or amidated, a maltose in which the aldehyde group at the 1-position is reductively aminated or amidated, or a cellobiose in which the aldehyde group at the 1-position is reductively aminated or amidated.

As used herein, the term "aryl" means an aromatic ring group containing no hetero atom, preferably, it is an aryl having 6 to 18 carbon atoms, and more preferably is phenyl, naphthyl or biphenyl. Examples of substituted aryl include, but not limited to, 4-methylphenyl, 4-methoxyphenyl, 4-pentylphenyl, 4-butylphenyl, 4-ethynylphenyl, 4-trifluoromethylphenyl, 4-butoxyphenyl, 4-trimethylsilylethynylphenyl, 4-fluorophenyl, 4-(4-trifluoromethylphenyl)phenyl or 4-(4-chlorophenyl)phenyl.

As used herein, the term "$C_8$-$C_{16}$ straight or branched alkyl" refers to a straight or branched alkyl group having 8 to 16 carbon atoms in the main chain. The term "$C_1$-$C_{10}$ straight or branched alkyl" and "$C_1$-$C_6$ straight or branched alkyl" can be construed analogously.

As used herein, the term "$C_1$-$C_{10}$ straight or branched alkoxy" refers to a straight or branched alkoxy group having 1 to 10 carbon atoms in the main chain.

As used herein, the term "$C_1$-$C_{10}$ straight or branched alkylamino" refers to an amino group substituted by straight or branched alkyl having 1 to 10 carbon atoms in the main chain.

As used herein, the term "$C_1$-$C_{10}$ straight or branched alkylacyl" refers to a carbonyl substituted by straight or branched alkyl having 1 to 10 carbon atoms in the main chain. The term "C1-C10 straight or branched alkylcarbonyl" has the same meaning.

As used herein, the term "$C_2$-$C_6$ straight or branched alkynyl" refers to a straight or branched alkynyl having 2 to 6 carbon atoms in the main chain.

As used herein, the term "pharmaceutically acceptable salt" refers to a salt formed with an inorganic acid, such as phosphoric acid, sulfuric acid or hydrochloric acid, an organic acid, such as acetic acid, tartaric acid, citric acid or malic acid, or an acidic amino acid such as aspartic acid or glutamic acid; or a salt formed with an inorganic base after forming an ester or amide with said acids, such as sodium salt, potassium salt, calcium salt, aluminum salt and ammonium salt.

In a preferred embodiment of the invention, the compound of Formula I is a vancomycin derivative represented by the following Formula I-A:

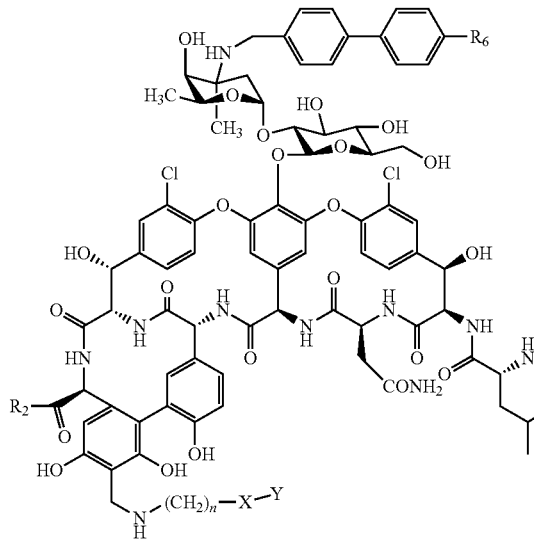

I-A wherein, $R_6$ is selected from the group consisting of chlorine and trifluoromethyl, $R_2$ is selected from the group consisting of OH and the following groups:

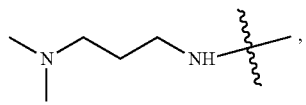

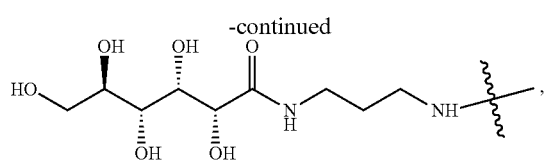
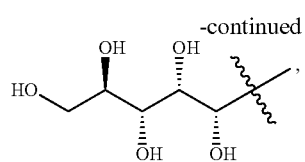
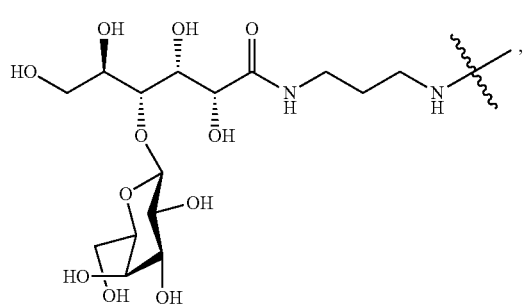
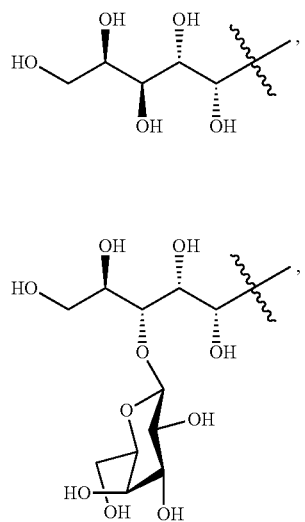
Y is as defined in Formula (I), and is preferably selected from the group consisting of:
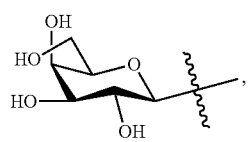
X and n are as defined in Formula (I).
In another preferred embodiment of the invention, the vancomycin derivative is preferably selected from the group consisting of:
| No. | Structure |
|---|---|
| Van001 | 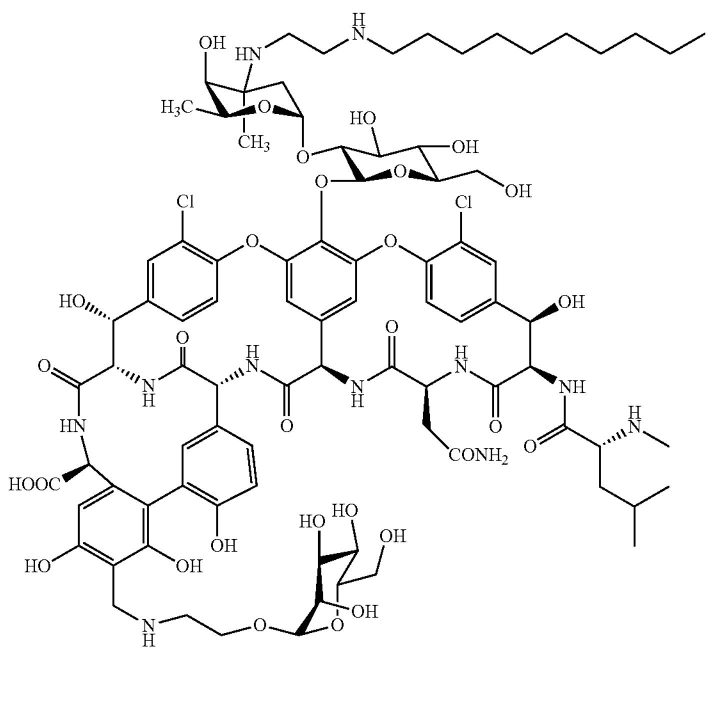 |

-continued
| No. | Structure |
|---|---|
| Van002 | 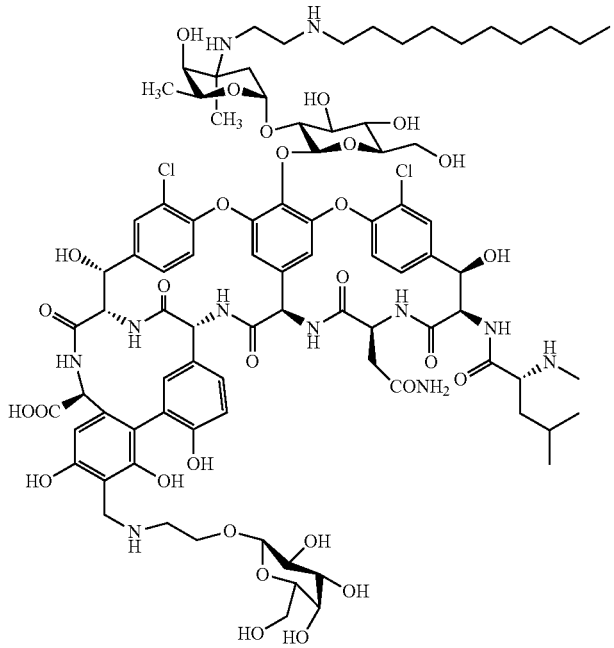 |
| Van003 | 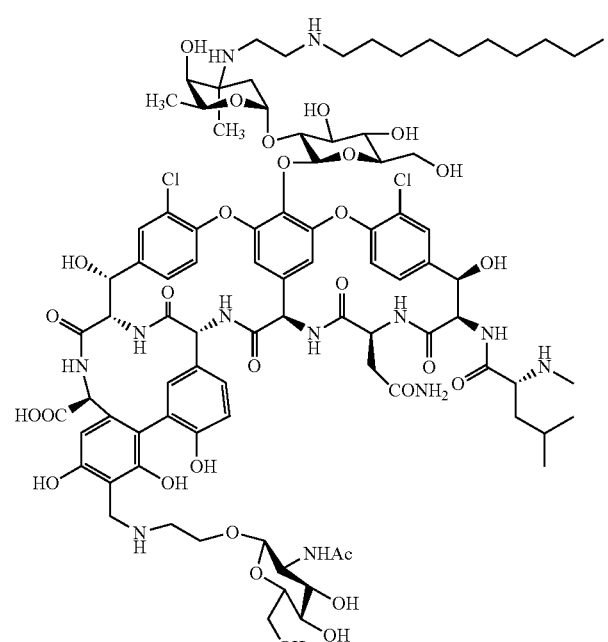 |

| No. | Structure |
|---|---|
| Van004 | *(chemical structure)* |
| Van009 | *(chemical structure)* |

| No. | Structure |
|---|---|
| Van010 | 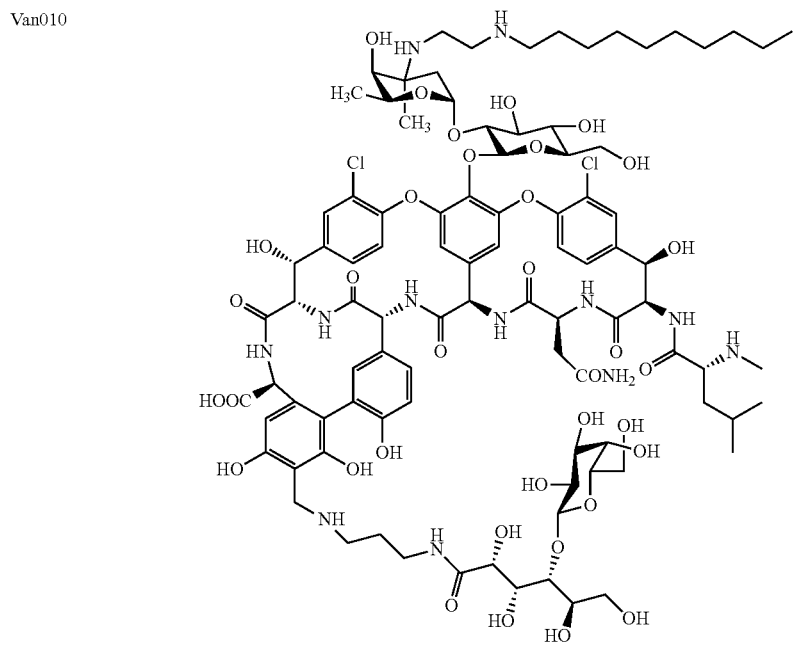 |
| Van011 | 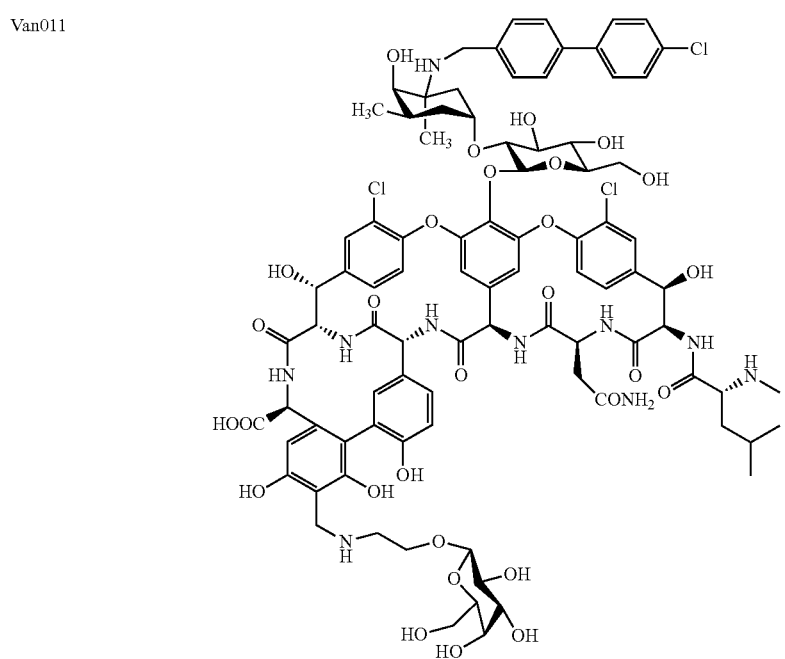 |

| No. | Structure |
|---|---|
| Van013 | 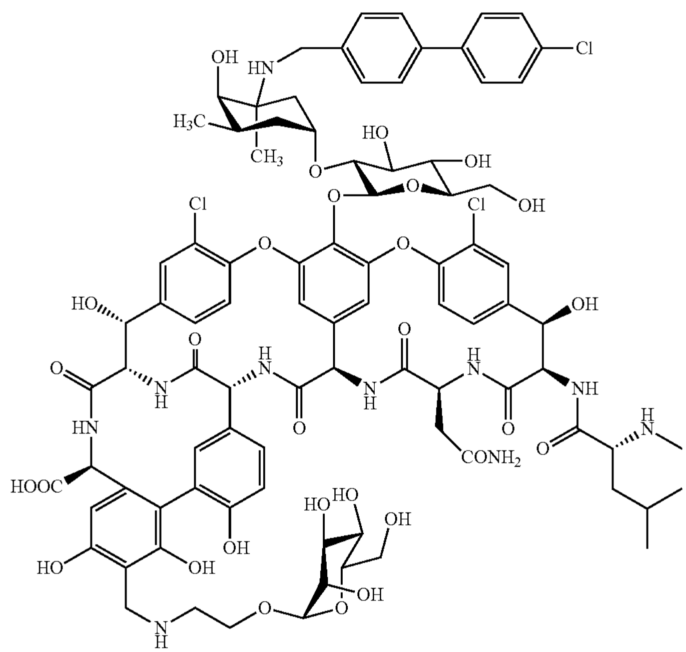 |
| Van014 | 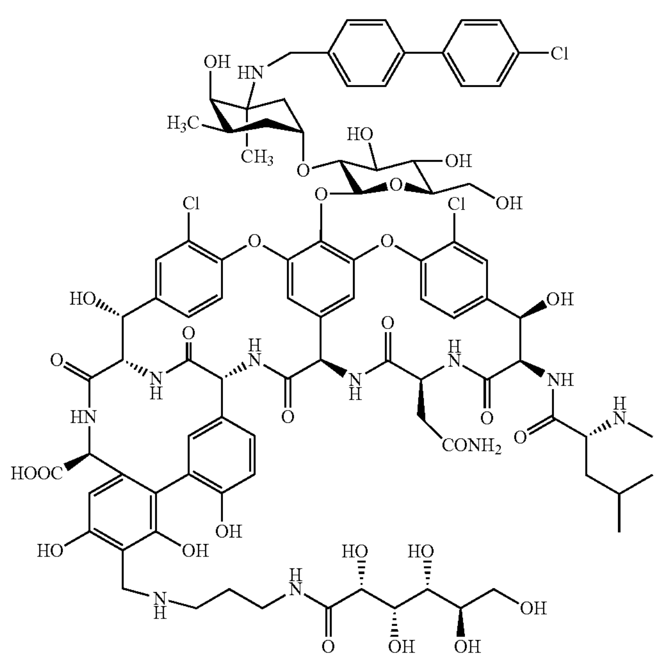 |

| No. | Structure |
|---|---|
| Van015 | 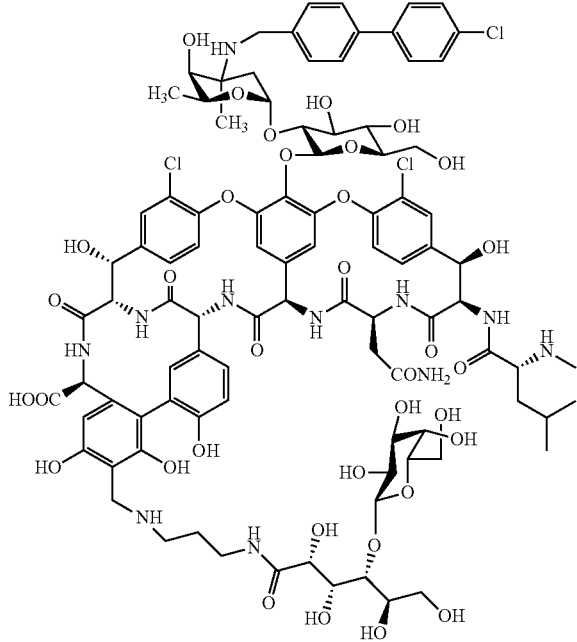 |
| Van016 | 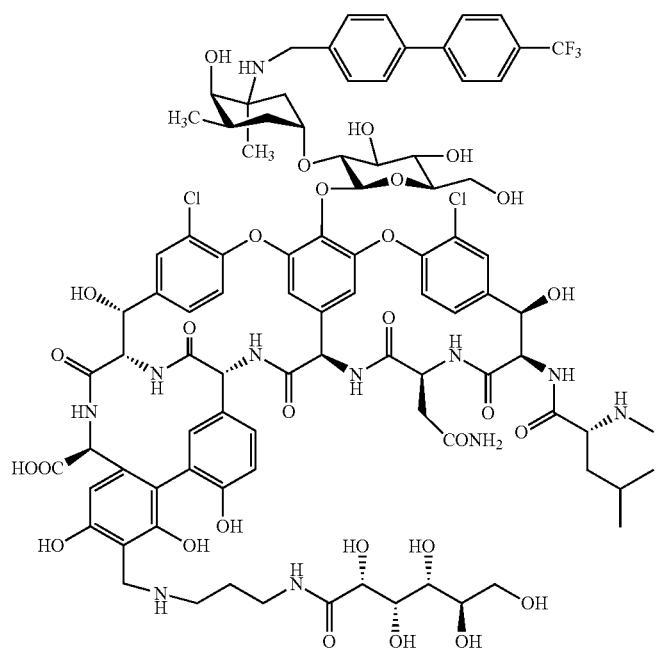 |

| No. | Structure |
|---|---|
| Van017 | (chemical structure) |
| Van018 | (chemical structure) |

| No. | Structure |
|---|---|
| Van019 | 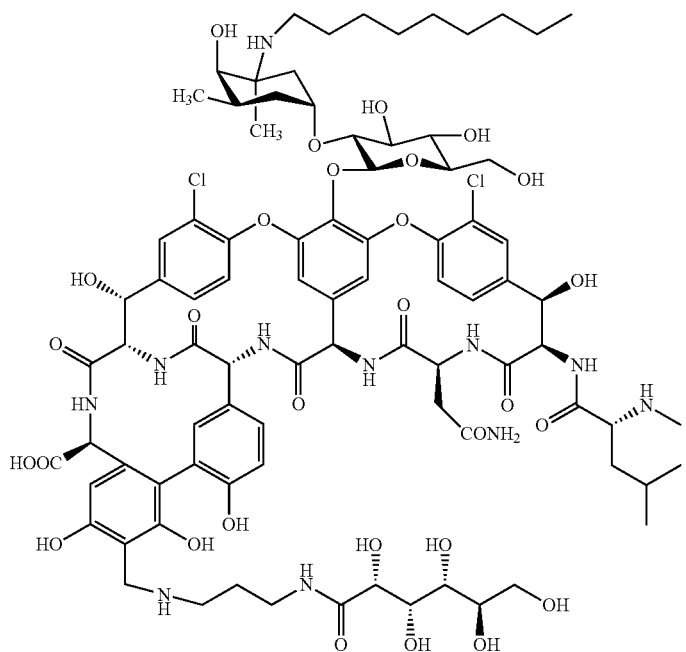 |
| Van021 | 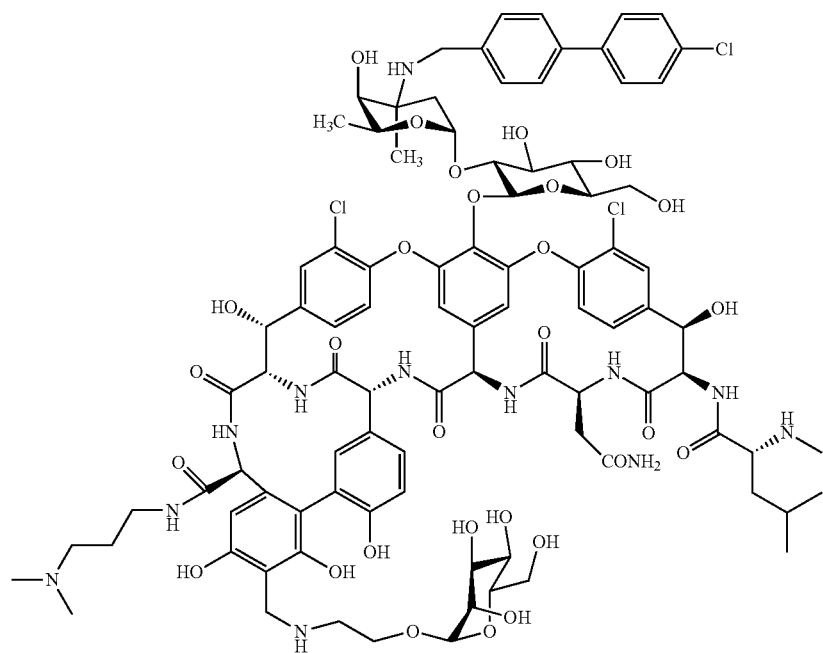 |

| No. | Structure |
|---|---|
| Van022 | (chemical structure) |
| Van024 | (chemical structure) |

| No. | Structure |
|---|---|
| Van025 | *(chemical structure)* |
| Van026 | *(chemical structure)* |

| No. | Structure |
|---|---|
| Van027 | 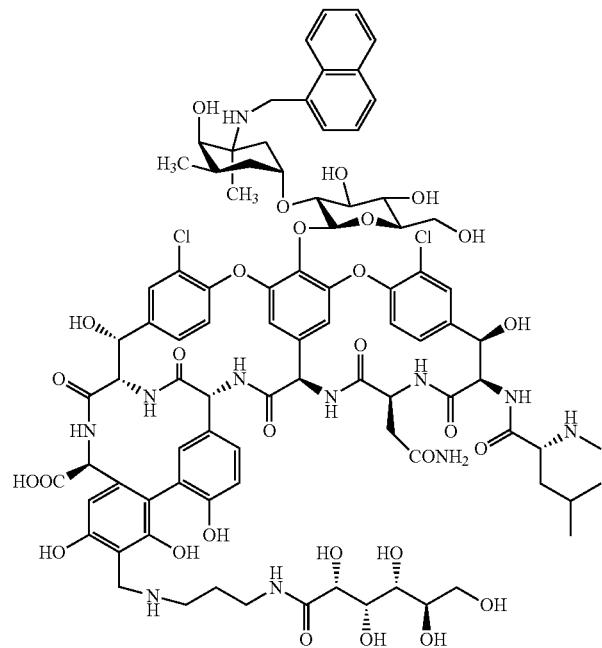 |
| Van028 | 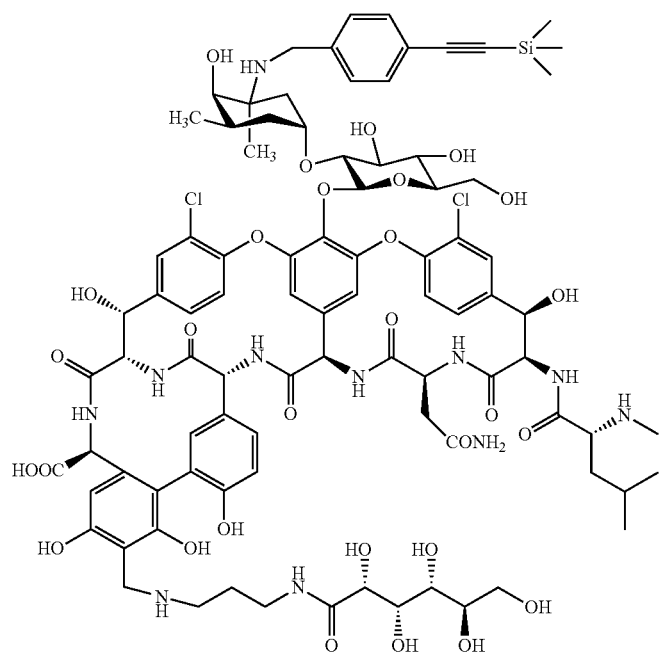 |

| No. | Structure |
|---|---|
| Van029 | 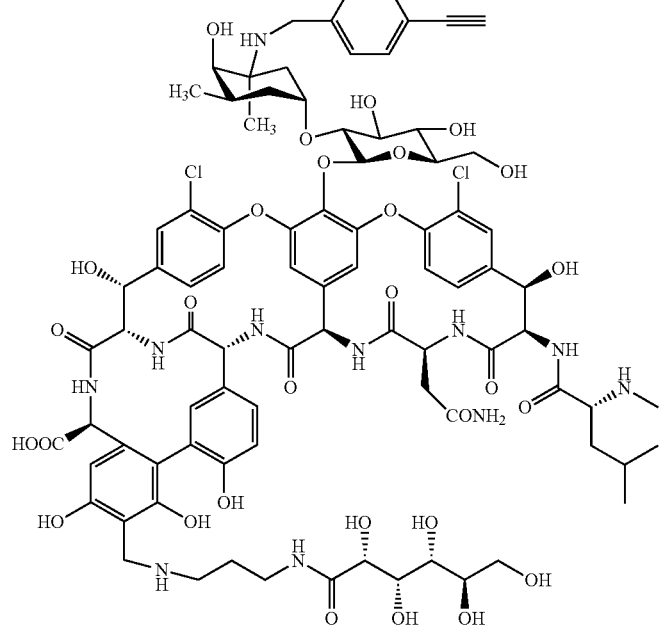 |
| Van030 | 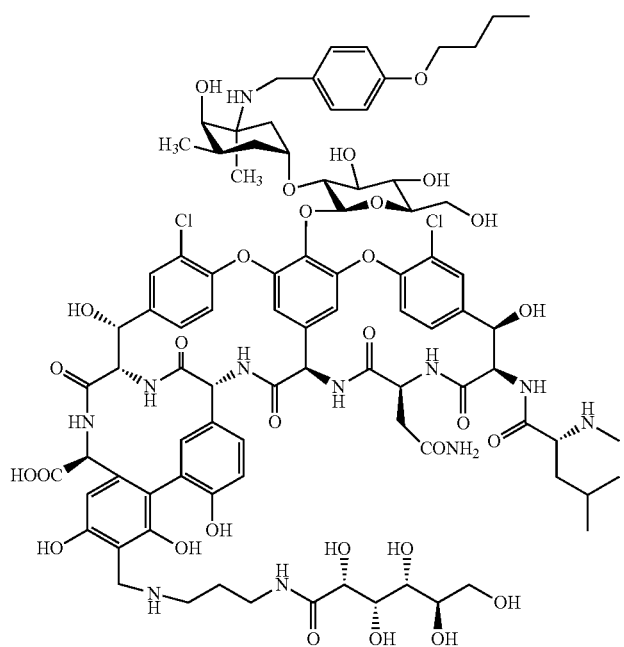 |

-continued
| No. | Structure |
|---|---|
| Van031 | 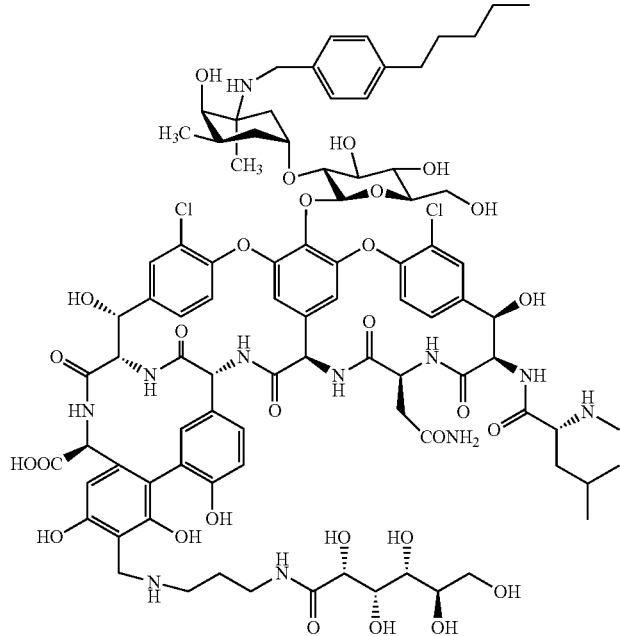 |
| Van037 | 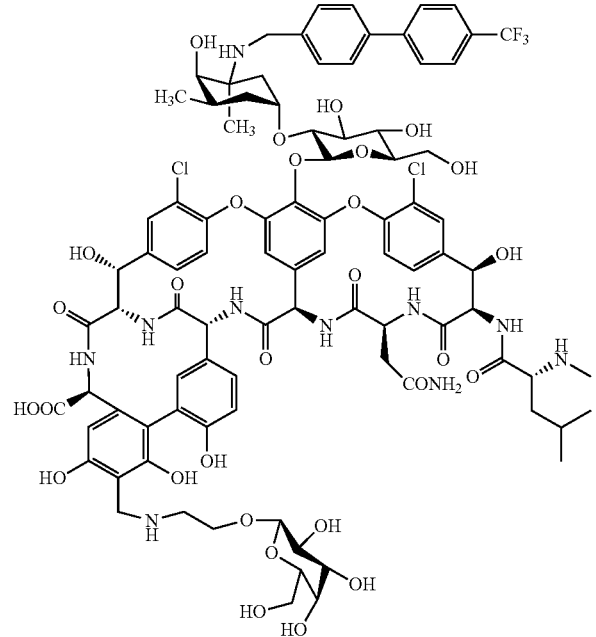 |

| No. | Structure |
|---|---|
| Van039 | 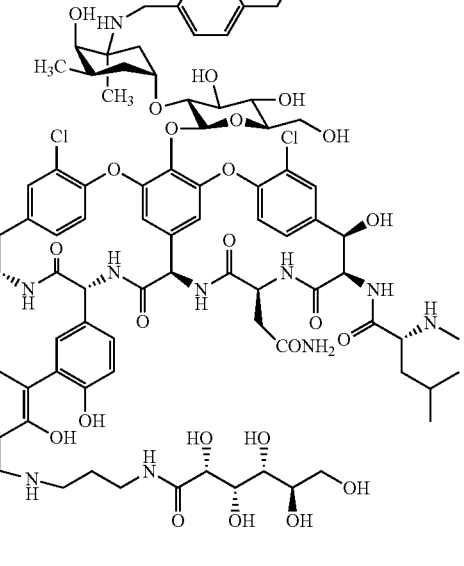 |
| Van040 | 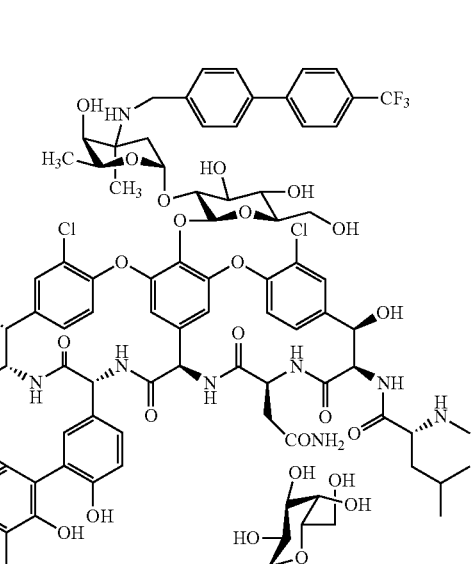 |

| No. | Structure |
|---|---|
| Van041 | (chemical structure) |

The vancomycin derivative is further preferably selected from the group consisting of:

| No. | Structure |
|---|---|
| Van011 | (chemical structure) |

| No. | Structure |
|---|---|
| Van014 | 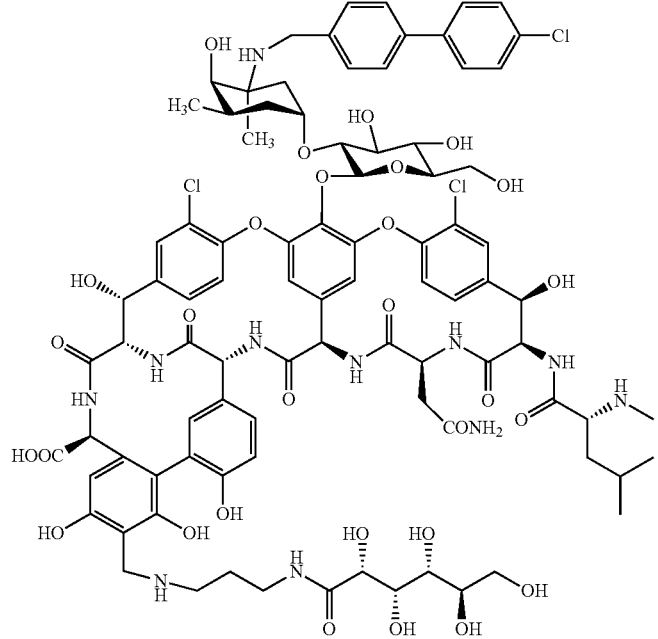 |
| Van016 | 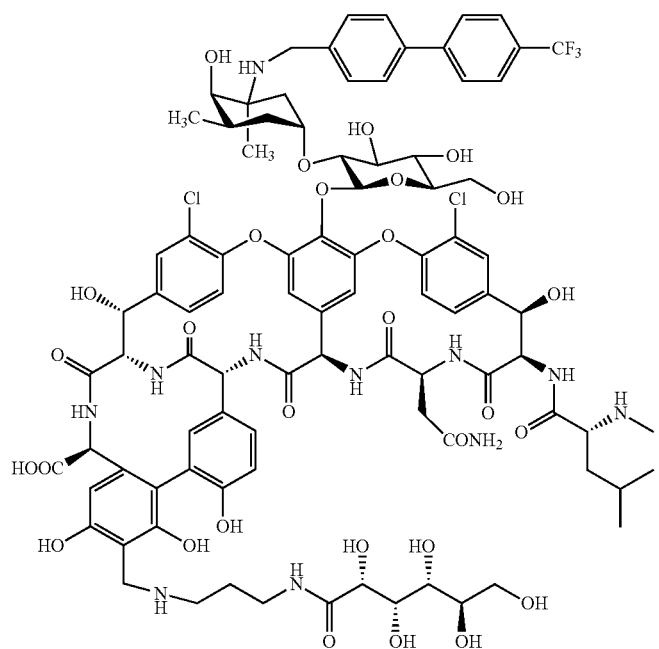 |

| No. | Structure |
|---|---|
| Van017 | 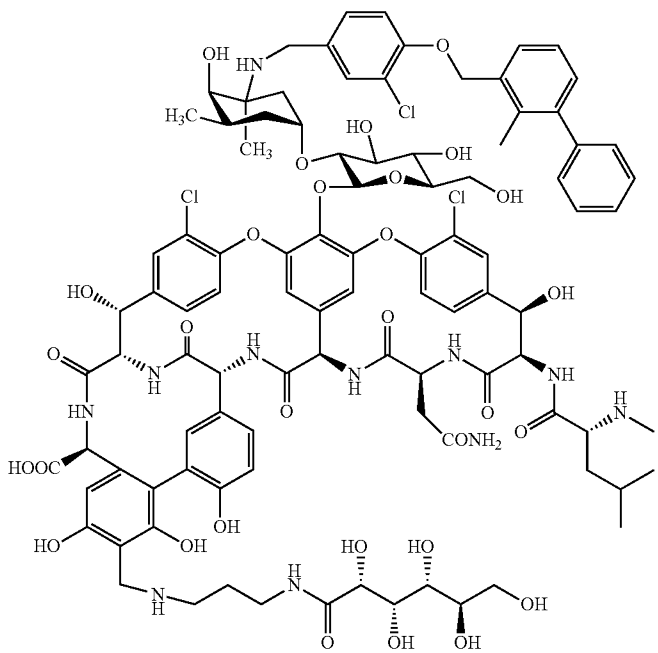 |
| Van022 | 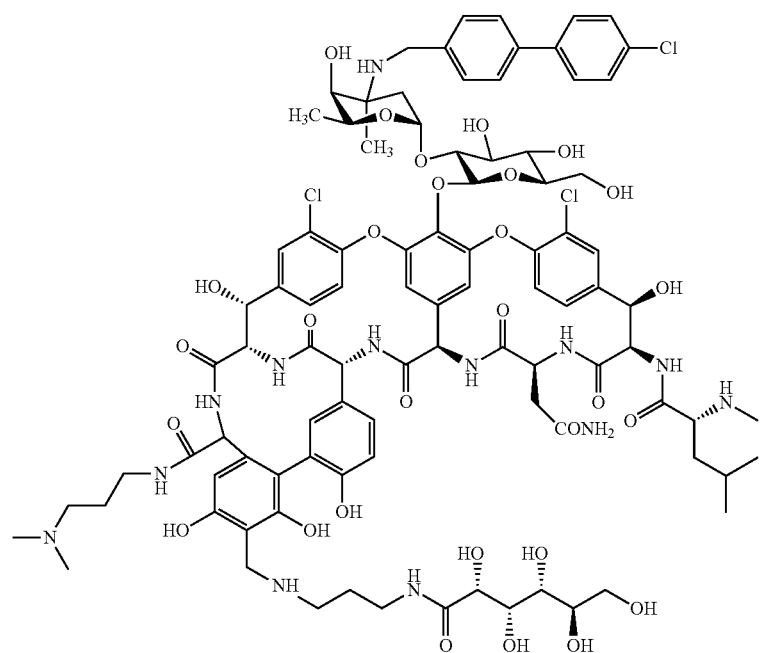 |

| No. | Structure |
|---|---|
| Van037 | (chemical structure) |
| Van039 | (chemical structure) |

| No. | Structure |
|---|---|
| Van040 | 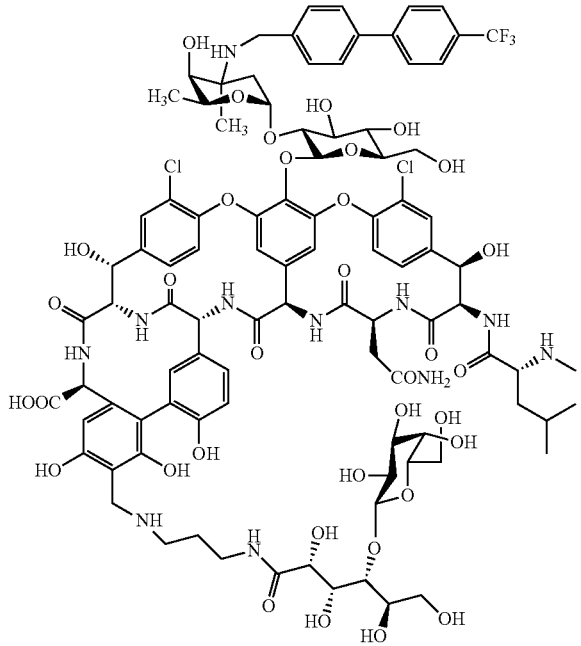 |
| Van041 | 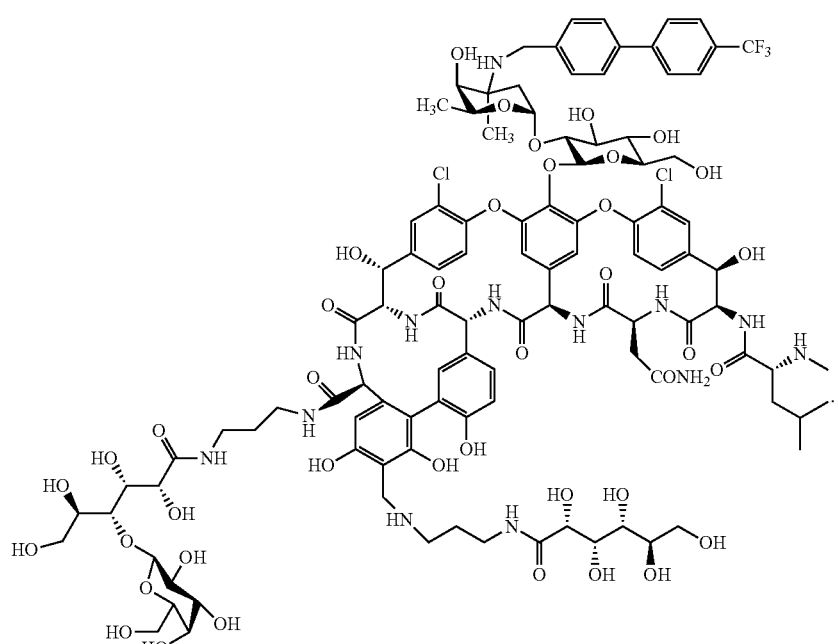 |

The vancomycin derivative represented by Formula (I) may be prepared by a method comprising one or more of the following steps:

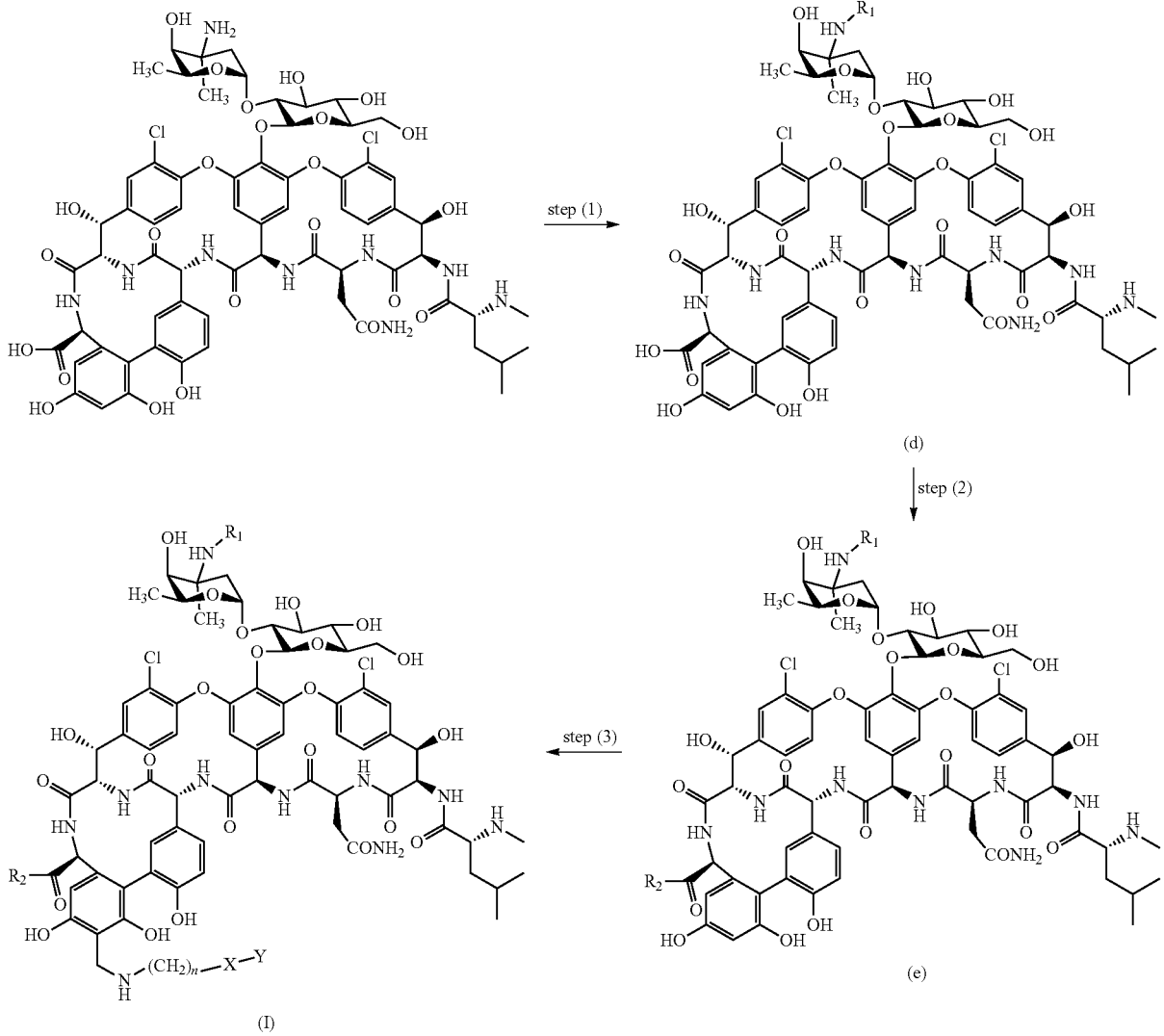

performing a substitution reaction between vancomycin and an acyl or sulfonyl chloride ($R_1Cl$), or a condensation reaction between vancomycin and an aldehyde ($R_4CHO$) to obtain a compound of Formula d;

performing a condensation reaction between the compound of Formula d and an amino compound ($R_2NH_2$) to give a compound of Formula e;

performing a Mannich reaction between the compound of Formula e and a substituted amine in the presence of formaldehyde to give a compound of Formula (I);

wherein $R_1$, $R_2$, $R_3$, $R_4$, n, X and Y are as defined in Formula (I), but $R_1$ is not H and $R_2$ is not OH.

In the step (1), the reaction may be carried out with an aldehyde or an acyl chloride, optionally in the presence or absence of a base without solvent or in a solvent. The solvent used in the reaction may be any solvent, so long as it per se is inert in the reaction and does not inhibit the reaction. Such solvents include halogenated hydrocarbon solvents, such as dichloromethane, 1,2-dichloroethane and chloroform; aromatic hydrocarbon solvents, such as benzene and toluene; aprotic solvents, such as acetone, acetonitrile, N,N-dimethylformamide, N-methyl-2-pyrrolidone, dimethyl sulfoxide and hexamethylphosphoramide; ester solvents, such as ethyl acetate and methyl acetate; ether solvents, such as tetrahydrofuran diethylether and 1,4-dioxane; organic base solvents, such as pyridine, picoline, lutidine and crididine; protic solvents, such as water and methanol, or mixtures of these solvents.

Examples of the base used in this step include organic bases, such as triethylamine, pyridine, N,N-diisopropylethylamine, 4-dimethylaminopyridine, 1,8-diazabicyclo[5.4.0]undec-7-ene and 1,2,2,6,6-pentamethylpiperidine; and inorganic bases, such as sodium carbonate, potassium carbonate, sodium bicarbonate and potassium bicarbonate.

The reaction can be carried out at a temperature of 0° C. to 120° C., preferably 0° C. to 120° C.

In the step (2), a compound of Formula (e) is obtained by reacting a compound of Formula (d) with $NH_2(CH_2)_mR_7$ in DMF in the presence of a condensing agent, referring to the methods as described in the literatures (M. R. Leadbetter et al., *The Journal of Antibiotics*, 2004, 57(5), 326-336 and M.

N. Prebrazhenskaya et al., *The Journal of Antibiotics*, 2007, 60(4), 235-244). The condensing agent may be selected from the group consisting of HATU, HBTU, DMAP, HOBt.

In the step (3), a compound of Formula (f) is obtained by a Mannich reaction of a compound of Formula (e) with a substituted amine and formaldehyde under basic condition, referring to the methods as described in the literatures (P. A. Pavlov et al., *The Journal of Antibiotics*, 1997, 50(6), 509-513, and M. R. Leadbetter et al, *The Journal of Antibiotics*, 2004, 57(5), 326-336).

It will be appreciated that in any of the above routes, the precise order of the synthetic steps by which the various groups and moieties are introduced into the molecule may be varied. A person skilled in the art may ensure that groups or moieties introduced at one stage of the process will not be affected by subsequent transformations and reactions, and select an order of the synthetic steps accordingly.

In a preferred embodiment of the present invention, the vancomycin derivative according to the present invention is capable of binding to the D-alanyl-D alanine dipeptide residue of the cell wall precursors of the bacteria, so as to inhibit the synthesis of cell wall, and thus may be used in preparing an antibacterial medicament of cell wall synthesis inhibitors.

The said vancomycin derivative and pharmaceutically acceptable salts thereof in the present invention have antibacterial activities and can be used in preparing a medicament for treating and/or preventing an infectious disease caused by bacteria, especially by Gram-positive bacteria. Examples of the Gram-positive bacteria include *Staphylococcus, streptococcus, enterococcus, pneumococcus, Bacillus, Bacillus anthracis, Bacillus diphtheriae, tetanus, Clostridium difficile, Listeria monocytogenes*.

According to another aspect of the present invention, provided is a pharmaceutical composition comprising a therapeutically effective amount of one or more selected from the group consisting of the vancomycin derivatives and pharmaceutically acceptable salts thereof as an active ingredient. The composition may further comprise a pharmaceutically acceptable carrier, excipient, adjuvant, accessory, and/or diluent, and the like.

The vancomycin derivative and pharmaceutically acceptable salts thereof in the present invention may be administered alone or in combination with other pharmaceutically acceptable therapeutic agents, particularly with other drugs for treatment and/or prevention of bacterial infection diseases. The pharmaceutically acceptable therapeutic agents include, but are not limited to, other acceptable therapeutic agents in combination with vancomycin, for example, penicillin G, procaine penicillin and penicillin V, macrolides, erythromycin, midecamycin, acetylspiramycin, sineptina and clarithromycin, azithromycin, trimethoprim, dapsone, sulfamethoxazole, gatifloxacin, linezolid, amoxicillin, daptomycin, meropenem, imipenem/cilastatin, piperacillin and sulbactam, cefoperazone and sulbactam sodium, fusidic acid, biapenem, etimicin, ornidazole, metronidazole, etc. The ingredients to be combined may be administered simultaneously or sequentially, in a single formulation or as separate formulations. The combination includes not only the combination of a vancomycin derivative and/or a pharmaceutically acceptable salt thereof in the present invention and one other active agent, but also the combination of a vancomycin derivative and/or a pharmaceutically acceptable salt in the present invention and two or more other active agents.

Accordingly, in still another aspect of the present invention, provided is a pharmaceutical composition comprising a therapeutically effective amount of one or more selected from the group consisting of the vancomycin derivatives and pharmaceutically acceptable salts thereof of the present invention as an active ingredient and other pharmaceutically acceptable therapeutic agents, especially other drugs for treating and/or preventing bacterial infectious diseases. The pharmaceutical composition optionally may further comprise a pharmaceutically acceptable carrier, excipient, adjuvant, accessory, and/or diluent, and the like.

The pharmaceutical composition of the present invention comprising a therapeutically effective amount of one or more selected from the group consisting of the vancomycin derivatives and pharmaceutically acceptable salts thereof in the present invention as an active ingredient, has antibacterial activities and may be used in preparing a medicament for treating and/or preventing a bacterial infectious disease.

The "therapeutically effective amount" refers to the amount of the compound is enough to significantly improve the condition without causing serious side effects. The therapeutically effective amount may be determined according to the age, status, course of treatment, and the like of the subject to be treated.

The "pharmaceutically acceptable carrier" refers to one or more compatible solid or liquid fillers or gel materials which are suitable for administration to a human, with sufficient purity and sufficiently low toxicity. Herein, "compatible" means that the components in the composition are capable of intermixing with the compounds of the invention and with each other, without significantly decreasing the pharmacological activities of the compound. Examples of pharmaceutically acceptable carriers include sugars (such as glucose, sucrose, lactose and the like), starches (such as corn starch, potato starch and the like), celluloses and derivatives thereof (such as sodium carboxymethylcellulose, sodium ethylcellulose, cellulose acetate and the like), gelatin, talc, solid lubricants (such as stearic acid, magnesium stearate), calcium sulfate, vegetable oils (such as soybean oil, sesame oil, peanut oil, olive oil and the like), polyols (such as propylene glycol, glycerol, mannitol, sorbitol), emulsifiers (such as tween), wetting agents (such as sodium dodecyl sulfate), colorants, flavoring agents, stabilizers, antioxidants, preservatives, pyrogen-free water, etc.

Advantageous Effects

In vitro bacteriostatic assays of the compounds of Formula (I) prepared by the invention showed that the compounds have antibacterial activities against vancomycin-resistant *Staphylococcus aureus* significantly better than vancomycin. Some preferred compounds have 10-100 folds better activity than vancomycin and 4-10 times more active than telavancin which was marketed in 2009. Antibacterial experimental results indicate that the derivatizing strategies of introducing sugar moieties on the amino acid aromatic ring at $7^{th}$ resorcinol position of vancomycin and introducing a biphenyl group on the vancosamine moiety of vancomycin can significantly enhance the antibacterial activity of vancomycin, particularly on vancomycin-resistant *Staphylococcus aureus*.

DETAILED DESCRIPTION OF EXEMPLARY EMBODIMENTS

Figure 1:
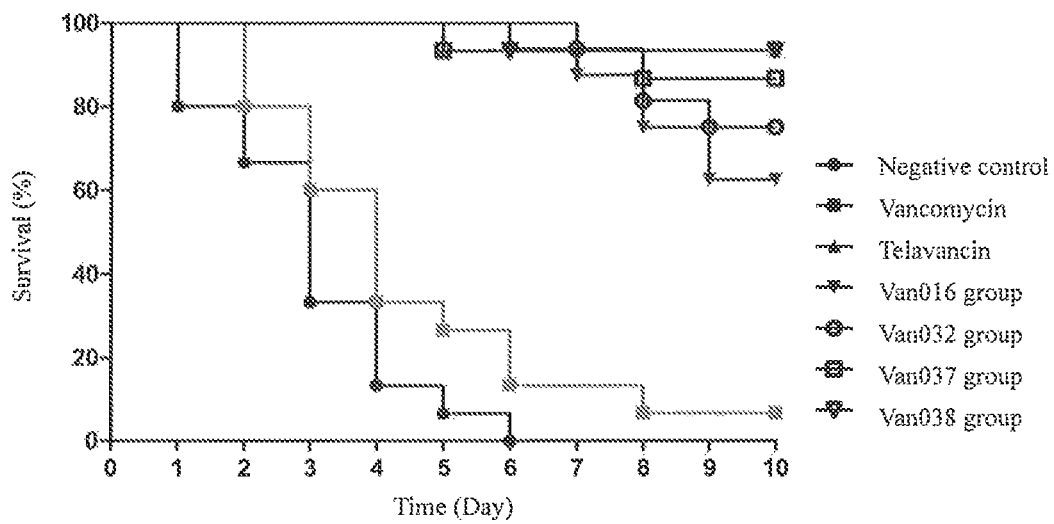
FIG. 1 shows the results of a bacterial infection lethal challenge assay of Van016, Van032, Van037 and Van038 in mice.

The present invention will be further illustrated based on the following examples. These examples are for illustrative purposes only and are not intended to limit the scope of the invention in any way.

In the following examples, standard procedures and purification methods known to those skilled in the art can be used. Unless otherwise specified, the starting materials are commercially available from, such as Aldrich Chemicals Co. and Acros Organics. The commercially obtained solvents and reagents are generally used as received without further purification. Anhydrous solvents are treated by standard methods, and other reagents are commercially analytical reagents. Unless otherwise stated, all temperatures are expressed in degrees Celsius (° C.). The room temperature or ambient temperature means 20~25° C. The structure of a compound was determined by nuclear magnetic resonance spectroscopy (NMR) and/or mass spectrometry (MS).

In nuclear magnetic resonance spectrum, the chemical shift (δ) is expressed in parts per million (ppm). $^1$H-NMR was measured on a Mercury-600 MHz or a Bruker (AV-400) 400 MHz nuclear magnetic resonance instrument with deuterated dimethyl sulfoxide (DMSO-$d_6$), deuterated chloroform (CDCl$_3$), deuterated methanol (MeOD-$d_4$), or deuterated water (D$_2$O) as a solvent, and tetramethylsilane (TMS) as an internal standard.

High resolution mass spectrometry (HRMS) was measured on an Agilent 6230 Series TOF LC-MS spectrometer. If the intensity of ions containing chlorine or bromine is described, the expected intensity ratio (For ions containing $^{35}$Cl/$^{37}$Cl, the ratio is about 3:1, and for ions containing $^{79}$Br/$^{81}$Br, the ratio is about 1:1), and only intensity of the ion with lower mass is given.

HPLC: an Agilent 1260 Analytical High Performance Liquid Chromatography System (Agilent) and a LC3000 Preparative High Performance Liquid Chromatography System (Beijing Innovation Tongheng Technology Co., Ltd.) were used. Analytical reverse-phase HPLC conditions: C18 column (5 μm, 4.6×250 mm), UV detection band is at 214 nm and 280 nm, elution conditions: a gradient of 0-90% acetonitrile containing 0.1% v/v TFA over 30 min. Preparative High performance liquid chromatography conditions: C18 column (5 μm, 19×250 mm), UV detection band is at 214 nm and 280 nm, elution conditions: a gradient of 0-90% acetonitrile containing 0.1% v/v TFA over 30 min.

Column chromatography was performed generally using a silica gel of 200-300 mesh as a supporter.

In the above discussion and the examples below, the following abbreviations refer respectively to the definitions herein. If an abbreviation is not defined, it has a generally accepted meaning.

TLC thin layer chromatography;
DIPEA N,N-diisopropylethylamine;
DMF N,N-dimethylformamide;
DMSO dimethyl sulfoxide;
DCM dichloromethane;
EtOAc ethyl acetate;
Hexane hexane;
TfOH trifluoromethanesulfonic acid;
DCC dicyclohexylcarbodiimide;
Fmoc-Cl 9-Fluorenylmethyl chloroformate;
Pd/C palladium on carbon;
HBTU O-(benzotriazol-1-yl)-N,N,N',N'-tetramethyluronium hexafluorophosphate;
TFA trifluoroacetic acid.

Preparation of starting materials and intermediates

Preparation 1

Preparation of N-(9-fluorenylmethoxycarbonyl)-n-decylaminoacetaldehyde (1)

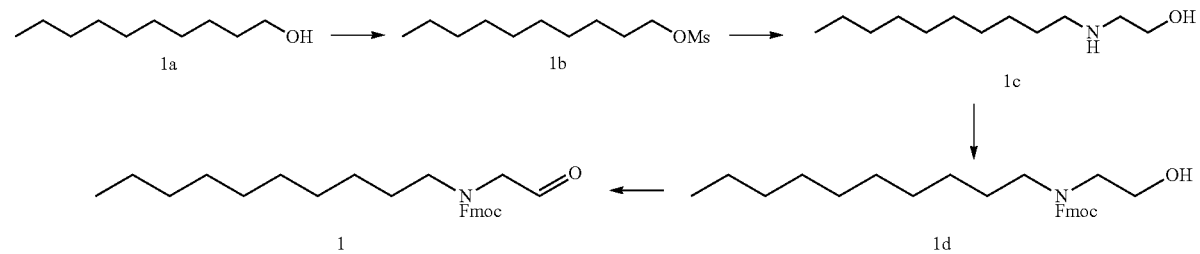

Decyl alcohol 1a (9.5 mL, 50 mmol), 25 mL of dichloromethane, methanesulfonyl chloride (5.4 mL, 70 mmol) in dichloromethane (25 mL) were mixed and stirred at 0° C. for 5 min. Pyridine (5 mL) was added and stirred at room temperature for 24 h. The residue was concentrated to remove solvent and dissolved in hexane (100 mL), washed with water (100 mL). The combined organic layers were dried over sodium sulfate, filtered and concentrated to give a crude decyl methanesulfonate 1b as a colorless oil, which was directly used in the next step. The crude decyl methanesulfonate 1b was dissolved in 30 mL of ethanol, and a solution of 2-aminoethanol (6.1 g, 100 mmol) in ethanol (30 mL) was added dropwise over 15 min at room temperature. After the addition, the reaction mixture was heated to 90° C. and stirred for 24 h. The residue is concentrated to remove solvents, added with dichloromethane (100 mL) and water (100 mL) and the layers were separated. The combined organic layers were dried over sodium sulfate, filtered and concentrated to give crude 2-(decylamino)ethanol 1c (7.5 g, yield 75%) as a colorless oil, MS (ESI$^+$): 201.8 [M+H]$^+$.

The crude 2-(decylamino)ethanol 1c (4.15 g). DIPEA (3.6 mL), 30 mL of dichloromethane, and a solution of Fmoc-Cl (4.7 g) in dichloromethane (10 mL) were mixed and stirred at 0° C. for 1 h. TLC showed that the reaction was almost complete. The reaction mixture was washed with saturated aqueous solution of sodium bicarbonate (500 mL) and 0.1 N HCl (200 mL). The combined organic layers were dried over anhydrous sodium sulfate, filtered and concentrated to give crude N-decyl-N-Fmoc-aminoethanol 1d (8 g) as a colorless oil. MS (ESI$^+$): 424.3 [M+H]$^+$.

$^1$H NMR (400 MHz, CDCl$_3$) δ (ppm) 7.84 (d, J=7.5 Hz, 2H), 7.66 (d, J=7.4 Hz, 2H), 7.52-7.36 (m, 4H), 4.61 (d, J=5.8 Hz, 2H), 4.31 (t, J=5.7 Hz, 1H), 3.80 (s, 1H), 3.45 (s, 2H), 3.13 (s, 3H), 1.63-1.07 (m, 18H), 0.96 (t, J=6.6 Hz, 3H).

The crude N-decyl-N-Fmoc-aminoethanol 1d (1 g), DIPEA (2 mL), 20 mL of dichloromethane were mixed, and stirred at −5° C. (ice-acetone bath) for 15 min. Then, a solution of pyridine sulfur trioxide (1.88 g) in DMSO (6 mL) was added before stirred at −5° C. for 30 min. TLC showed that the reaction is almost complete. The reaction mixture was poured into a saturated aqueous solution of sodium bicarbonate (50 mL) with crushed ice, and the two phases were separated. The organic layer was washed with 0.1 N HCl (50 mL). The combined organic layers were dried over anhydrous sodium sulfate, filtered and concentrated to afford crude N-(9-fluorenylmethoxycarbonyl)-n-decylaminoacetaldehyde 1 (0.9 g) as a yellow oil. MS (ESI$^+$): m/z 422.4 [M+]$^+$.

$^1$H NMR (400 MHz, CDCl$_3$): δ (ppm)=9.38 (d, J=117.7 Hz, 1H), 7.84 (d, J=7.5 Hz, 2H), 7.66 (d, J=7.4 Hz, 2H), 7.52-7.36 (m, 4H), 4.61 (d, J=5.8 Hz, 2H), 4.31 (t, J=5.7 Hz, 1H), 3.80 (s, 1H), 3.33-3.18 (m, 2H), 3.18-3.04 (m, 1H), 1.52-1.36 (m, 1H), 1.37-1.14 (m, 14H), 1.15-1.03 (m, 1H), 0.97-0.79 (m, 3H).

Preparation 2 Preparation of
2-aminoethyl-α-D-mannopyranoside (2)

1,2,3,4,6-O-acetyl-D-mannopyranoside (2a)

D-mannitol (5 g, 27.9 mmol) was dissolved in 25 mL of pyridine, ice-cooled at 0° C., and then 25 mL of acetic anhydride was slowly added. The mixture was stirred at room temperature for 16 h. Solvent was distilled off under reduced pressure. The residue was dissolved in ethyl acetate, washed sequentially with 1N hydrochloric acid, pure water and brine, dried over anhydrous sodium sulfate and filtered. The remaining ethyl acetate was distilled off under reduced pressure to afford a peracetylated mannoside (2a) (10.6 g, 27.1 mmol, yield 97%) as a clear viscous oil. And the product contained two configurations (α-isomer/β-isomer=33:67, w/w).

$^1$H NMR (400 MHz, CDCl$_3$, a mixture of two isomers): NMR data of β-isomer δ (ppm)=1.98 (s, 3H, COCH$_3$), 2.07 (s, 3H, COCH$_3$), 2.08 (s, 3H, COCH$_3$), 2.15 (s, 3H, COCH$_3$), 2.19 (s, 3H, COCH$_3$), 3.99-4.05 (m, 1H, 5-H), 4.07 (dd, J=2.4, 12.4 Hz, 1H, 6-H$_a$), 4.26 (dd, J=4.9, 12.4 Hz, 1H, 6-H$_b$), 5.23 (dd, J=2.0, 3.1 Hz, 1H, 3-H), 5.31-5.34 (m, 2H, 3-H, 4-H), 6.06 (d, J=2.0 Hz, 1H, 1-H); NMR data of α-isomer δ (ppm)=1.98 (s, 3H, COCH$_3$), 2.03 (s, 3H, COCH$_3$), 2.07 (s, 3H, COCH$_3$), 2.15 (s, 3H, COCH$_3$), 2.16 (s, 3H, COCH$_3$), 3.79 (ddd, J=2.4, 5.3, 9.9 Hz, 1H, 5-H), 4.11 (dd, J=2.4, 12.4 Hz, 1H, 6-H$_a$), 4.28 (dd, J=5.3, 12.4 Hz, 1H, 6-H$_b$), 5.11 (dd, J=3.3, 10.0 Hz, 1H, 3-H), 5.27 (t, J=10.0 Hz, 1H, 4-H), 5.46 (dd, J=1.2, 3.3 Hz, 1H. 2-H), 5.84 (d, J=1.2 Hz, 1H, 1-H).

Phenyl 2,3,4,6-tetra-O-acetyl-1-sulfo-n-D-mannopyranoside (2b)

The peracetylated mannoside 2a (4.5 g, 12.5 mmol) was added with 10 mL of dichloromethane and thiophenol (1.96 mL, 19.08 mmol), and stirred at room temperature for 20 min. Boron trifluoride etherate (7.8 mL, 63.6 mmol) was added dropwise under ice-bath. The mixture was stirred further for 15 min under ice bath, warmed to room temperature, and stirred for 16 h. The reaction mixture was diluted with dichloromethane (50 mL), added with ice water (100 mL) and stirred. The organic layer was separated, washed with a saturated aqueous solution of sodium bicarbonate and brine, and dried over anhydrous sodium sulfate. The solvent was removed under reduced pressure and the residue was purified by column chromatography (ethyl acetate/hexane 1:5-1:3, v/v) to give phenyl 2,3,4,6-tetra-O-acetyl-1-sulfo-α-D-mannopyranoside 2b (4.4 g, yield 80%) as a white solid. HRMS (ESI$^+$): [M+Na]$^+$ calculated for C$_{20}$H$_{24}$O$_9$SNa 463.1033, found 463.1039.

$^1$H NMR (400 MHz, CDCl$_3$): δ (ppm)=7.50-5.30 (m, 5H, ArH), 5.50 (dd, J$_{1,2}$=1.6 Hz, J$_{2,3}$=3.2 Hz, 1H, H-2), 5.50 (d, 1H, H-1), 5.33 (dd, J$_{4,5}$=9.8 Hz, J$_{3,4}$=9.9 Hz, 1H, H-4), 5.32 (dd, 1H, H-3), 4.55 (ddd, J$_{5,6a}$=2.3 Hz, J$_{5,6b}$=5.9 Hz, 1H, H-5), 4.31 (dd, J$_{6a,6b}$=12.3 Hz, 1H, H-$_{6b}$), 4.11 (dd, 1H, H-$_{6a}$), 2.16, 2.08, 2.06, 2.02 (s, 12H, 4×OCCH$_3$).

2-(Benzyloxycarbonyl)aminoethyl 2,3,4,6-tetra-O-acetyl-α-D-mannopyranoside (2c)

Phenyl 2,3,4,6-tetra-O-acetyl-1-sulfo-α-D-mannopyranoside 2b (2 g, 4.5 mmol) and N-(benzyloxycarbonyl)etha-

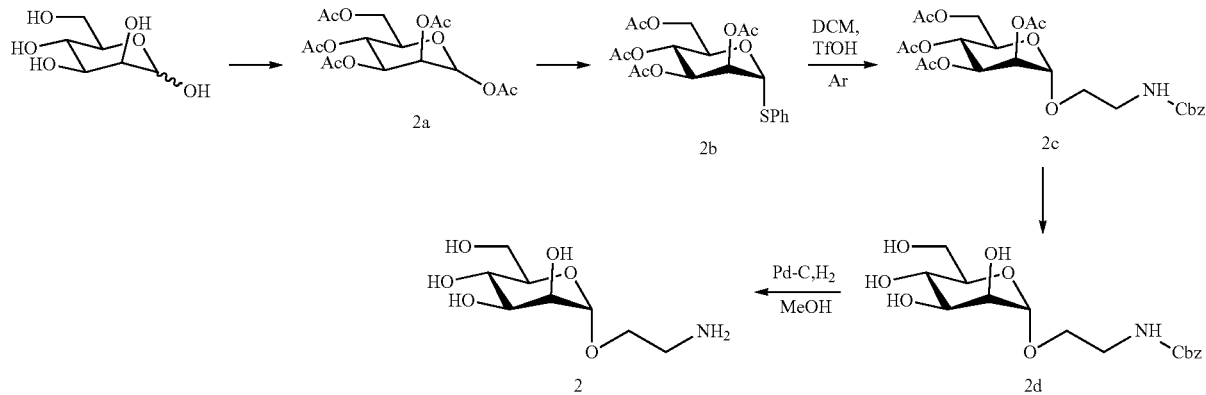

nolamine (1.1 g, 5.4 mmol) were dissolved in anhydrous dichloromethane in the presence of 4 Å molecular sieve under argon. The mixture was cooled to 0° C., added with N-iodosuccinimide (1.52 g, 6.75 mmol), reacted at 0° C. for 15 min, and then added with trifluoromethanesulfonic acid (80 μL, 0.9 mmol). The reaction mixture was stirred overnight at room temperature, quenched by addition of triethylamine, diluted with dichloromethane, and filtered. The resultant organic layer was washed with a saturated aqueous solution of sodium bicarbonate, brine, and dried over anhydrous sodium sulfate. The solvent was distilled off under reduced pressure and the product was separated by column chromatography (eluting with ethyl acetate/hexane 40:60 50:50, v/v) to afford 2-(benzyloxycarbonyl)aminoethyl 2,3,4,6-tetra-O-acetyl-α-D-mannopyranoside (1.66 g, 3.17 mmol, yield 57%). HRMS (ESI$^+$): calculated for $C_{24}H_{31}NO_{12}$ [M+H]$^+$526.1925, found 526.1913.

$^1$H NMR (400 MHz, CDCl$_3$): δ (ppm)=2.00 (s, 3H, COCH$_3$), 2.04 (s, 3H, COCH$_3$), 2.09 (s, 3H, COCH$_3$), 2.16 (s, 3H, COCH$_3$), 3.36-3.53 (m, 2H, CH$_2$NH), 3.58 (ddd, J=3.6, 6.8, 10.2 Hz, 1H, CH$_a$H$_b$CH$_2$NH), 3.78 (ddd, J=3.9, 6.2 10.2 Hz, 1H, CH$_a$H$_b$CH$_2$NH), 3.97 (ddd, J=2.3, 5.7 9.5 Hz, 1H, 5-H). 4.08 (dd, J=2.3, 12.2 H 1H, 6-H$_a$), 4.26 (dd, J=5.7, 12.2 Hz, 1H, 6-H$_b$), 4.82 (d, J=1.7 Hz, 1H, 1-H), 5.12 (s, 2H, CH$_2$Ph), 5.20 (bt, J=5.8 Hz, 1H, NH), 5.25 (dd, J=1.7, 3.2 Hz, 1H, 2-H), 5.26 (dd, J=9.5, 10.1 H), 5.31 (dd, J=3.2, 10.0 Hz, 1H, 3-H), 7.29-7.39 (m, 5H, C$_6$H$_5$).

2-(Benzyloxycarbonyl)aminomethyl-α-D-mannopyranoside (2d)

2-(Benzyloxycarbonyl)aminoethyl 2,3,4,6-tetra-O-acetyl-α-D-mannopyranoside 2c (466 mg, 0.887 mmol) was dissolved in a solution of 4N sodium methanolate in methanol. The reaction was maintained at pH 10, and reacted at room temperature for 4 h. The reaction mixture was added with a strong acid ion exchange resin, adjusted to pH 7-8, and filtered. The solvent was distilled off under reduced pressure to give 2-(benzyloxycarbonyl)aminomethyl-α-D-mannopyranoside 2d (301 mg, 0.842 mmol, yield 95%) as a colorless oil. HRMS (ESI$^+$): calculated for $C_{16}H_{23}NO_8$ [M+Na]$^+$ 380.1321, found 380.1316.

$^1$H NMR (400 MHz, MeOD-d$_4$): δ (ppm)=3.27-3.39 (m, 2H, CH$_2$NH), 3.47-3.55 (m, 2H, 5-H, CH$_a$H$_b$CH$_2$NH), 3.60 (t, J=9.5 Hz, 1H, 4-H), 3.68 (dd, J=5.8, 11.7 Hz, 1H, 6-H$_a$), 3.69 (dd, J=3.4, 9.3 Hz, 1H, 3-H), 3.74 (ddd, J=4.9, 6.4, 10.2 Hz, 1H, CH$_a$H$_b$CH$_2$NH), 3.80 (dd, J=1.7, 3.4 Hz, 1H, 2-H), 3.81 (dd, J=2.3, 11.7 Hz, 1H, 6-H$_b$), 4.75 (d, J=1.6 Hz, 1H, 1-H), 5.06 (s, 2H, CH$_2$Ph), 7.24-7.36 (m, 5H, C$_6$H$_5$).

2-Aminoethyl-α-D-mannopyranoside (2)

2-(Benzyloxycarbonyl)aminomethyl-α-D-mannopyranoside 2d (285 mg, 0.798 mmol) was dissolved in methanol, and added with Pd—C (20%) 30 mg. The reaction mixture was charged with hydrogen (at a pressure of 1.5 Pa), stirred at room temperature for 4 h and filtered through a sintered glass funnel to give 2-Aminoethyl-α-D-mannopyranoside 2 301 mg (0.842 mmol, yield 95%). HRMS (ESI$^+$): calculated for $C_{16}H_{23}NO_8$ [M+Na]$^+$ 380.1321, found 380.1316.

$^1$H NMR (400 MHz, MeOD-d$_4$): δ (ppm)=2.82-2.86 (m, 2H, CH$_2$NH$_2$), 3.48 (ddd, J=4.7, 5.9, 10.2 Hz, 1H, CH$_a$H$_b$CH$_2$NH$_2$), 3.56 (ddd, J=2.1, 5.8, 9.7 Hz, 1H, 5-H), 3.63 (t, J=9.4 Hz, 1H, 4-H), 3.73 (dd, J=5.8, 11.8 Hz, 1H, 6-H$_a$), 3.74 (dd, J=3.4, 9.1 Hz, 1H, 3-H), 3.79 (ddd, J=4.7, 5.9, 10.2 Hz, 1H, CH$_a$H$_b$CH$_2$NH$_2$), 3.86 (dd, J=1.7, 3.4 Hz, 1H, 2-H), 3.86 (dd, J=2.1, 11.8 Hz, 1H, 6-H$_b$), 4.80 (d, J=1.7 Hz, 1H, 1-H).

Preparation 3 Preparation of 2-aminoethyl-β-D-glucopyranoside (3)

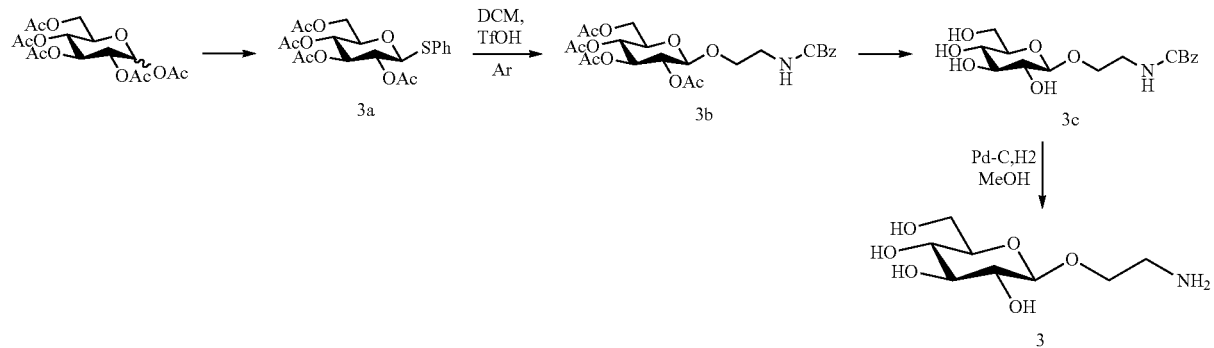

3a-c and 3 were prepared using the same needed materials, reagents and preparation method as those in preparation 2 except that D-mannitol in preparation 2 was replaced with glucose.

Phenyl 2,3,4,6-tetra-O-acetyl-1-sulfo-β-D-glucoside (3a)

$^1$H NMR (400 MHz, CDCl$_3$): δ (ppm)=7.55-7.49 (m, 2H), 7.34 (dd, J=5.1, 1.9 Hz, 3H), 5.24 (t, J=9.4 Hz, 1H), 5.03 (d, J=26.5, 9.7 Hz, 2H), 4.73 (d, J=10.1 Hz, 1H). 4.27-4.17 (m, 2H), 3.75 (ddd, J=10.0, 5.0, 2.6 Hz, 1H), 2.10 (d, J=2.9 Hz, 6H), 2.04 (s, 3H), 2.01 (s, 3H).

2-(Benzyloxycarbonyl)aminoethyl 2,3,4,6-tetra-O-acetyl-β-D-glucoside (3b)

HRMS (ESI$^+$): calculated for $C_{24}H_{31}NO_{12}$ [M+H]$^+$ 526.1925, found 526.1899.

$^1$H NMR (400 MHz, CDCl$_3$): δ (ppm)=2.00 (s, 6H, 2 COCH$_3$), 2.03 (s, 3H, COCH$_3$), 2.06 (s, 3H, COCH$_3$), 3.37-3.41 (m, 2H, CH$_2$NH), 3.68 (ddd, J=2.5, 4.8, 9.9 Hz, 1H, 5-H), 3.69-3.74 (m, 1H, OCH$_a$H$_b$CH$_2$), 3.87 (ddd, J=4.1, 5.5, 10.0 Hz, 1H, OCH$_a$H$_b$CH$_2$), 4.14 (dd, J=2.4, 12.3 Hz, 6-H$_a$), 4.14 (dd, J=4.8, 12.4 Hz, 1H, 6-H$_b$), 4.48 (d, J=8.0 Hz, 1H, 1-H), 4.93 (dd, J=8.0, 9.6 Hz, 1H, 2-H), 5.05 (dd, J=9.4, 9.7 Hz, 1H, 4-H), 5.09 (s, 2H, CH$_2$Ph), 5.17 (m, 1H, NHCBz), 5.19 (dd, J=9.4, 9.6 Hz, 3-H), 7.33-7.36 (m, 5H, C$_6$H$_5$).

2-(Benzyloxycarbonyl)aminomethyl-β-D-glucopyranoside (3c)

HRMS (ESI$^+$): calculated for C$_{16}$H$_{23}$NO$_8$ [M+Na]$^+$ 380.1321, found 380.1318.

$^1$H NMR (400 MHz, MeOD-d$_4$): δ (ppm)=3.17 (dd, J=7.9, 9.0 Hz, 1H, 2-H), 3.22-3.29 (m, 3H, 4-H, 5-H, CH$_a$H$_b$NH), 3.32-3.38 (m, 1H, CH$_a$H$_b$NH), 3.34 (t, J=8.7 Hz, 3-H), 3.58 (ddd, J=4.2, 6.9, 10.4 Hz 1H, CH$_a$H$_b$CH$_2$NH), 3.62 (dd, J=5.2, 12.0 Hz, 1H, 6-H$_b$), 3.81 (dd, J=2.0, 11.9 Hz, 1H, 6-H$_b$), 3.86 (ddd, J=5.6, 7.7, 10.2 Hz, 1H, CH$_a$H$_b$CH$_2$NH), 4.22 (d, J=7.8 Hz, 1H, 1-H), 5.02 (s, 2H, CH$_2$Ph), 7.23-7.29 (m, 5H, C$_6$H$_5$).

2-Aminoethyl-β-D-glucopyranoside (3)

HRMS (ESI$^+$): calculated for C$_8$H$_{17}$NO$_6$ [M+H]$^+$ 224.1134, found 224.1135.

$^1$H NMR (400 MHz, MeOD-d$_4$): δ (ppm)=2.84-2.86 (m, 2H, CH$_2$NH$_2$), 3.15 (dd, J=7.8, 9.2 Hz, 1H, 2-H), 3.21-3.24 (m, 2H, 4-H, 5-H), 3.31 (dd, J=9.0, 9.1 Hz, 1H, 3-H), 3.58-3.63 (m, 2H, 6-H$_a$, CH$_a$H$_b$CH$_2$NH), 3.81 (dd, J=1.3, 11.9 Hz, 1H, 6-H$_b$), 3.88 (ddd, J=5.0, 7.7, 9.9 Hz, 1H, CH$_a$H$_b$CH$_2$NH), 4.22 (d, J=7.8 Hz, 1H, 1-H).

Preparation 4 Preparation of 2-aminoethyl-β-D-galactopyranoside (4)

2-(Benzyloxycarbonyl)aminoethyl 2,3,4,6-tetra-O-acetyl-β-D-galactoside (4b)

HRMS (ESI$^+$): calculated for C$_{24}$H$_{31}$NO$_{12}$ [M+Na]$^+$ 548.1744, found 548.1747.

$^1$H NMR (400 MHz, CDCl$_3$): δ (ppm)=1.90 (s, 3H, COCH$_3$), 1.93 (s, 3H, COCH$_3$), 1.95 (s, 3H, COCH$_3$), 2.07 (s, 3H, COCH$_3$), 3.32 (m, 2H, CH$_2$NH), 3.62 (ddd, J=3.6, 7.1, 10.2 Hz, 1H, CH$_a$H$_b$CH$_2$NH), 3.80-3.82 (m, 2H, 5-H, CH$_a$H$_b$CH$_2$NH), 4.06 (d, J=6.6 Hz, 2H, 6-H$_2$), 4.38 (d, J=7.9 Hz, 1H, 1-H), 4.93 (dd, J=3.4, 10.5 Hz, 1H, 3-H), 5.02 (s, 2H, CH$_2$Ph), 5.10 (dd, J=8.0, 10.4 Hz, 1H, 2-H), 5.19 (t, J=5.4 Hz, 1H, NH), 5.31 (dd, J=0.7, 3.4 H, 1H, 4-H), 7.22-7.30 (m, 5H, C$_6$H$_5$).

2-(Benzyloxycarbonyl)aminomethyl-β-D-galactopyranoside (4c)

HRMS (ESI$^+$): calculated for C$_{16}$H$_{23}$NO$_8$ [M+Na]$^+$ 380.1316, found 380.1308.

$^1$H NMR (400 MHz, MeOD-d$_4$): δ (ppm)=3.30 (ddd, J=4.2, 6.8, 14.2 Hz, 1H, CH$_a$H$_b$NH), 3.40 (ddd, J=4.1, 6.2, 14.2 Hz, 1H, CH$_a$H$_b$NH), 3.46 (dd, J=3.2, 9.7 Hz, 1H, 3-H), 3.50 (ddd, J=1.0, 5.3, 6.8 Hz, 1H, 5-H), 3.52 (dd, J=7.3, 9.8 Hz, 1H, 2-S10H), 3.63 (ddd, J=4.0, 6.8, 10.5 Hz, 1H, CH$_a$H$_b$CH$_2$NH), 3.70 (dd, J=5.3, 11.4 Hz, 1H, 6-H$_a$), 3.75 (dd, J=6.9, 11.3 Hz, 1H, 6-H$_b$), 3.82 (dd, J=1.0, 3.2 Hz, 1H, 4-H), 3.91 (ddd, J=4.2, 6.2, 10.4 Hz, 1H, CH$_a$H$_b$CH$_2$NH), 4.22 (d, J=7.3 Hz, 1H, 1-H), 5.06 (s, 2H, CH$_2$Ph), 7.24-7.37 (m, 5H, C$_6$H$_5$).

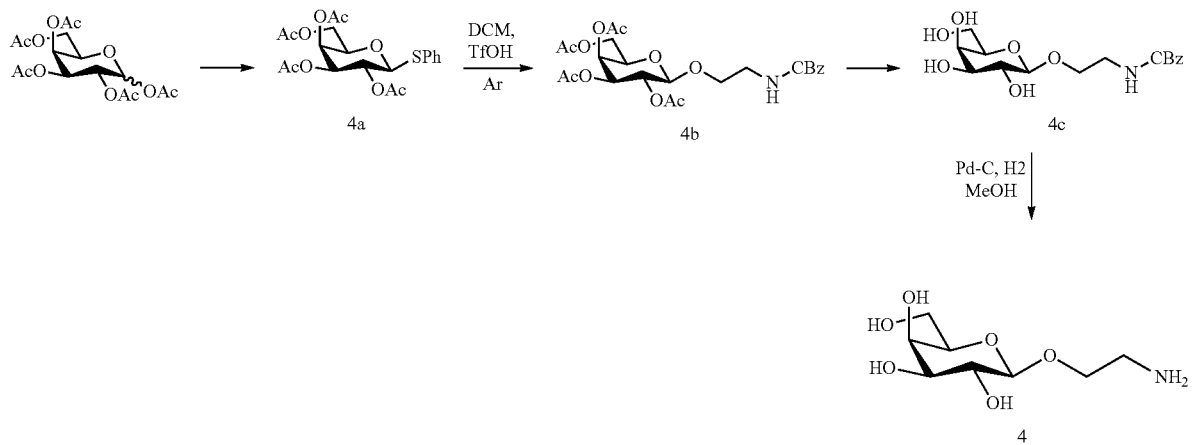

4a-c and 4 were prepared using the same needed materials, reagents and preparation method as those in preparation 2 except that D-mannitol in preparation 2 was replaced with galactose.

Phenyl 2,3,4,6-tetra-O-acetyl-1-sulfo-β-D-galactoside (4a)

$^1$H NMR (400 MHz, CDCl$_3$): δ (ppm)=7.54 (ddd, J=7.0, 3.8, 2.1 Hz, 2H). 7.37-7.33 (m, 3H), 5.44 (d, J=3.2 Hz, 1H), 5.27 (t, J=9.9 Hz, 1H), 5.07 (dd, J=10.0, 3.4 Hz, 1H), 4.74 (d, J=10.0 Hz, 1H), 4.22 (dd, J=11.3, 7.0 Hz, 1H), 4.17-4.11 (m, 1H), 3.96 (t, J=6.6 Hz, 1H), 2.15 (s, 3H), 2.12 (s, 3H), 2.07 (s, 4H), 2.00 (s, 3H).

2-Aminoethyl-β-D-galactopyranoside (4)

HRMS (ESI$^+$): calculated for C$_8$H$_{17}$NO$_6$ [M+H]$^+$ 224.1134, found 224.1133.

$^1$H NMR (400 MHz, MeOD-d$_4$): δ (ppm)=2.80 (ddd, J=4.2, 6.3, 13.4 Hz, 1H, CH$_a$H$_b$NH$_2$), 2.84 (ddd, J=4.4, 5.5, 13.4 Hz, 1H, CH$_a$H$_b$NH$_2$), 3.45 (dd, J=3.3, 9.7 Hz, 1H, 3-H), 3.49 (ddd, J=1.0, 5.3, 7.0 Hz, 1H, 5-H), 3.52 (dd, J=7.5, 9.7 Hz, 1H, 2-H), 3.61 (ddd, J=4.4, 6.3, 10.5 Hz, 1H, CH$_a$H$_b$CH$_2$NH$_2$), 3.69 (dd, J=5.3, 11.3 Hz, 1H, 6-H$_a$), 3.73 (dd, J=7.0, 11.3 Hz, 1H, 6-H$_b$), 3.80 (dd, J=1.0, 3.3 Hz, 1H, 4-H). 3.91 (ddd, J=4.2, 5.5, 10.3 Hz, 1H, CH$_a$H$_b$CH$_2$NH$_2$), 4.21 (d, J=7.5 Hz, 1H, 1-H).

Preparation 5 Preparation of 2-aminoethyl-2-acetamido-2-deoxy-β-D-glucopyranoside (5)

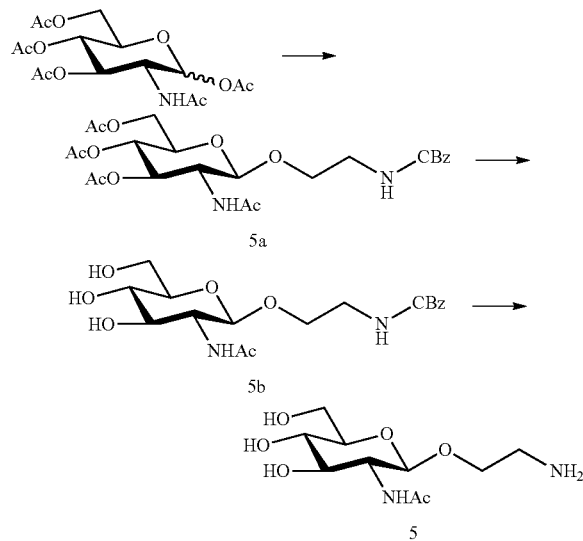

5a, 5b and 5 were prepared using the same needed materials, reagents and preparation method as those in preparation 2 except that D-mannitol in preparation 2 was replaced with N-Acetyl-D-glucosamine.

2-(Benzyloxycarbonyl)aminoethyl 2-acetamido-3,4,6-tri-O-acetyl-2-deoxy-β-D-glucopyranoside (5a)

HRMS (ESI+): calculated for $C_{24}H_{32}N_2O_{11}$ [M+H]+ 525.2084, found 525.2077.
$^1$H NMR (500 MHz, CDCl$_3$): δ (ppm)=1.82 (s, 3H, COCH$_3$), 1.96 (s, 6H, 2COCH$_3$), 1.98 (s, 3H, COCH$_3$), 3.21-3.29 (m, 1H, CH$_a$H$_b$NH), 3.33-3.42 (m, 1H, CH$_a$H$_b$NH), 3.61 (m, 214, 5-H, CH$_a$H$_b$CH$_2$NH), 3.80 (ddd, J=3.5, 5.9, 9.9 Hz, 1H, CH$_a$H$_b$CH$_2$NH), 3.84 (dt, 1=8.6, 10.2 Hz, 1H, 2-H). 4.06 (dd, J=2.0, 12.3 Hz, 1H, 6-H$_a$), 4.16 (dd, J=4.8, 12.3 Hz, 1H, 6-H$_b$), 4.54 (d, J=8.3 Hz, 1H, 1-H), 4.98 (dd, J=9.5, 9.8 Hz, 1H, 4-H), 5.02 (s, 2H, CH$_2$Ph), 5.12 (dd, J=9.8, 10.2 Hz, 1H, 3-H), 5.31 (t, J=5.2 Hz, 1H, CH$_2$NH), 5.87 (d, J=8.8 Hz, 1H, 2-NH), 7.23-7.31 (m, 5H, C$_6$H$_5$).

2-(Benzyloxycarbonyl)aminoethyl 2-acetylamino-2-deoxy-β-D-glucopyranoside (5b)

HRMS (ESI+): calculated for $C_{18}H_{26}N_2O_8$ [M+Na]+ 421.1587, found 421.1570.
$^1$H NMR (400 MHz, MeOD-d$_4$): δ (ppm)=1.93 (s, 3H, COCH$_3$), 3.23-3.34 (m, 4H, 4-H, 5-H, CH$_2$NH), 3.43 (dd, J=8.4, 10.3 Hz, 1H, 3-H), 3.58 (ddd, J=5.4, 5.6, 10.6 Hz, 1H, CH$_a$H$_b$CH$_2$NH), 3.65 (dd, J=8.4, 10.3 Hz, 1H, 2-H), 3.66 (dd, J=5.6, 11.9 Hz, 1H, 6-H$_a$), 3.84 (m, 1H, CH$_a$H$_b$CH$_2$NH), 3.86 (dd, J=2.2, 12.0 Hz, 1H. 6-H$_b$), 4.38 (d, J=8.4 Hz, 1H, 1-H), 5.05 (s, 2H, CH$_2$Ph), 7.35-7.25 (m, 5H, C$_6$H$_5$).

2-Aminoethyl-2-acetamido-2-deoxy-β-D-glucopyranoside (5)

HRMS (ESI+): calculated for $C_{10}H_{20}N_2O_6$ 265.1400, found 265.1404 [M+H]+.

$^1$H NMR (400 MHz, D$_2$O): δ (ppm)=2.05 (s, 3H, COCH$_3$), 2.69-2.85 (m, 2H, CH$_2$NH$_2$), 3.34-3.52 (m, 2H, 4-H, 5-H), 3.52-3.59 (m, 1H, 3-H), 3.59-3.67 (m, 1H, CH$_a$H$_b$CH$_2$NH$_2$), 3.71-3.80 (m, 2H, 2-H, 6-H$_a$), 3.87-4.01 (m, 2H, 6-H$_b$, CH$_a$H$_b$CH$_2$NH$_2$), 4.53 (d, J=8.4 Hz, 1H, 1-H).

Preparation 6 Preparation of Gluconolactone Derivative (6)

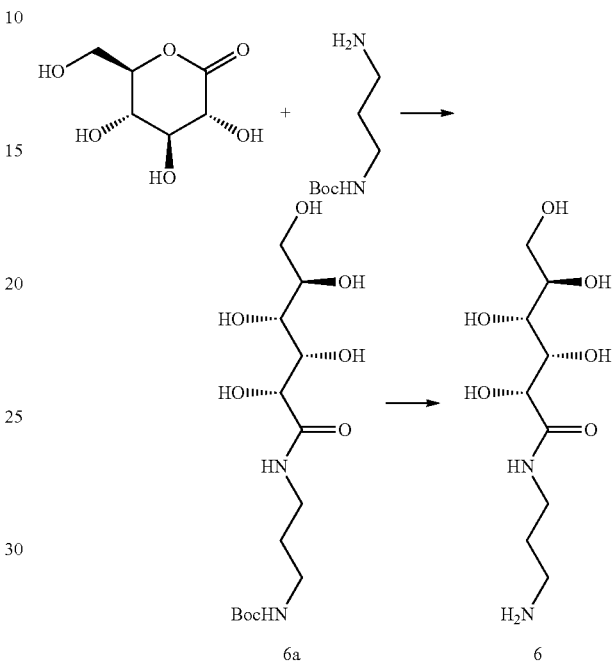

Gluconolactone (2 g, 11.36 mmol) was dissolved in 12 mL of methanol and added with N-Boc-1,3-propanediamine (2.37 g, 13.63 mmol). The mixture was refluxed for 4 h, and the methanol was distilled off under reduced pressure to give a white solid, which was washed with ethyl acetate and dichloromethane, and vacuumed by an oil pump to afford a white solid 6a (3.6 g, yield 90%). HRMS (ESI+) calculated for $C_{14}H_{28}N_2O_8$ [M+Na]+375.1743, found 375. 1726.

6a: $^1$H NMR (400 MHz, DMSO-d$_6$) δ 4.48-3.47 (m, 4H), 4.35-3.57 (m, 2H), 3.92-3.07 (m, 4H), 1.51-1.49 (m, 2H), 1.37 (s, 9H).

6a was dissolved in 5 mL of methanol, added with 4N hydrochloric acid, stirred at room temperature for 4 h, and distilled off the solvent under reduced pressure to afford a white solid 6.

HRMS (ESI+) calculated for $C_9H_{20}N_2O_6$ 253.1400, found 253.1381 [M+H]+.

6: $^1$H NMR (400 MHz, DMSO-d$_6$) δ 4.23-3.53 (m, 4H), 4.12-3.79 (m, 2H), 2.93-2.87 (t, 4H), 1.92-1.88 (m, 2H).

Preparation 7 Preparation of Lactobionolactone Derivative (7)

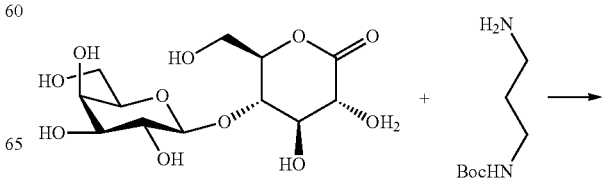

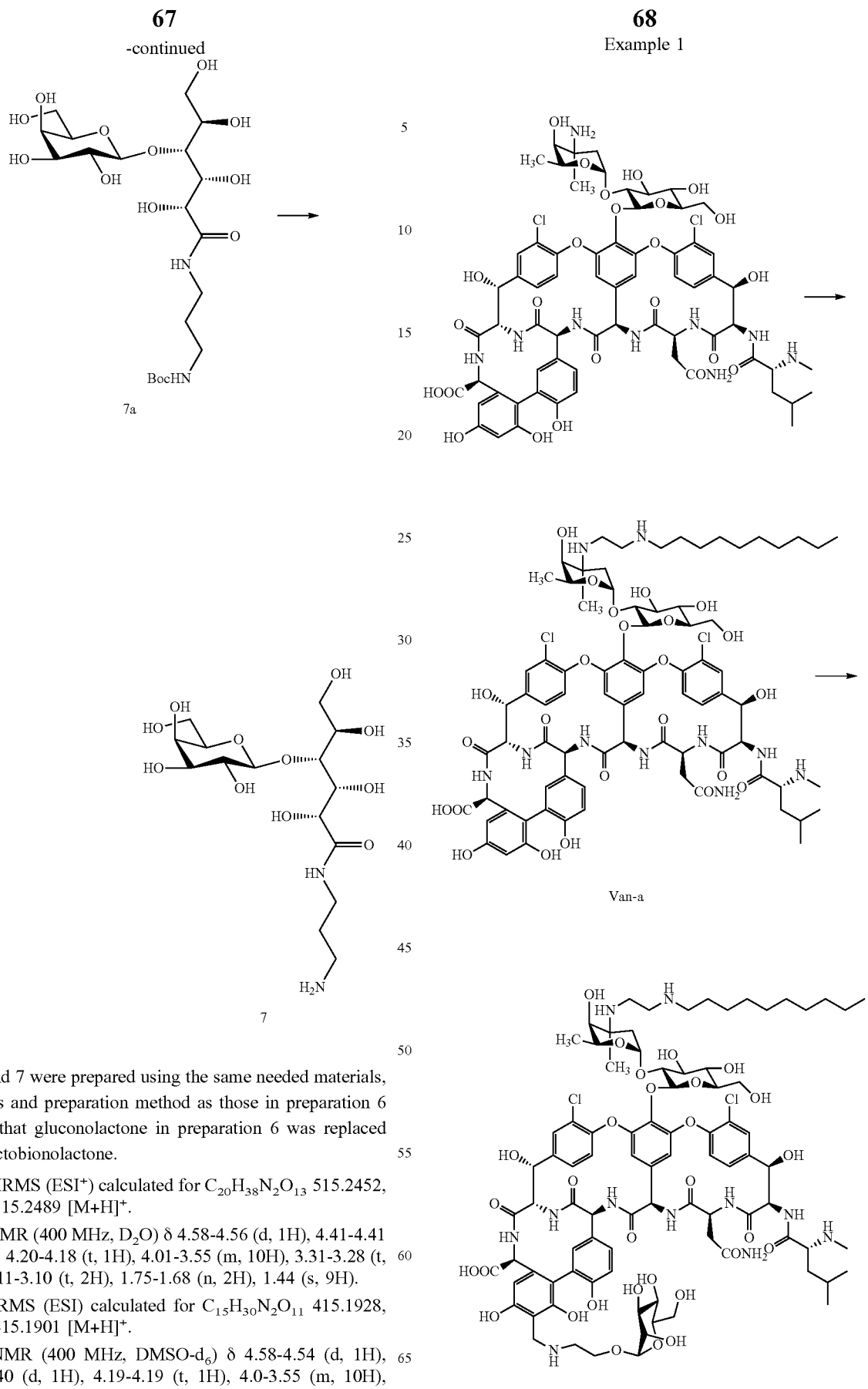

Example 1

7a and 7 were prepared using the same needed materials, reagents and preparation method as those in preparation 6 except that gluconolactone in preparation 6 was replaced with lactobionolactone.

7a: HRMS (ESI$^+$) calculated for $C_{20}H_{38}N_2O_{13}$ 515.2452, found 515.2489 [M+H]$^+$.

$^1$H NMR (400 MHz, D$_2$O) δ 4.58-4.56 (d, 1H), 4.41-4.41 (d, 1H), 4.20-4.18 (t, 1H), 4.01-3.55 (m, 10H), 3.31-3.28 (t, 2H), 3.11-3.10 (t, 2H), 1.75-1.68 (n, 2H), 1.44 (s, 9H).

7: HRMS (ESI) calculated for $C_{15}H_{30}N_2O_{11}$ 415.1928, found 415.1901 [M+H]$^+$.

$^1$H NMR (400 MHz, DMSO-d$_6$) δ 4.58-4.54 (d, 1H), 4.41-4.40 (d, 1H), 4.19-4.19 (t, 1H), 4.0-3.55 (m, 10H), 3.36-3.4 (t, 2H), 3.28-3.30 (t, 2H), 1.69-1.73 (m, 2H).

Step 1: Commercially available vancomycin (950 mg), N-decyl-N-Fmoc-aminoacetaldehyde 1 (550 mg), DIPEA (0.65 mL), 40 mL of DMF were mixed and stirred at room temperature for 1 h until the solution becomes clear. The mixture was stirred for another 1 h, then added with NaCNBH$_3$ (80 mg), 10 mL of methanol, 0.25 mL of TFA at room temperature and stirred for 60 min. The reaction mixture was added with diethyl ether (500 mL) to generate precipitates and filtered. The filtered cake was washed with diethyl ether (300 mL) and then with water (300 mL), and dried to give N-decyl-N-Fmoc-aminoethyl-vancomycin (700 mg) as a white solid. HPLC: C18 column (5 μm, 4.6×250 mm), UV detection at 214 nm, elution conditions: a gradient of 0-90% acetonitrile containing 0.1% v/v TFA over 30 min, retention time ($t_R$)=22.5 min, purity 95%. MS(ESI$^+$): 927.7 [M+2H]$^{2+}$.

N-decyl-N-Fmoc-aminoethyl-vancomycin (550 mg) and a 20% solution (10 mL) of piperidine in DMF was mixed and stirred at room temperature for 30 min. 200 mL of diethyl ether was added to generate precipitates and filtered. The filtered cake was washed with diethyl ether (300 mL) and dried to give N$^{van}$-2-(n-decylamino)ethyl-vancomycin Van-a (450 mg) as a white solid. HPLC: C18 column (5 μm, 4.6×250 mm), UV detection at 214 and 280 nm, elution conditions: a gradient of 0-90% acetonitrile containing 0.1% v/v TFA over 30 min, retention time ($t_R$)=16.3 min, purity 96%. HRMS (ESI$^+$) calculated for $C_{78}H_{100}Cl_2N_{10}O_{24}$ 1630.6289, found 816.3212 [M+2H]$^{2+}$.

Step 2: 2-aminoethyl-α-D-mannopyranoside 2 (30 mg) was dissolved in a mixture of water (100 μL) and acetonitrile (500 μL), added with 30 μL of DIPEA, stirred at room temperature until the solid was completely dissolved (10 min). The mixture was added with 2 μL of a formaldehyde solution (37 wt %), stirred at room temperature for 15 min, and then cooled to −10° C. and stirred for another 5 min. The reaction mixture was quickly mixed with 1.5 mL of a 80% solution of N$^{van}$-2-(n-decylamine)ethyl-vancomycin Van-a (25 mg) in acetonitrile, added with 30 μL of DIPEA, and stirred for 8 h at −10° C. The reaction was monitored by HPLC. HPLC: C18 column (5 μm, 4.6×250 mm), UV detection at 214 nm, elution conditions: a gradient of 2-90% acetonitrile containing 0.1% v/v TFA over 30 min. The crude was purified by reverse-phase C18 HPLC, and lyophilized to give Van001 (15 mg) as a white solid. HRMS (ESI$^+$) calculated for $C_{87}H_{117}Cl_2N_{11}O_{30}$ [M+3H]$^{3+}$ 1865.7345, found 622.9193.

$^1$H NMR (600 MHz, DMSO-d$_6$) δ 7.79 (d, J=1.9 Hz, 1H), 7.49 (d, J=8.6 Hz, 1H), 7.46-7.43 (m, 1H), 7.41 (t, J=7.9 Hz, 1H), 7.28 (dd, J=8.2, 2.3 Hz, 2H), 7.25 (t, J=7.4 Hz, 1H), 7.20 (d, J=8.4 Hz, 1H), 7.13-7.10 (m, 1H), 6.84 (s, 1H), 6.77 (d, J=8.6 Hz, 1H), 6.51 (s, 1H), 5.71 (s, 1H). 5.66 (s, 1H), 5.28 (d, J=7.7 Hz, 1H), 5.24 (s, 1H), 5.14-5.10 (m, 2H), 5.10-5.07 (m, 1H), 4.81 (s, 1H), 4.65-4.60 (m, 2H), 4.46-4.42 (m, 1H), 4.40 (s, 1H), 4.13-4.06 (m, 3H), 3.84-3.80 (m, 1H), 3.68-3.62 (m, 4H), 3.54 (t, J=8.5 Hz, 3H), 3.44-3.40 (m, 4H), 3.38 (t, J=9.4 Hz, 2H), 3.33 (ddd, J=9.5, 6.2, 2.2 Hz, 2H), 3.25 (d, J=6.4 Hz, 3H), 2.85-2.76 (m, 3H), 2.60 (d, J=3.6 Hz, 1H), 2.54 (s, 2H), 2.37 (d, J=3.2 Hz, 1H), 2.11 (dd, J=16.3, 9.1 Hz, 2H), 1.75 (d, J=19.3 Hz, 2H), 1.67-1.59 (m, 3H), 1.49 (dt, J=14.6, 7.7 Hz, 4H), 1.23 (d, J=9.7 Hz, 16H), 1.06 (d, J=6.3 Hz, 3H), 0.90 (d, J=6.2 Hz, 3H), 0.84 (q, J=6.8 Hz, 6H).

Example 2

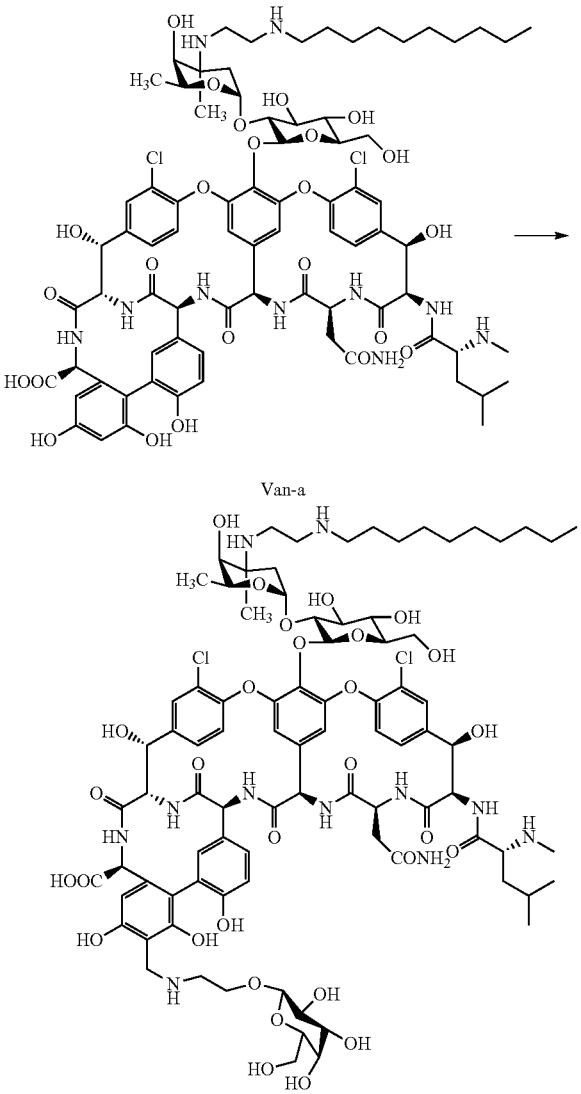

Van002 was prepared using the same needed materials, reagents and preparation method as those in example 1 except that 2-aminoethyl-α-D-mannopyranoside 2 in example 1 was replaced with 2-aminoethyl-β-D-galactopyranoside 4. HRMS (ESI) calculated for $C_{87}H_{117}Cl_2N_{11}O_{30}$ [M+3H]$^{3+}$ 1865.7345, found 622.9193.

$^1$H NMR (600 MHz, DMSO-d$_6$) δ 7.80-7.77 (m, 1H), 7.49 (d, J=8.5 Hz, 1H), 7.46-7.43 (m, 1H), 7.41 (t, J=7.9 Hz, 1H), 7.28 (dd, J=8.1, 3.5 Hz, 2H), 7.27-7.23 (m, 1H), 7.19 (d, J=8.4 Hz, 1H), 7.13-7.11 (m, 1H), 6.84 (d, J=8.5 Hz, 1H), 6.77 (d, J=8.5 Hz, 1H), 6.52-6.49 (m, 1H), 5.66 (s, 1H), 5.27 (d, J=7.6 Hz, 1H), 5.24 (s, 1H), 5.11 (d, J=7.5 Hz, 2H), 5.09 (s, 1H), 4.83-4.79 (m, 1H), 4.77-4.75 (m, 1H), 4.63 (d, J=7.1 Hz, 1H), 4.44 (s, 1H), 4.40-4.38 (m, 11-1), 4.11 (s, 3H), 3.95 (s, 2H), 3.81 (t, J=15.8 Hz, 3H), 3.65 (d, J=10.7 Hz, 1H), 3.62-3.60 (m, 1H), 3.42-3.40 (m, 2H), 3.37 (d, J=5.9 Hz, 3H), 3.33-3.23 (m, 5H), 3.07 (d, J=21.7 Hz, 3H), 2.85-2.77 (m, 3H), 2.56-2.52 (m, 2H), 2.37 (d, J=3.4 Hz, 1H), 2.15-2.07 (m, 2H), 1.80-1.72 (m, 21-1), 1.67-1.59 (m, 3H), 1.53-1.43 (m, 4H), 1.23 (d, J=9.7 Hz, 16H), 1.10-1.03 (m, 3H), 0.90 (d, J=6.1 Hz, 3H), 0.83 (q, J=6.8 Hz, 6H).

Example 3

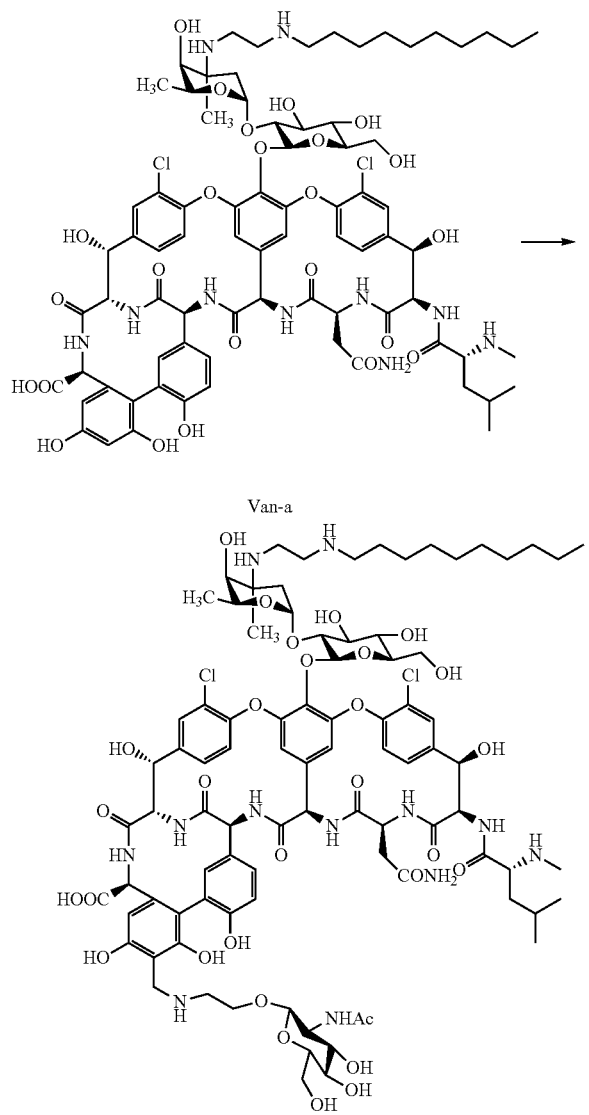

Van003 was prepared using the same needed materials, reagents and preparation method as those in example 1 except that 2-aminoethyl-α-D-mannopyranoside 2 in example 1 was replaced with 2-aminoethyl-2-acetamido-2-deoxy-β-D-glucopyranoside 5. HRMS (ESI+) calculated for $C_{89}H_{120}Cl_2N_{12}O_{30}$ [M+3H]$^{3+}$ 1906.7610, found 636.5398.

$^1$H NMR (600 MHz, DMSO-$d_6$) δ 7.80 (d, J=5.1 Hz, 1H), 7.50-7.44 (m, 3H). 7.29 (dd, J=13.6, 8.0 Hz, 2H), 7.22 (d, J=8.3 Hz, 1H), 7.11 (s, 1H), 6.84 (dd, J=8.4, 2.0 Hz, 1H), 6.77 (d, J=8.7 Hz, 1H), 6.51 (s, 1H), 5.64 (d, J=32.6 Hz, 2H), 5.23 (dd, J=15.8, 5.7 Hz, 2H), 5.11 (s, 2H), 4.65 (q, J=6.6 Hz, 1H), 4.42 (d, J=17.0 Hz, 2H), 4.34 (d, J=8.5 Hz, 1H), 4.11 (q, J=11.5, 9.6 Hz, 3H), 3.92-3.80 (m, 3H), 3.74-3.69 (m, 2H), 3.65 (d, J=10.9 Hz, 2H), 3.43 (td, J=8.2, 3.2 Hz, 5H), 3.37 (s, 4H), 3.29 (d, J=9.4 Hz, 1H), 3.27-3.24 (m, 2H), 3.23 (d, J=8.8 Hz, 1H), 3.18-3.14 (m, 3H), 3.07-3.04 (m, 2H), 3.02-2.98 (m, 2H), 2.88 (dd, J=9.4, 6.4 Hz, 2H), 2.73 (q, J=7.0, 6.3 Hz, 1H), 2.36 (s, 3H), 1.78 (s, 3H), 1.71 (d, J=13.0 Hz, 1H), 1.54 (dt, J=18.6, 6.1 Hz, 4H), 1.23 (d, J=22.5 Hz, 16H), 1.04 (d, J=6.3 Hz, 3H), 0.87 (d, J=6.2 Hz, 3H), 0.83 (t, J=6.8 Hz, 6H).

Example 4

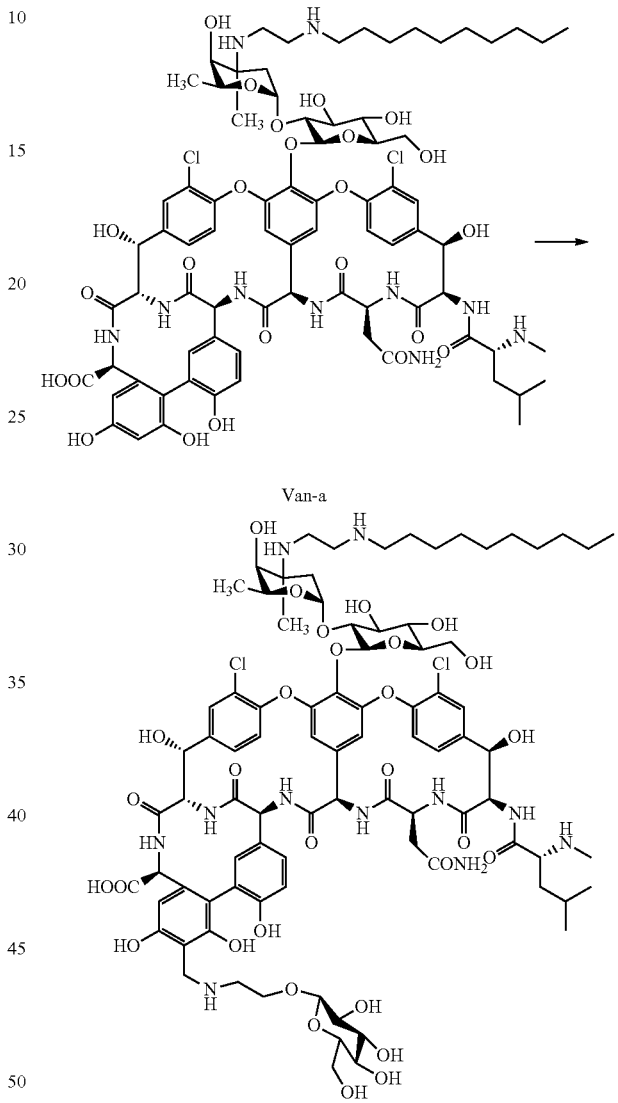

Van004 was prepared using the same needed materials, reagents and preparation method as those in example 1 except that 2-aminoethyl-α-D-mannopyranoside 2 in example 1 was replaced with 2-aminoethyl-β-D-galactopyranoside 4. HRMS (ESI±) calculated for $C_{87}H_{117}Cl_2N_{11}O_{30}$ [M+3H]$^{3+}$ 1865.7345, found 622.9195.

$^1$H NMR (600 MHz, DMSO-$d_6$) δ 7.80-7.77 (m, 1H), 7.49 (d, J=8.5 Hz, 1H), 7.46-7.43 (m, 1H), 7.41 (t, J=7.9 Hz, 1H), 7.28 (dd, J=8.1, 3.5 Hz, 2H), 7.27-7.23 (m, 1H), 7.19 (d, J=8.4 Hz, 1H), 7.13-7.11 (m, 1H), 6.84 (d, J=8.5 Hz, 1H), 6.77 (d, J=8.5 Hz, 1H), 6.52-6.49 (m, 1H), 5.66 (s, 1H), 5.27 (d, J=7.6 Hz, 1H), 5.24 (s, 1H), 5.11 (d, J=7.5 Hz, 2H), 5.09 (s, 1H), 4.83-4.79 (m, 1H), 4.77-4.75 (m, 1H), 4.63 (d, J=7.1 Hz, 1H), 4.44 (s, 1H), 4.40-4.38 (m, 1H), 4.11 (s, 3H), 3.95 (s, 2H), 3.81 (t, J=15.8 Hz, 3H), 3.65 (d, J=10.7 Hz, 1H), 3.62-3.60 (m, 1H), 3.42-3.40 (m, 2H), 3.37 (d, J=5.9 Hz, 3H), 3.33-3.23 (m, 5H), 3.07 (d, J=21.7 Hz, 3H), 2.85-2.77 (m, 3H), 2.56-2.52 (m, 2H). 2.37 (d, J=3.4 Hz, 1H), 2.15-2.07 (m, 2H), 1.80-1.72 (m, 2H), 1.67-1.59 (m, 3H), 1.53-1.43 (m, 4H), 1.23 (d, J=9.7 Hz, 16H), 1.10-1.03 (m, 3H), 0.90 (d, J=6.1 Hz, 3H), 0.83 (q, J=6.8 Hz, 6H).

1.43-1.37 (m, 2H), 1.28-1.18 (m, 16H), 1.04 (d, J=6.3 Hz, 3H), 0.88 (d, J=6.2 Hz, 3H), 0.85-0.81 (m, 6H).

Example 5

Example 6

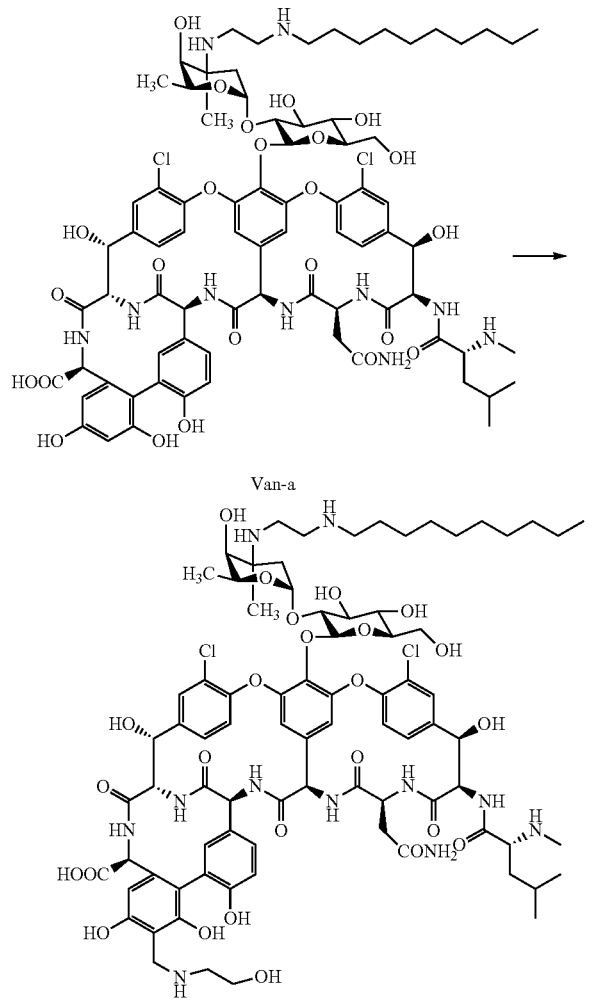

Van005 was prepared using the same needed materials, reagents and preparation method as those in example 1 except that 2-aminoethyl-α-D-mannopyranoside 2 in example 1 was replaced with ethanolamine. HRMS (ESI$^+$) calculated for $C_{81}H_{107}Cl_2N_{11}O_{25}$ [M+3H]$^{3+}$ 1703.6817, found 568.8805.

$^1$H NMR (600 MHz, DMSO-d$_6$) δ 7.79 (d, J=2.0 Hz, 1H), 7.48 (d, J=8.7 Hz, 1H), 7.45 (dd, J=8.3, 1.8 Hz, 1H), 7.30 (d, J=8.4 Hz, 1H), 7.22 (d, J=8.3 Hz, 1H), 7.11-7.09 (m, 1H), 6.84 (dd, J=8.5, 1.9 Hz, 1H), 6.77 (d, J=8.5 Hz, 1H), 6.53 (s, 1H), 5.70-5.61 (m, 3H), 5.23 (dd, J=12.6, 5.9 Hz, 2H), 5.11 (s, 3H), 4.65 (q, J=6.7 Hz, 1H), 4.43 (dd, J=14.7, 5.6 Hz, 2H), 4.12 (dd, J=22.2, 13.0 Hz, 4H), 3.65 (q, J=4.9, 4.1 Hz, 3H), 3.55-3.50 (m, 4H), 3.42 (t, J=5.8 Hz, 3H), 3.28-3.21 (m, 3H), 3.15 (s, 1H), 2.96 (d, J=6.4, 4.6 Hz, 3H), 2.90 (t, J=7.9 Hz, 3H), 2.14-2.08 (m, 21-1), 1.90-1.86 (m, 1H), 1.71 (d, J=13.1 Hz, 1H), 1.56 (dh, J=12.5, 6.9, 6.5 Hz, 5H),

Van006 was prepared using the same needed materials, reagents and preparation method as those in example 1 except that 2-aminoethyl-α-D-mannopyranoside 2 in example 1 was replaced with 2-deoxy-2-aminomannose. HRMS (ESI$^+$) calculated for $C_{85}H_{113}Cl_2N_{11}O_{29}$ [M+3H]$^{3+}$ 1821.7083, found 608.2428.

$^1$H NMR (600 MHz, DMSO-d$_6$) δ 7.79 (d, J=4.9 Hz, 1H), 7.49 (s, 1H), 7.48-7.44 (m, 2H), 7.31 (d, J=8.0 Hz, 1H), 7.22-7.20 (m, 1H). 7.11 (s, 1H), 6.84 (s, 1H), 6.77 (dd, J=8.6, 2.9 Hz, 1H), 6.54-6.52 (m, 1H), 5.70-5.67 (m, 1H), 5.63 (s, 1H), 5.48-5.46 (m, 1H), 5.25 (d, J=7.6 Hz, 1H), 5.22 (d, J=4.0 Hz, 1H), 5.10 (d, J=5.5 Hz, 3H), 4.65 (d, J=6.5 Hz, 2H), 4.47-4.44 (m, 1H), 4.41 (d, J=5.6 Hz, 1H), 4.26-4.24 (m, 1H), 4.10 (s, 2H), 3.69 (d, J=9.7 Hz, 1H), 3.67-3.64 (m, 2H), 3.59 (td, J=8.6, 6.9, 3.5 Hz, 3H), 3.54-3.50 (m, 4H), 3.43-3.40 (m, 3H), 3.28-3.21 (m, 4H), 3.17-3.11 (m, 4H), 2.92-2.88 (m, 3H), 2.60 (s, 1H), 2.38-2.36 (m, 1H), 2.16-2.10 (m, 2H), 1.90-1.87 (m, 1H), 1.72-1.69 (m, 1H), 1.58-

1.53 (m, 4H), 1.23 (d, J=9.0 Hz, 16H), 1.04 (d, J=6.4 Hz, 3H), 0.89 (d, J=6.2 Hz, 3H), 0.85-0.83 (m, 4H).

Example 7

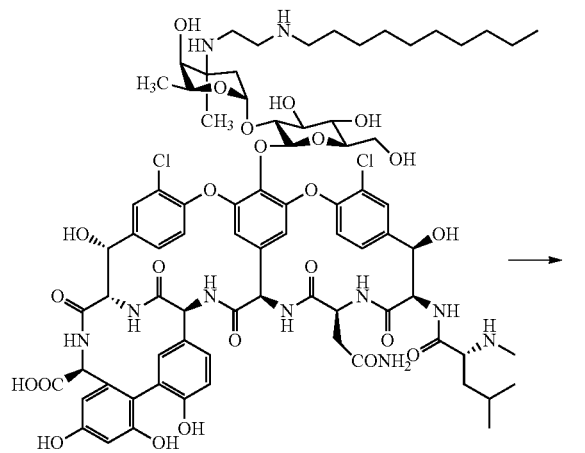

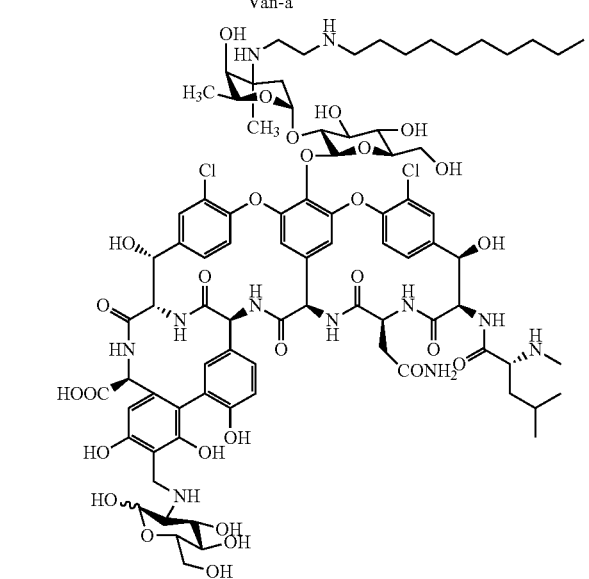

Van007 was prepared using the same needed materials, reagents and preparation method as those in example 1 except that 2-aminoethyl-α-D-mannopyranoside 2 in example 1 was replaced with 2-deoxy-2-aminoglucose. HRMS (ESI$^+$) calculated for $C_{85}H_{113}Cl_2N_{11}O_{29}$ [M+3H]$^{3+}$ 1821.7083, found 608.2418.

$^1$H NMR (600 MHz, DMSO-d$_6$) δ 7.79 (d, J=4.9 Hz, 1H), 7.49 (s, 1H), 7.48-7.44 (m, 2H), 7.31 (d, J=8.0 Hz, 1H), 7.22-7.20 (m, 1H), 7.11 (s, 1H), 6.84 (s, 1H), 6.77 (dd, J=8.6, 2.9 Hz, 1H), 6.54-6.52 (m, 1H), 5.70-5.67 (m, 1H), 5.63 (s, 1H), 5.48-5.46 (m, 1H), 5.25 (d, J=7.6 Hz, 1H), 5.22 (d, J=4.0 Hz, 1H), 5.10 (d, J=5.5 Hz, 3H), 4.65 (d, J=6.5 Hz, 2H), 4.47-4.44 (m, 1H), 4.41 (d, J=5.6 Hz, 1H), 4.26-4.24 (m, 1H), 4.10 (s, 2H), 3.69 (d, J=9.7 Hz, 1H), 3.67-3.64 (m, 2H), 3.59 (td, J=8.6, 6.9, 3.5 Hz, 3H), 3.54-3.50 (m, 4H), 3.43-3.40 (m, 3H), 3.28-3.21 (m, 4H), 3.17-3.11 (m, 4H), 2.92-2.88 (m, 3H), 2.60 (s, 1H), 2.38-2.36 (m, 1H), 2.16-2.10 (m, 2H), 1.90-1.87 (m, 1H), 1.72-1.69 (m, 1H), 1.58-

1.53 (m, 4H), 1.23 (d, J=9.0 Hz, 16H), 1.04 (d, J=6.4 Hz, 3H), 0.89 (d, J=6.2 Hz, 3H), 0.85-0.83 (m, 4H).

Example 8

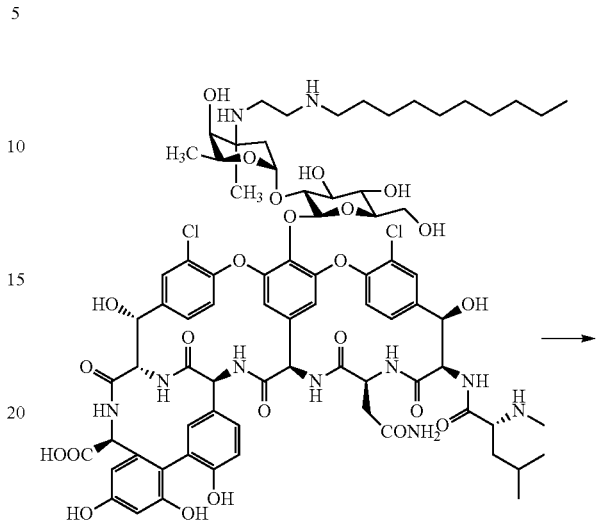

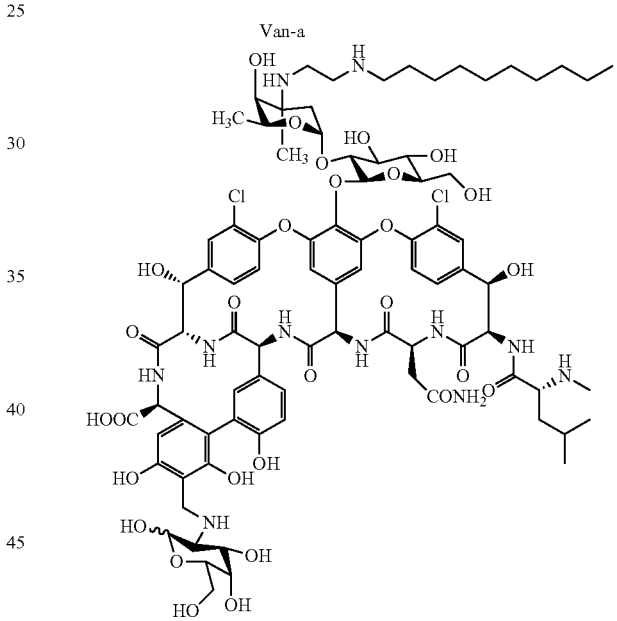

Van008 was prepared using the same needed materials, reagents and preparation method as those in example 1 except that 2-aminoethyl-α-D-mannopyranoside 2 in example 1 was replaced with 2-deoxy-2-aminogalactose. HRMS (ESI$^+$) calculated for $C_{85}H_{113}Cl_2N_{11}O_{29}$ [M+3H]$^{3+}$ 1821.7083, found 911.8666 [M+2H]$^{2+}$ 608.2418.

$^1$H NMR (600 MHz, DMSO-d$_6$) δ 7.79 (d, J=4.9 Hz, 1H), 7.49 (s, 1H), 7.48-7.44 (m, 2H), 7.31 (d, J=8.0 Hz, 1H), 7.22-7.20 (m, 1H), 7.11 (s, 1H), 6.84 (s, 1H), 6.77 (dd, J=8.6, 2.9 Hz, 1H), 6.54-6.52 (m, 1H), 5.70-5.67 (m, 1H), 5.63 (s, 1H), 5.48-5.46 (m, 1H), 5.25 (d, J=7.6 Hz, 1H), 5.22 (d, J=4.0 Hz, 1H), 5.10 (d, J=5.5 Hz, 3H), 4.65 (d, J=6.5 Hz, 2H), 4.47-4.44 (m, 1H), 4.41 (d, J=5.6 Hz, 1H), 4.26-4.24 (m, 1H), 4.10 (s, 2H), 3.69 (d, J=9.7 Hz, 1H), 3.67-3.64 (m, 2H), 3.59 (td, J=8.6, 6.9, 3.5 Hz, 3H), 3.54-3.50 (m, 4H), 3.43-3.40 (m, 3H), 3.28-3.21 (m, 4H), 3.17-3.11 (m, 4H), 2.92-2.88 (m, 3H), 2.60 (s, 1H), 2.38-2.36 (m, 1H), 2.16-2.10 (m, 2H), 1.90-1.87 (m, 1H), 1.72-1.69 (m, 1H), 1.58-

1.53 (m, 4H), 1.23 (d, J=9.0 Hz, 16H), 1.04 (d, J=6.4 Hz, 3H), 0.89 (d, J=6.2 Hz, 3H), 0.85-0.83 (m, 4H).

Example 9

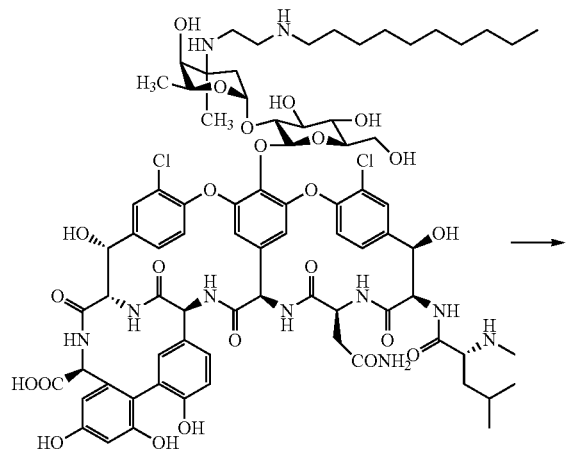

Van009 was prepared using the same needed materials, reagents and preparation method as those in example 1 except that 2-aminoethyl-α-D-mannopyranoside 2 in example 1 was replaced with the gluconolactone derivative 6. HRMS (ESI$^+$) calculated for $C_{88}H_{120}Cl_2N_{12}O_{30}$ [M+2H]$^{2+}$ 1894.7610, found 948.3892.

$^1$H NMR (600 MHz, DMSO-d$_6$) δ 7.79 (s, 1H), 7.50-7.47 (m, 1H), 7.45 (dd, J=8.3, 1.8 Hz, 1H), 7.30 (d, J=8.3 Hz, 1H), 7.20 (d, J=8.4 Hz, 1H), 7.10 (s, 1H), 6.84 (dd, J=8.5, 2.0 Hz, 1H), 6.77 (d, J=8.5 Hz, 1H), 6.53 (s, 1H), 5.70 (d, J=21.8 Hz, 2H), 5.29-5.25 (m, 2H), 5.12 (d, J=5.1 Hz, 2H), 5.08 (d, J=2.0 Hz, 1H), 4.80 (s, 1H), 4.65 (d, J=7.1 Hz, 1H), 4.44 (d, J=5.2 Hz, 1H), 4.41 (d, J=6.0 Hz, 1H), 4.09 (d, J=8.4 Hz, 1H), 4.06 (s, 2H), 4.00 (d, J=3.6 Hz, 1H), 3.89 (t, J=2.9 Hz, 1H), 3.65 (d, J=10.7 Hz, 2H), 3.56 (d, J=2.7 Hz, 1H), 3.54 (d, J=2.4 Hz, 2H), 3.37 (d, J=5.3 Hz, 1H), 3.35 (d, J=4.9 Hz, 1H), 3.25 (d, J=5.3 Hz, 3H), 3.16 (ddt, J=19.9, 13.0, 6.6 Hz, 5H), 2.92 (t, J=7.9 Hz, 4H), 2.61-2.59 (m, 1H), 2.56 (s, 2H), 2.50 (d, J=2.0 Hz, 1H), 2.38-2.36 (m, 1H), 2.12-2.05 (m, 2H), 1.95-1.88 (m, 2H), 1.82 (dq, J=14.5, 7.2 Hz, 3H), 1.67-1.60 (m, 3H), 1.51 (t, J=7.8 Hz, 3H), 1.34 (s, 2H), 1.24 (d, J=14.1 Hz, 14H), 1.08 (d, J=6.1 Hz, 3H), 0.90 (d, J=6.0 Hz, 3H), 0.86-0.84 (m, 3H), 0.83 (s, 1H).

Example 10

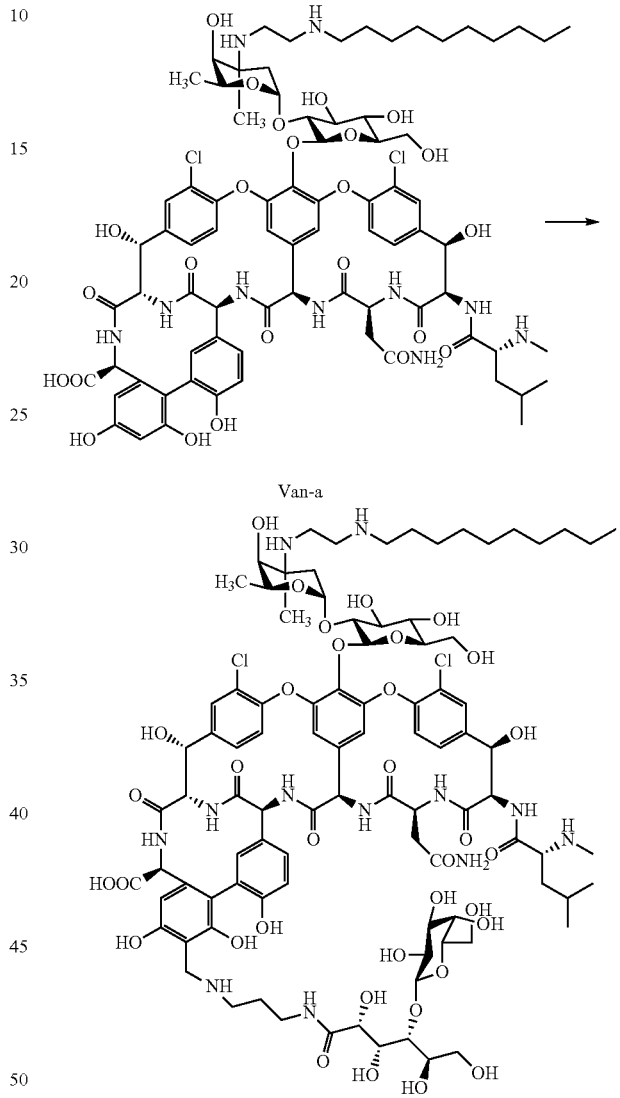

Van010 was prepared using the same needed materials, reagents and preparation method as those in example 1 except that 2-aminoethyl-α-D-mannopyranoside 2 in example 1 was replaced with the lactobionolactone derivative 7. HRMS (ESI$^+$) calculated for $C_{94}H_{130}Cl_2N_{12}O_{35}$ [M+2H]$^{2+}$ 2056.8139, found 1029.4148.

$^1$H NMR (600 MHz, DMSO-d$_6$) δ 7.79 (s, 1H), 7.49 (d, J=8.6 Hz, 1H), 7.45 (d, J=9.1 Hz, 1H), 7.30 (d, J=8.3 Hz, 1H), 7.20 (d, J=8.4 Hz, 1H), 7.10 (s, 1H), 6.85-6.83 (m, 1H). 6.77 (d, J=8.5 Hz, 1H), 6.53 (s, 1H), 5.72 (d, J=7.3 Hz, 1H), 5.68 (s, 1H), 5.29 (s, 1H), 5.27 (d, J=7.6 Hz, 1H), 5.11 (s, 2H), 5.08 (s, 1H), 4.80 (s, 1H), 4.65 (d, J=6.5 Hz, 1H), 4.45 (s, 1H), 4.41 (d, J=5.7 Hz, 1H), 4.27 (d, J=7.0 Hz, 1H), 4.11 (d, J=2.3 Hz, 1H), 4.07-4.05 (m, 2H), 4.01-3.99 (m, 2H), 3.90-3.88 (m, 1H), 3.69-3.66 (m. 3H), 3.65 (s, 1H), 3.60-

3.59 (m, 1H), 3.58 (d, J=3.6 Hz, 1H), 3.55 (d, J=8.0 Hz, 2H), 3.52 (d, J=5.2 Hz, 2H), 3.50 (d, J=4.4 Hz, 1H), 3.49-3.47 (m, 2H), 3.39 (t, J=6.4 Hz, 2H), 3.30 (d, J=2.2 Hz, 1H), 3.26 (d, J=3.3 Hz, 3H), 3.19-3.11 (m, 6H), 3.05-3.01 (m, 2H), 2.92 (t, J=7.6 Hz, 4H), 2.61-2.59 (m, 1H). 2.56 (s, 21-1), 2.51 (d, J=1.9 Hz, 1H), 2.38-2.36 (m, 1H), 2.04 (s, 1H), 1.93 (s, 2H), 1.85-1.79 (m, 4H), 1.52 (s, 4H), 1.34 (s, 3H), 1.24 (d, J=15.3 Hz, 16H), 1.09 (d, J=6.2 Hz, 3H), 0.91 (d, J=6.0 Hz, 3H), 0.86-0.84 (m, 3H), 0.84 (s, 1H).

Example 11

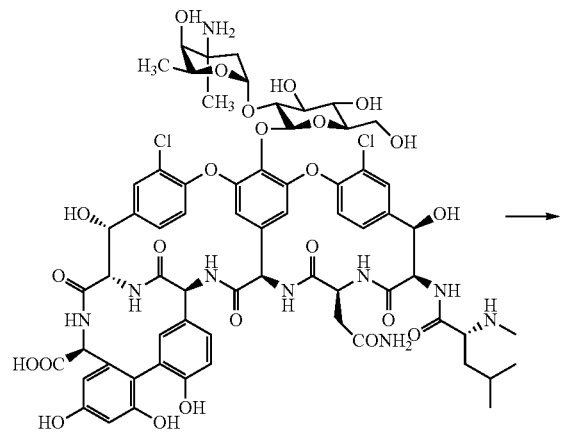

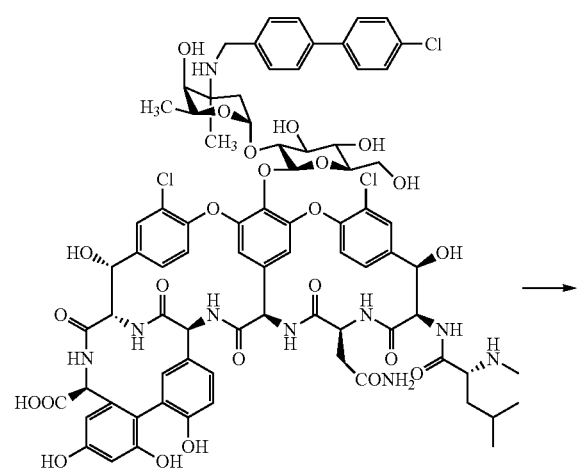

Van-b

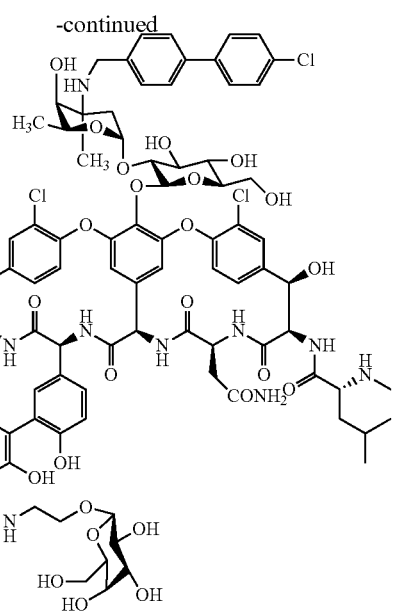

Step 1: commercially available vancomycin (100 mg) and DIPEA (30 μL) were dissolved in 3 mL of DMF to give a turbid solution, which was heated to 50° C. to become clear. 4'-chlorobiphenyl-4-carboxaldehyde (30 mg) was added, heated and stirred for 4 h. (Aromatic aldehyde has a low reactivity, and therefore, it is necessary to prolong the reaction time and heat up to accelerate the reaction rate. Vancomycin does not have a good solubility in DMF, and the added DIPEA may enhance the dissolution. If there are insolubles, the reaction rate would be affected.) NaCNBH$_3$ (8 mg), 1 mL of methanol and 30 μL of TFA were added at room temperature and stirred overnight. The reaction was monitored by HPLC. Diethyl ether (50 mL) was added to generate precipitates and filtered to give a crude, which was purified by reverse-phase C18 HPLC and lyophilized to give Van-b (60 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for $C_{79}H_{84}C_3N_9O_{24}$ [M+2H]$^{2+}$ 1647.4695, found 824.7489.

Step 2: 2-aminoethyl-β-D-galactopyranoside 4 (30 mg) was dissolved in a mixture of water (1004) and acetonitrile (500 μL), added with 30 μL of DIPEA, and stirred at room temperature until the solid was completely dissolved (10 min). The mixture was added with 2 μL of a 37 wt % formaldehyde solution, stirred at room temperature for 15 min, and then cooled to −10° C. and stirred for 5 min. The reaction mixture was quickly mixed with 1.5 mL of a 80% solution of N$^{van}$-2-(4'-chlorobiphenylmethyl)-vancomycin (Van-b) (25 mg) and DIPEA (30 μL) in acetonitrile, stirred for 8 h at −10° C. HPLC monitoring (0.1% v/v TFA was separately incorporated in H$_2$O and acetonitrile, 2-90%, 30 min) showed that the reaction is complete. The crude was purified by reverse-phase C18 HPLC and worked-up to give Van011. HRMS (ESI$^+$) calculated for $C_{87}H_{117}Cl_2N_{11}O_{30}$ [M+3H]$^{3+}$ 1882.5751, found 628.5331.

$^1$H NMR (600 MHz, DMSO-d$_6$) δ 7.82 (d, J=2.0 Hz, 1H), 7.74-7.70 (m, 4H), 7.69 (s. 1H), 7.56-7.52 (m, 4H), 7.51 (s, 1.1-1), 7.49 (d, J=8.8 Hz, 1H), 7.46 (dd, J=8.3, 1.8 Hz, 1H), 7.31 (d, J=8.4 Hz, 1H), 7.22 (d, J=8.4 Hz, 1H), 7.12 (s, 1H), 6.84 (d, J=8.5 Hz, 1H), 6.77 (d, J=8.6 Hz, 1H), 6.51 (s, 1H), 5.72 (s, 1H), 5.69 (s, 1H), 5.34 (d, J=7.7 Hz, 1H), 5.29-5.27

(m, 1H), 5.11 (d, J=10.2 Hz, 2H), 4.82-4.79 (m, 1H), 4.65 (d, J=6.6 Hz, 1H), 4.46-4.44 (m, 1H), 4.40 (s, 1H), 4.13-4.11 (m, 2H), 4.02 (s, 2H), 3.95 (s, 2H), 3.81-3.77 (m, 1H), 3.66 (d, J=10.6 Hz, 1H), 3.61 (d, J=3.1 Hz, 1H), 3.56 (t, J=8.5 Hz, 1H), 3.50 (ddd, J=12.9, 7.5, 5.1 Hz, 4H), 3.37 (td, J=5.6, 5.1, 3.5 Hz, 4H), 3.31-3.24 (m, 5H), 2.61-2.58 (m, 1H), 2.56-2.52 (m, 2H), 2.37-2.36 (m, 1H), 2.13-2.08 (m, 3H), 1.81 (d, J=13.1 Hz, 2H), 1.68-1.59 (m, 4H), 1.49-1.47 (m, 2H), 1.21 (s, 1H), 1.11 (d, J=6.3 Hz, 3H), 0.90 (d, J=6.3 Hz, 3H), 0.85 (d, J=6.3 Hz, 3H).

(s, 1H), 5.34 (d, J=7.7 Hz, 1H), 5.28 (s, 1H), 5.14 (s, 2H), 5.10 (s, 1H), 4.86 (s, 1H), 4.66 (d, J=6.6 Hz, 1H), 4.43 (s, 1H), 4.41 (s, 1H), 4.28 (s, 1H), 4.16 (s, 1H), 4.02 (s, 1H), 3.67 (d, J=10.7 Hz, 1H), 3.56 (d, J=8.4 Hz, 2H), 3.28-3.24 (m, 3H), 2.67-2.62 (m, 3H), 2.57-2.54 (m, 2H), 2.38-2.36 (m, 1H), 2.09 (d, J=8.4 Hz, 3H), 1.82 (d, J=13.0 Hz. 2H), 1.66-1.61 (m, 3H), 1.48 (s, 2H), 1.11 (d, J=6.2 Hz, 3H), 0.91-0.89 (m, 3H), 0.85 (d, J=6.0 Hz, 3H).

Example 12

Example 13

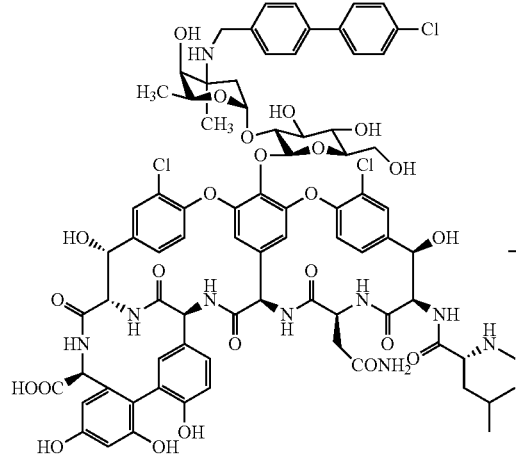

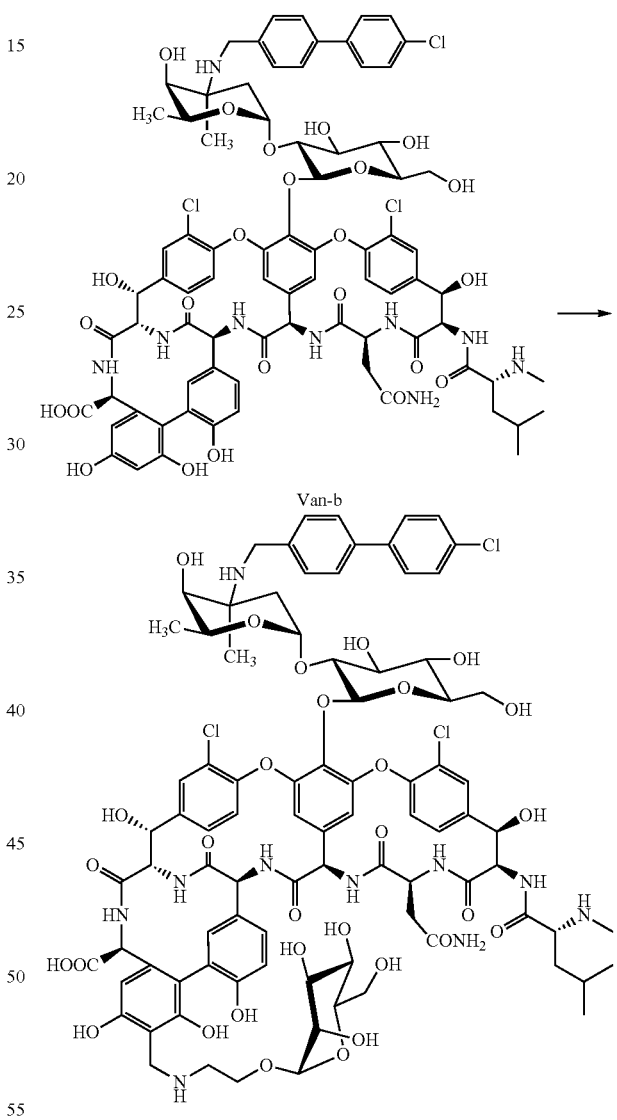

Van012 was prepared using the same needed materials, reagents and preparation method as those in example 11 except that 2-aminoethyl-β-D-galactopyranoside 4 in example 11 was replaced with (aminomethyl)phosphonic acid. HRMS (ESI$^+$) calculated for $C_{81}H_{90}Cl_3N_{10}O_{27}P$ [M+3H]$^{3+}$ 1770.4780, found 591.1677.

$^1$H NMR (600 MHz, DMSO-d$_6$) δ 7.86 (s, 1H), 7.73-7.70 (m, 4H), 7.69 (d, J=2.1 Hz, 1H), 7.56-7.52 (m, 4H), 7.52 (d, J=2.2 Hz, 1H), 7.46 (dd, J=8.4, 1.9 Hz, 2H), 7.31 (s, 1H), 7.21 (d, J=8.4 Hz, 1H), 7.13 (s, 1H), 6.79 (dd, J=8.4, 2.0 Hz, 2H), 6.72 (d, J=8.6 Hz. 2H), 6.44 (s, 1H), 5.75 (s, 1H), 5.63

Van013 was prepared using the same needed materials, reagents and preparation method as those in example 11 except that 2-aminoethyl-β-D-galactopyranoside 4 in example 11 was replaced with 2-aminoethyl-α-D-mannopyranoside 2. HRMS (ESI$^+$) calculated for $C_{88}H_{101}Cl_3N_{10}O_{30}$ [M+2H]$^{2+}$ 1882.5751, found 942.2943.

$^1$H NMR (600 MHz, DMSO-d$_6$) δ 7.83 (d, J=2.0 Hz, 1H), 7.73-7.70 (m. 4H), 7.70 (d, J=2.1 Hz, 1H), 7.56-7.52 (m, 4H), 7.52 (d, J=2.0 Hz, 1H). 7.47-7.44 (m, 2H), 7.30 (d, J=8.3 Hz, 1H), 7.19 (d, J=8.5 Hz, 1H), 6.86 (dd, J=8.5, 2.0 Hz, 1H), 6.77 (d, J=8.5 Hz, 1H), 6.54 (s, 1H), 5.87 (d, J=2.0

Hz, 1H), 5.35 (d, J=7.7 Hz, 1H), 5.30 (d, J=4.2 Hz, 1H), 5.13 (s, 1H), 5.11 (s, 1H), 5.07 (d, J=2.0 Hz, 1H), 4.76 (s, 1H), 4.66 (d, J=6.6 Hz, 1H), 4.64 (d, J=1.7 Hz, 1H), 4.46 (s, 1H), 4.41 (d, J=5.8 Hz, 1H), 4.15 (t, J=13.7 Hz, 3H), 4.10 (s, 1H), 4.03 (s, 2H), 3.95 (t, J=6.5 Hz, 1H), 3.86-3.83 (m, 1H), 3.67 (dd, J=3.5, 1.7 Hz, 1H), 3.66-3.64 (m, 1H), 3.63-3.62 (m, 1H), 3.58 (d, J=8.7 Hz, 1H), 3.51 (d, J=3.3 Hz, 1H), 3.49 (d, J=3.5 Hz, 1H), 3.38 (t, J=9.4 Hz, 3H), 3.34 (dd, J=6.3, 2.2 Hz, 2H), 3.26 (d, J=6.2 Hz, 2H), 3.11 (d, J=6.0 Hz, 2H), 2.73 (d, J=15.5 Hz, 2H), 2.10 (d, J=11.5 Hz, 2H), 1.92-1.89 (m, 2H), 1.82 (d, J=13.1 Hz, 2H), 1.51 (s, 3H), 1.10 (d, J=6.2 Hz, 3H), 0.91 (t, J=6.6 Hz, 6H).

Example 14

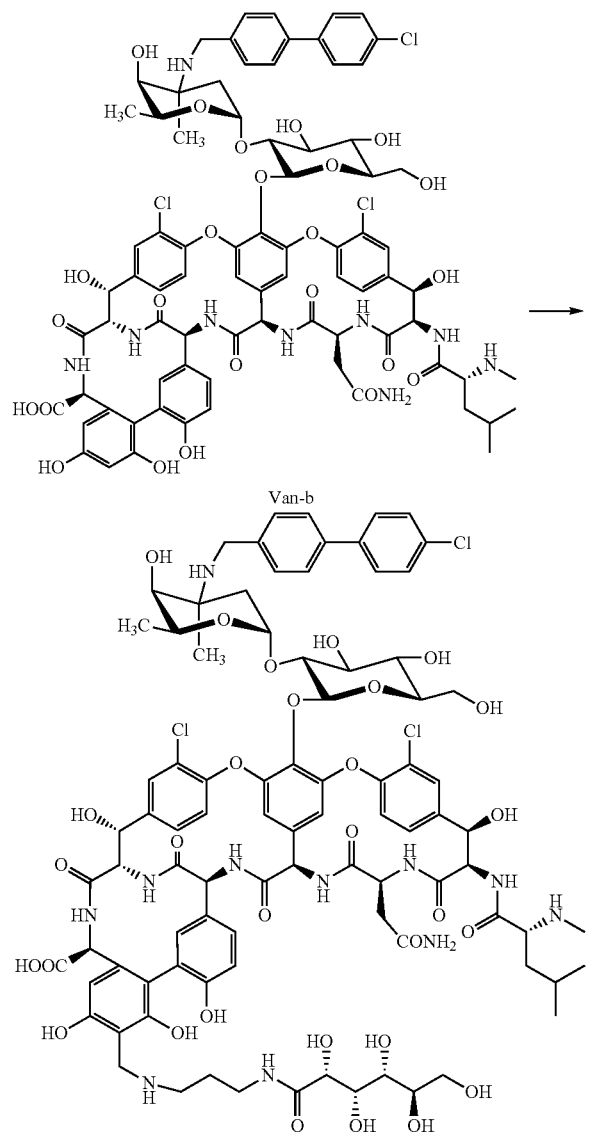

Van014 was prepared using the same needed materials, reagents and preparation method as those in example 11 except that 2-aminoethyl-β-D-galactopyranoside 4 in example 11 was replaced with the gluconolactone derivative 6. HRMS (ESI+) calculated for $C_{89}H_{104}C_{13}N_{11}O_{30}$ [M+2H]$^{2+}$ 1911.6016, found 956.8070.

$^1$H NMR (600 MHz, DMSO-d$_6$) δ 7.82 (s, 1H), 7.74-7.70 (m, 4H), 7.69 (s, 1H), 7.56-7.52 (m, 4H), 7.52 (d, J=1.8 Hz, 1H), 7.50-7.48 (m, 1H), 7.46 (dd, J=8.3, 1.8 Hz, 1H), 7.30 (d, J=8.4 Hz, 1H), 7.22 (d, J=8.4 Hz, 1H), 7.11 (s, 1H), 6.85 (dd, J=8.4, 2.0 Hz, 1H), 6.77 (d, J=8.6 Hz, 1H), 6.52 (s, 1H), 5.71 (d, J=9.9 Hz, 2H), 5.34 (d, J=7.6 Hz, 1H), 5.29 (d, J=4.1 Hz, 1H), 5.12 (d, J=3.8 Hz, 2H), 5.09 (s, 1H), 4.80 (s, 1H), 4.65 (d, J=6.6 Hz, 1H), 4.44 (s, 1H). 4.40 (s, 1H), 4.10 (s, 1H), 4.05 (s, 2H), 4.02 (d, J=6.9 Hz, 2H), 4.00 (d, J=3.6 Hz, 1H), 3.89 (t, J=2.8 Hz, 1H), 3.66 (d, J=10.7 Hz, 2H), 3.58-3.53 (m, 3H), 3.37 (d, J=5.2 Hz, 1H), 3.35-3.34 (m, 1H), 3.28-3.24 (m, 3H), 3.18 (q, J=6.8 Hz, 2H), 3.15-3.12 (m, 2H), 2.91 (s, 3H), 2.55 (s, 2H), 2.10 (d, J=11.2 Hz, 3H), 1.81 (d, J=11.5 Hz, 2H), 1.64 (s, 3H), 1.49 (s, 3H), 1.35 (s, 1H), 1.10 (d, J=6.2 Hz, 3H), 0.91 (d, J=6.2 Hz, 3H), 0.85 (d, J=6.1 Hz, 3H).

Example 15

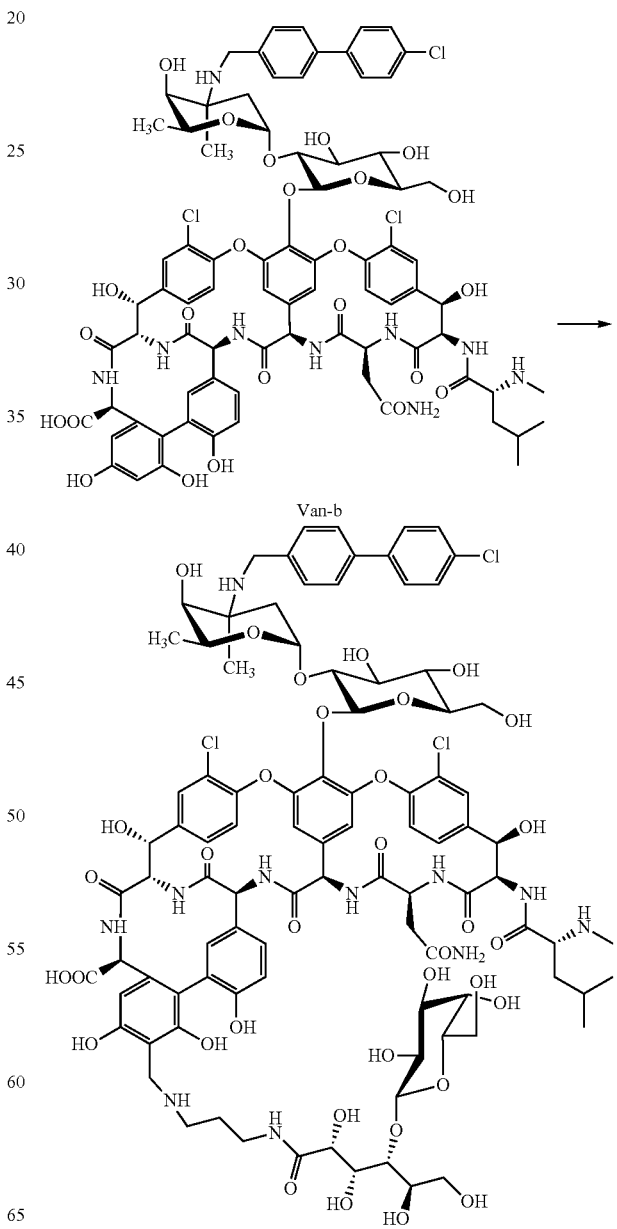

Van015 was prepared using the same needed materials, reagents and preparation method as those in example 11 except that 2-aminoethyl-β-D-galactopyranoside 4 in example 11 was replaced with the lactobionolactone derivative 7. FIRMS (ESI$^+$) calculated for $C_{95}H_{114}C_{13}N_{11}O_{35}$ [M+2H]$^{2+}$ 2073.6544, found 1037.9145.

$^1$H NMR (600 MHz, DMSO-d$_6$) δ 7.82 (d, J=1.9 Hz, 1H), 7.73-7.70 (m, 4H), 7.69 (d, J=2.1 Hz, 1H), 7.56-7.52 (m, 4H), 7.52 (d, J=2.0 Hz, 1H), 7.49 (d, J=8.5 Hz, 1H), 7.47-7.45 (m, 1H), 7.31 (d, J=8.4 Hz, 1H), 7.22 (d, J=8.4 Hz, 1H), 7.10 (s, 1H), 6.85 (dd, J=8.5, 1.8 Hz, 1H), 6.77 (d, J=8.5 Hz, 1H), 6.53 (s, 1H), 5.72 (dd, J=8.5, 4.7 Hz, 2H), 5.34 (d, J=7.6 Hz, 2H), 5.29 (d, J=4.0 Hz, 2H), 5.13 (s, 2H), 5.09 (d, J=1.9 Hz, 1H), 4.81 (s, 2H), 4.66 (t, 1=6.4 Hz, 2H), 4.44 (d, J=5.3 Hz. 1H), 4.41 (d, J=5.7 Hz, 1H). 4.26 (d, J=6.8 Hz, 1H), 4.10 (d, J=2.3 Hz, 2H), 4.06 (s, 2H), 4.02 (d, J=7.5 Hz, 2H), 4.00 (dd, J=4.6, 2.4 Hz, 2H), 3.67 (dq, J=10.3, 6.1 Hz, 4H), 3.59 (d, J=2.7 Hz, 1H), 3.57 (d, J=3.7 Hz, 1H), 3.56 (t, J=3.3 Hz, 1H), 3.52 (d, J=4.8 Hz, 1H), 3.50 (d, J=4.6 Hz, 1H), 3.39 (t, J=6.3 Hz, 2H), 3.32 (d, J=9.5 Hz, 1H), 3.29 (d, J=3.0 Hz, 2H), 3.27 (d, J=6.9 Hz, 1H), 3.25 (s, 1H), 2.92 (t, J=6.6 Hz, 2H), 2.57 (s, 2H), 2.10 (d, J=11.4 Hz, 2H), 2.04 (s, 2H), 1.82 (dd, J=12.9, 6.7 Hz, 3H), 1.65 (d, J=7.4 Hz, 2H), 1.50 (d, J=13.1 Hz, 4H), 1.11 (d, J=6.3 Hz, 3H), 0.91 (d, J=6.1 Hz, 3H), 0.86 (d, J=6.1 Hz, 3H).

Example 16

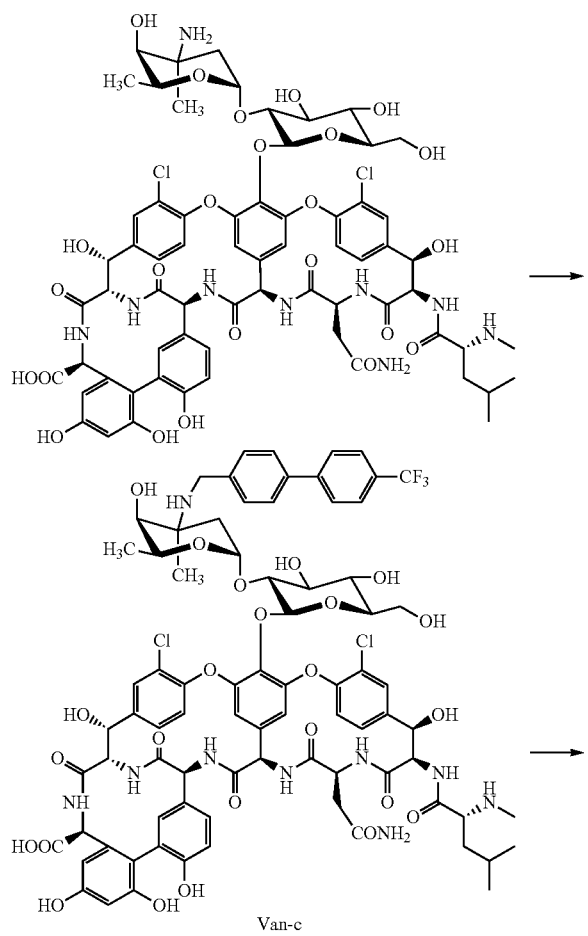

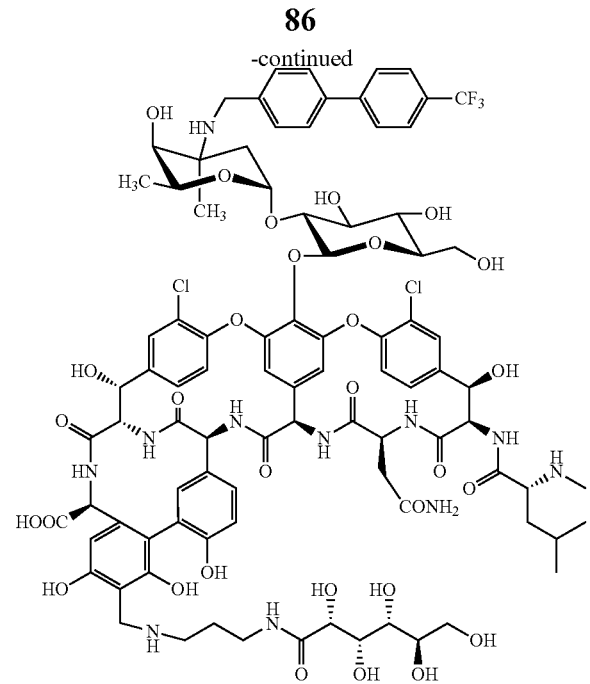

Step 1: commercially available vancomycin (100 mg) and DIPEA (30 µL) were dissolved in 3 mL of DMF, to give a turbid solution, which was heated to 50° C. to become clear. 4'-trifluoromethyl-biphenyl-4-carboxaldehyde (30 mg) was added, and the reaction mixture was heated under stirring for 4 h. Then, NaCNBH$_3$ (8 mg), 1 mL of methanol and 30 µL of TFA were added at room temperature. The reaction was stirred overnight, and monitored by HPLC. The reaction mixture was added with diethyl ether (50 mL) to generate precipitates, which was filtered to give a crude. The crude was purified by reverse-phase C18 HPLC, and lyophilized to give Van-c (40 mg) as a white solid. HPLC: C18 column (5 µm, 4.6×250 mm), UV detection at 214 nm, elution conditions: a gradient of 2-90% acetonitrile containing 0.1% v/v TFA over 30 min. HRMS (ESI$^+$) calculated for $C_{80}H_{84}Cl_2F_3N_9O_{24}$ 1681.4958, found 841.7475 [M+2H]$^{2+}$.

Step 2: 30 µL of DIPEA was added to a mixture of the gluconolactone derivative 6 (40 mg), 500 µL of water and 500 µL of acetonitrile, and stirred at room temperature until the solid was completely dissolved (10 min). The mixture was added with 2 µL of a 37 wt % formaldehyde solution, stirred at room temperature for 15 min, cooled to −10° C. and stirred for 5 min. The mixture was quickly mixed with 1.5 mL of a 80% solution of N$^{van}$-2-(4'-trifluoromethyl-biphenylmethyl)-vancomycin (Van-c) (25 mg) in acetonitrile, added with 30 µL of DIPEA, and stirred at −10° C. for 8 h. The reaction was monitored by HPLC. HPLC: C18 column (5 µm, 4.6×250 mm), UV detection at 214 nm, elution conditions: a gradient of 2-90% acetonitrile containing 0.1% v/v TFA over 30 min. The crude was purified by reverse-phase C18 HPLC and lyophilized to give Van016 (10 mg) as a white solid. HRMS (ESI$^+$) calculated for $C_{90}H_{104}Cl_2F_3N_{11}O_{30}$ [M+2H]$^{2+}$ 1945.6280, found 974.8218.

$^1$H NMR (600 MHz, DMSO-d$_6$) δ 7.91 (s, 1H), 7.89 (s, 1H), 7.82 (d, J=8.2 Hz, 3H), 7.80 (d, J=7.9 Hz, 2H), 7.59 (d, J=8.1 Hz, 2H), 7.50-7.45 (m, 3H), 7.31 (d, J=8.4 Hz, 1H), 7.23 (d, J=8.4 Hz, 1H), 7.11 (s, 1H), 6.85 (s, 1H), 6.77 (d, J=8.5 Hz, 1H), 6.52 (s, 1H), 5.72 (d, J=7.3 Hz, 2H), 5.34 (d, J=7.7 Hz, 1H), 5.29 (s, 1H), 5.12 (s, 1H), 5.10 (s, 1H), 4.80 (s, 1H), 4.66 (d, J=6.8 Hz, 1H), 4.45 (s, 1H), 4.41 (s, 1H), 4.11 (s, 2H), 4.07-4.03 (m, 3H), 4.00 (d, J=3.6 Hz, 1H), 3.89 (dd, J=3.7, 2.2 Hz, 1H), 3.67 (d, J=10.6 Hz, 1H), 3.57-3.55 (m, 1H), 3.54-3.53 (m, 1H), 3.51 (d, J=7.1 Hz, 2H), 3.47-3.45 (m, 3H), 3.37 (d, J=5.2 Hz, 1H), 3.35 (d, J=5.0 Hz, 1H), 3.26 (s, 2H), 3.25 (s, 1H), 3.13 (d, J=6.8 Hz, 2H), 2.94-2.89 (m, 3H), 2.60 (d, J=1.8 Hz, 1H), 2.57-2.54 (m, 211), 2.38-2.36 (m, 1H), 2.12-2.09 (m, 2H), 1.84-1.80 (m, 3H), 1.66-1.63 (m, 2H), 1.50 (s, 2H), 1.15 (t, J=7.3 Hz, 1H), 1.13 (s, 1H), 1.11 (d, J=6.2 Hz, 3H), 0.91 (d, J=6.2 Hz, 3H), 0.86 (d, J=6.1 Hz, 3H).

Example 17

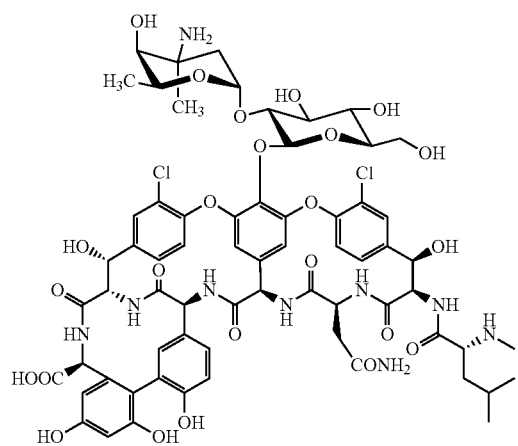

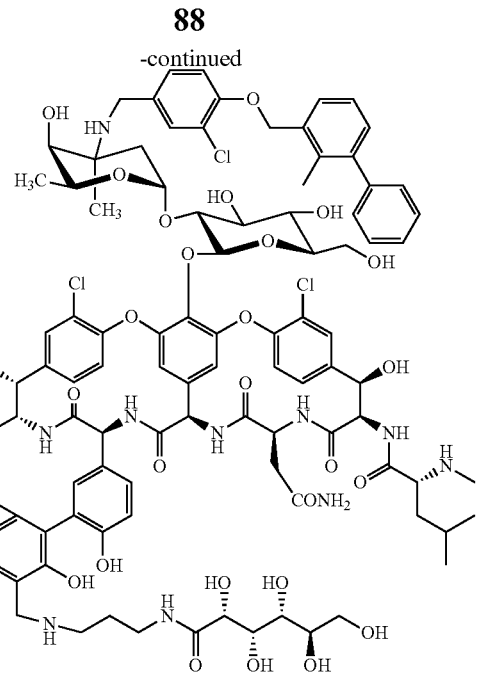

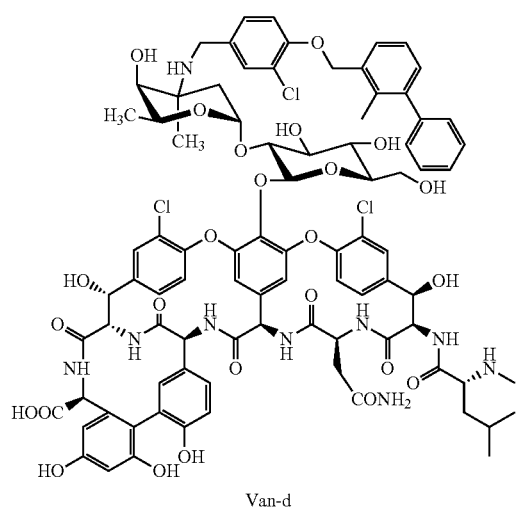

Van-d

Step 1: commercially available vancomycin (100 mg), DIPEA (30 μL) were dissolved in 3 mL of DMF to give a turbid solution, which was heated to 50° C. to become clear. 3-chloro-4-((2-methyl-[1,1'-biphenyl]-3-yl)methoxyl)benzaldehyde (30 mg) was added, and the mixture was heated under stirring for 4 h. Then, NaCNBH$_3$ (8 mg), 1 mL of methanol and 30 μL, of TFA were added, and the reaction was stirred overnight at room temperature, and monitored by HPLC. The reaction mixture was added with diethyl ether (50 mL) to generate precipitates, which was filtered to give a crude. The crude was purified by reverse-phase C18 HPLC and lyophilized to give Van-d (40 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for $C_{87}H_{92}C_{13}N_9O_{25}$ 1767.5270, found 884.7633 $[M+2H]^{2+}$.

Step 2: Van017 was prepared using the same needed materials, reagents and preparation method as those in example 16 except that Van-c in example 16 was replaced with Van-d. HRMS (ESI$^+$) calculated for $C_{97}H_{112}C_{13}N_{11}O_{31}$ $[M+2H]^{2+}$ 2031.6591, found 1016.8385.

$^1$H NMR (600 MHz, DMSO-d$_6$) δ 7.83-7.81 (m, 1H), 7.58 (d, J=2.0 Hz, 1H), 7.46 (dd, J=14.4, 6.8 Hz, 6H). 7.43 (d, J=1.7 Hz, 1H), 7.40-7.39 (m, 1H), 7.38-7.35 (m, 3H), 7.30 (d, J=8.4 Hz, 1H), 7.29-7.27 (m, 3H), 7.23-7.19 (m, 3H), 6.86-6.83 (m, 1H), 6.77 (d, J=8.5 Hz, 1H), 6.53 (s, 1H), 5.72 (d, J=10.0 Hz, 2H), 5.33 (d, J=7.6 Hz, 1H), 5.26 (s, 2H), 5.12 (s, 2H), 5.09 (d, J=2.0 Hz, 1H), 4.80 (s, 1H), 4.64 (d, J=6.4 Hz, 1H), 4.45 (d, J=5.6 Hz, 1H), 4.41 (d, J=5.7 Hz, 1H), 4.06 (s, 2H), 4.00 (d, J=3.6 Hz, 2H), 3.93 (s, 1H), 3.89-3.88 (m. 1H), 3.66 (d, J=10.6 Hz, 1H), 3.56-3.53 (m, 2H), 3.47-3.46 (m, 2H), 3.36 (dd, J=10.7, 5.0 Hz, 2H), 3.28-3.24 (m, 2H), 3.21-3.17 (m, 2H), 3.16-3.12 (m, 2H), 2.92 (t, J=7.4 Hz, 3H), 2.57 (s, 3H), 2.19 (s, 3H), 2.12-2.07 (m, 2H), 2.06 (d, J=7.9 Hz, 3H), 1.84-1.77 (m, 4H), 1.67-1.62 (m, 3H), 1.45 (s, 3H), 1.10 (d, J=6.3 Hz, 3H), 0.91 (d, J=6.1 Hz, 3H), 0.86 (d, J=6.2 Hz, 3H).

Example 18

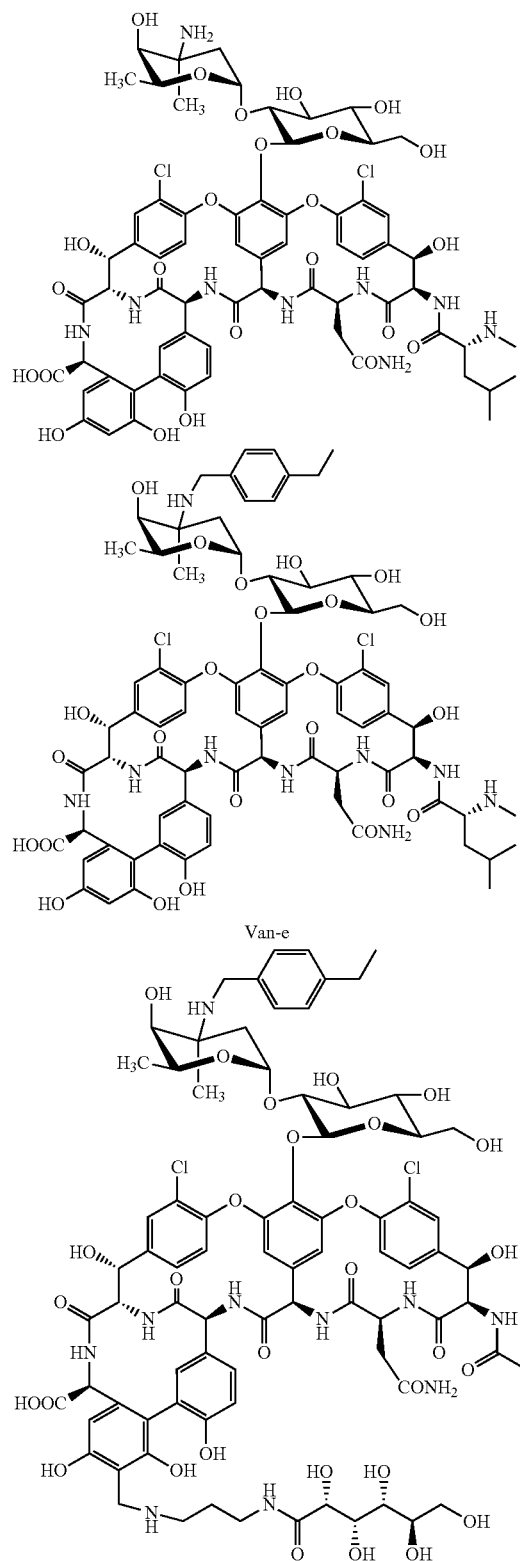

Step 1: commercially available vancomycin (100 mg) and DIPEA (30 μL) were dissolved in 3 mL of DMF to give an opaque solution, which was heated to 50° C. to become clear. p-ethylbenzaldehyde (30 mg) was added, and the reaction was heated under stirring for 4 h. (Aromatic aldehyde has a low reactivity, and therefore, it is necessary to prolong the reaction time and heat up to accelerate the reaction rate. Vancomycin does not have a good solubility in DMF, and the added DIPEA may enhance the dissolution. If there are insolubles, the reaction rate would be affected.) Then, NaCNBH$_3$ (8 mg), 1 mL of methanol and 30 μL of TFA were added at room temperature, and the reaction was stirred overnight and monitored by HPLC. The reaction mixture was added with diethyl ether (50 mL) to generate precipitates, which was filtered to give a crude. The crude was purified by reverse-phase C18 HPLC and lyophilized to give Van-e (40 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for C$_{75}$H$_{85}$Cl$_2$N$_9$O$_{24}$ [M+2H]$^{2+}$ 1565.5085, found 783.7540.

Step 2: Van018 was prepared using the same needed materials, reagents and preparation method as those in example 16 except that 4'-trifluoromethyl-biphenyl-4-carbaldehyde in example 16 was replaced with p-ethylbenzaldehyde. HRMS (ESI$^+$) calculated for C$_{85}$H$_{105}$Cl$_2$N$_{11}$O$_{30}$ 1829.6406, found 915.8275 [M+2H]$^{2+}$.

$^1$H NMR (600 MHz, DMSO-d$_6$) δ 7.82 (s, 1H), 7.48 (d, J=8.5 Hz, 2H), 7.47-7.45 (m, 2H), 7.36 (s, 1H), 7.35 (s, 1H), 7.30 (d, J=8.4 Hz, 1H), 7.25 (s, 1H), 7.24 (s, 1H), 7.22 (d, J=8.4 Hz, 1H), 7.10 (s, 1H), 6.84 (d, J=8.6 Hz, 1H), 6.77 (d, J=8.6 Hz, 1H), 6.52 (s, 1H), 5.72 (s, 214), 5.33 (d, J=7.6 Hz, 1H), 5.12 (s, 1H), 5.09 (s, 1H), 4.80 (s, 1H), 4.63 (d, J=6.5 Hz, 1H), 4.45-4.43 (m, 1H), 4.41-4.39 (m, 1H), 4.10 (s, 1H), 4.05 (s, 2H), 4.00 (d, J=3.6 Hz, 2H), 3.97-3.92 (m, 4H), 3.90-3.88 (m, 1H), 3.66 (d, J=10.7 Hz, 2H), 3.57-3.55 (m, 2H), 3.54 (s, 1H), 3.47-3.46 (m, 2H), 3.45 (d, J=2.1 Hz, 1H), 3.36 (dd, J=10.6, 4.9 Hz, 3H), 3.25 (d, J=8.7 Hz, 2H), 3.07 (q, J=7.3 Hz, 3H), 2.58 (s, 1H), 2.37 (d, J=3.6 Hz, 1H), 2.11-2.06 (m, 3H), 1.81-1.76 (m, 3H), 1.67-1.62 (m, 3H), 1.46 (s, 2H), 1.17-1.15 (m, 2H), 1.14 (d, J=1.7 Hz, 2H), 1.13 (d, J=1.9 Hz, 1H), 1.09 (d, J=6.3 Hz, 3H), 0.91 (d, J=6.2 Hz, 3H), 0.86 (d, J=6.2 Hz, 3H).

Example 19

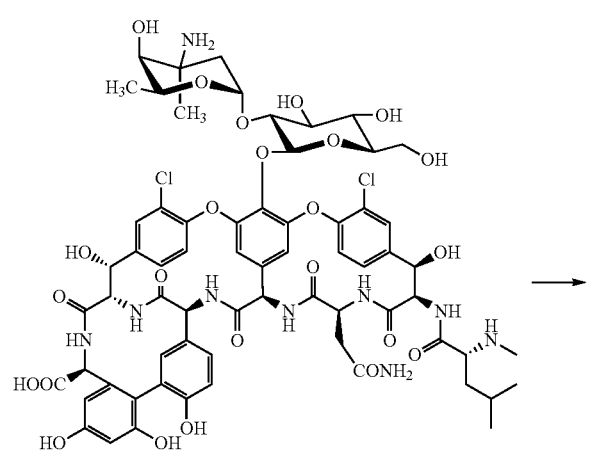

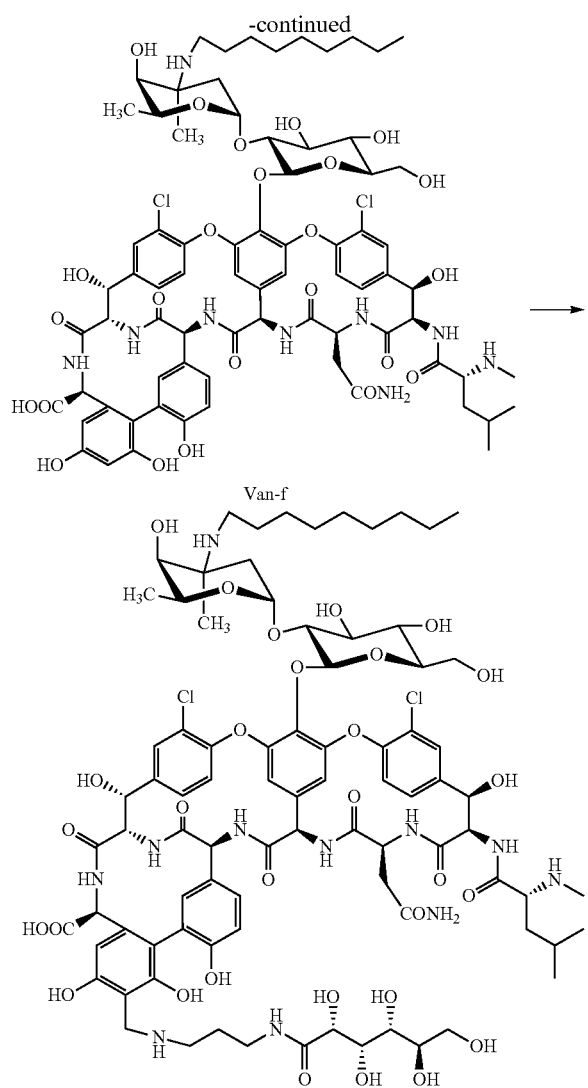

Van-f

Step 1: commercially available vancomycin (100 mg) and DIPEA (30 μL) were dissolved in 3 mL of DMF to give an opaque solution, which was heated to 50° C. to become clear. 1-nonanal (30 μL) was added, and the reaction was heated and stirred for 4 h. Then, NaCNBH$_3$ (8 mg), 1 mL of methanol and 30 μL of TFA were added at room temperature, and the reaction was stirred overnight and monitored by HPLC. The reaction mixture was added with diethyl ether (50 mL) to generate precipitates, which was filtered to give a crude. The crude was purified by reverse-phase C18 HPLC and lyophilized to give Van-f (40 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for $C_{75}H_{93}Cl_2N_9O_{24}$ 1573.5711, found 787.7856 $[M+2H]^{2+}$.

Step 2: Van019 was prepared using the same needed materials, reagents and preparation method as those in example 16 except that Van-c in example 16 was replaced with Van-f. HRMS (ESI$^+$) calculated for $C_{78}H_{100}Cl_2N_{10}O_{25}$ $[M+2H]^{2+}$ 1646.6238, found 824.3191.

$^1$H NMR (600 MHz, DMSO-d$_6$) δ 7.81 (s, 1H), 7.48 (d, J=8.7 Hz, 1H), 7.46-7.44 (m, 1H), 7.41 (d, J=7.5 Hz, 1H), 7.29 (s, 1H), 7.28 (s, 1H), 7.20 (d, J=8.4 Hz, 1H). 7.10-7.09 (m, 1H), 6.85-6.83 (m, 1H), 6.78 (s, 1H), 6.76 (s, 1H), 6.53 (s, 1H), 5.72 (s, 1H), 5.70 (s, 1H), 5.30 (d, J=7.7 Hz, 1H), 5.27 (s, 1H), 5.12 (s, 2H), 5.08-5.06 (m, 1H), 4.79 (s, 1H), 4.59 (d, J=6.3 Hz, 1H), 4.43 (s, 1H), 4.40 (s, 1H), 4.10-4.08 (m, 1H), 4.06-4.04 (m, 2H), 4.00 (d, J=3.6 Hz, 1H), 3.89 (dd, J=3.7, 2.2 Hz, 1H), 3.66 (d, J=10.9 Hz, 2H), 3.56 (t, J=2.8 Hz, 1H), 3.54 (d, J=2.4 Hz, 1H), 3.53-3.48 (m, 3H), 3.47-3.46 (m, 2H), 3.37 (d, J=5.2 Hz, 1H), 3.35 (d, J=4.8 Hz, 1H), 3.25 (s, 3H), 3.20-3.18 (m, 1H), 3.16-3.12 (m, 2H), 2.94-2.91 (m, 2H), 2.76-2.72 (m, 2H), 2.69-2.65 (m, 2H), 2.59 (s, 1H), 2.57-2.53 (m, 3H), 2.37 (d, J=3.6 Hz, 1H), 2.13-2.08 (m, 2H), 1.97 (d, J=14.5 Hz, 2H), 1.84-1.80 (m, 2H), 1.77 (d, J=13.2 Hz, 2H), 1.66-1.62 (m, 2H), 1.53-1.48 (m, 3H), 1.33 (s, 2H), 1.23 (d, J=11.9 Hz, 14H), 1.06 (d, J=6.3 Hz, 3H), 0.91 (d, J=6.1 Hz, 3H), 0.87-0.84 (m, 3H), 0.83 (d, J=7.1 Hz, 2H).

Example 20

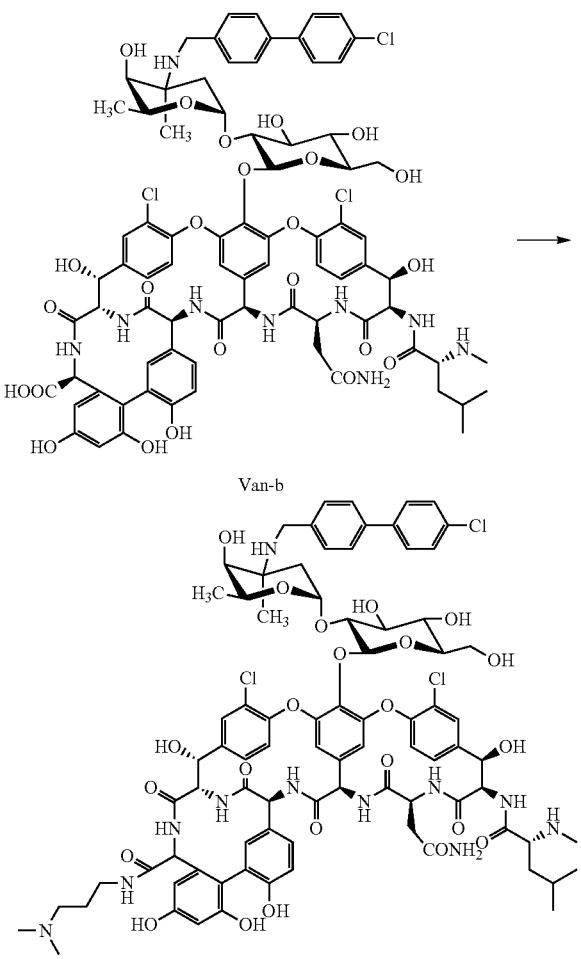

Van-b

Van-b (50 mg, 30 μmol) was dissolved in 1 mL of DMF, added with HBTU (O-(benzotriazol-1-yl)-N,N,N',N'-tetramethyluronium hexafluorophosphate) (21 mg, 45 μmol) and DIPEA (25 μL, 150 μmol), and stirred at room temperature for 15 min. 3-Dimethylaminopropylamine (18 μL, 120 μmol) was added, and the reaction was stirred at room temperature for 24 h and monitored by HPLC. The reaction mixture was diluted with water, and the crude was purified by reverse-phase C18 HPLC and lyophilized to give Van020 as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI+) calculated for $C_{84}H_{96}C_{13}N_{11}O_{23}$ [M+2H]$^{2+}$ 1731.5746, found 866.7873.

$^1$H NMR (600 MHz, DMSO-d$_6$) δ 7.84 (d, J=1.9 Hz, 1H), 7.74 (s, 1H), 7.73-7.69 (m, 4H), 7.56 (d, J=8.1 Hz, 4H), 7.53 (d, J=8.3 Hz, 2H), 7.49-7.46 (m, 1H), 7.33 (d, J=8.4 Hz, 1H), 7.26 (s, 1H), 7.22 (d, J=8.3 Hz, 1H), 6.78 (dd, J=8.4, 1.9 Hz, 1H), 6.71 (d, J=8.4 Hz, 1H), 6.39 (d, J=2.3 Hz, 1H), 6.22 (d, J=2.3 Hz, 1H), 5.77-5.74 (m, 1H), 5.36 (d, J=7.7 Hz, 1H), 5.30-5.27 (m, 2H), 4.93 (s, 1H), 4.68 (q, J=6.7 Hz, 1H), 4.48 (d, J=5.1 Hz, 1H), 4.32 (d, J=5.2 Hz, 1H), 4.26 (s, 1H), 4.04 (q, J=12.7 Hz, 3H), 3.96 (d, J=7.3 Hz, 1H), 3.68 (d, 1=10.7 Hz, 1H), 3.58 (t, 1=8.5 Hz, 2H), 3.35 (dt, J=12.9, 6.0 Hz, 2H), 3.31-3.24 (m, 3H), 3.11 (dt, J=20.1, 6.9 Hz, 2H), 3.00-2.96 (m, 2H), 2.75 (d, J=4.0 Hz, 6H), 2.63 (s, 2H), 2.14 (td, J=15.4, 14.1, 6.4 Hz, 3H), 1.87-1.77 (m, 4H), 1.71-1.53 (m, 5H), 1.51 (s, 3H), 1.13 (d, J=6.3 Hz, 3H), 0.90 (d, J=6.2 Hz, 3H), 0.85 (d, J=6.3 Hz, 3H).

Example 21

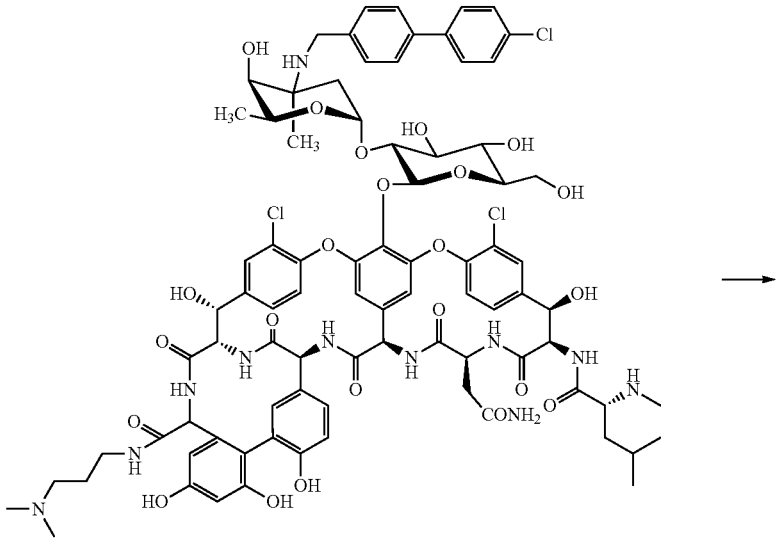

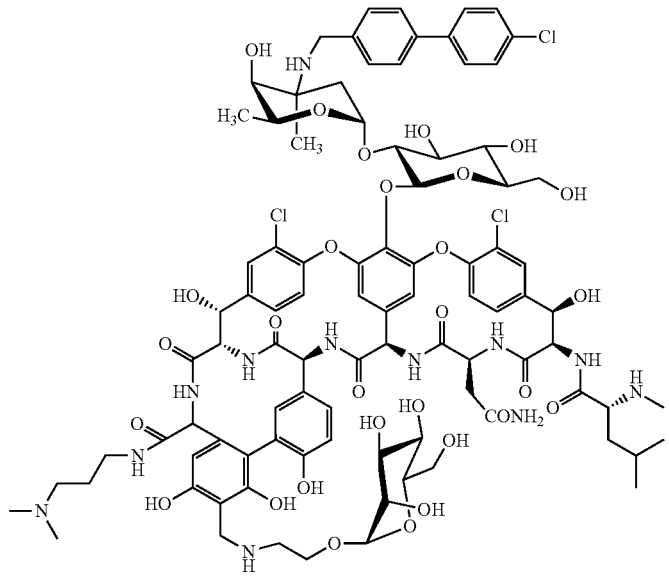

2-Aminoethyl-α-D-mannopyranoside 2 (30 mg) was dissolved in a mixture of 100 μL of water and 500 μL of acetonitrile, added with 30 μL of DIPEA, and stirred at room temperature until the solid was completely dissolved (10 min). Then, the mixture was added with 2 μL of a 37 wt % formaldehyde solution, stirred at room temperature for 15 min, cooled to −10° C. and stirred for 5 min. The mixture was quickly mixed with 1.5 mL of a 80% solution of Van020 (25 mg) in acetonitrile, added with 30μ, of DIPEA, and stirred at −10° C. for 8 h. The reaction was monitored by HPLC. HPLC: C18 column (5 μm, 4.6×250 mm), UV detection at 214 nm, elution conditions: a gradient of 2-90% acetonitrile containing 0.1% v/v TFA over 30 min. The crude was purified by reverse-phase C18 HPLC and lyophilized to give Van021 as a white solid. HRMS (ESI$^+$) calculated for $C_{93}H_{13}C_{13}N_{12}O_{29}$ [M+2H]$^{2+}$ 1966.6802, found 984.3486.

$^1$H NMR (600 MHz, DMSO-d$_6$) δ 7.83 (s, 1H), 7.74-7.70 (m, 4H), 7.69 (d, J=2.1 Hz, 1H), 7.57 (d, J=8.0 Hz, 2H), 7.52 (dd, J=6.9, 4.9 Hz, 4H), 7.47-7.45 (m, 1H), 7.31 (d, J=8.4 Hz, 1H), 7.23 (d, J=8.4 Hz, 1H), 7.19 (s, 1H), 6.84 (dd, J=8.7, 1.9 Hz, 1H), 6.77 (d, J=8.5 Hz, 1H), 6.49 (s, 1H), 5.73 (d, J=7.3 Hz, 1H), 5.70 (s, 1H), 5.39 (s, 1H), 5.35 (d, J=7.6 Hz, 1H), 5.14 (s, 1H), 5.11 (s, 1H), 4.80 (s, 1H), 4.65 (d, J=6.9 Hz, 1H), 4.64 (d, J=1.7 Hz, 1H), 4.47 (s, 1H), 4.27 (d, J=5.1 Hz, 1H), 4.17 (d, J=7.0 Hz, 1H), 4.11 (d, J=13.2 Hz, 2H), 4.02 (s, 3H), 3.86-3.82 (m, 21H), 3.67 (dd, J=3.5, 1.7 Hz, 1H), 3.66-3.64 (m, 1H), 3.63 (d, J=2.3 Hz, 1H), 3.56 (t, J=8.5 Hz, 2H), 3.50 (dd, J=9.0, 3.4 Hz, 2H), 3.38 (dd, J=11.9, 6.8 Hz, 3H), 3.33 (ddd, J=9.2, 6.3, 2.2 Hz, 2H), 3.28-3.24 (m, 2H), 3.11 (s, 3H), 3.01-2.95 (m, 3H), 2.72 (d, J=1.8 Hz, 6H), 2.57 (s, 2H), 2.10 (d, J=10.0 Hz, 3H), 1.83 (d, J=13.6 Hz, 4H), 1.66 (s, 3H), 1.50 (s, 3H), 1.11 (d, J=6.2 Hz, 3H), 0.91 (d, J=6.1 Hz, 3H), 0.86 (d, J=6.2 Hz, 3H).

Example 22

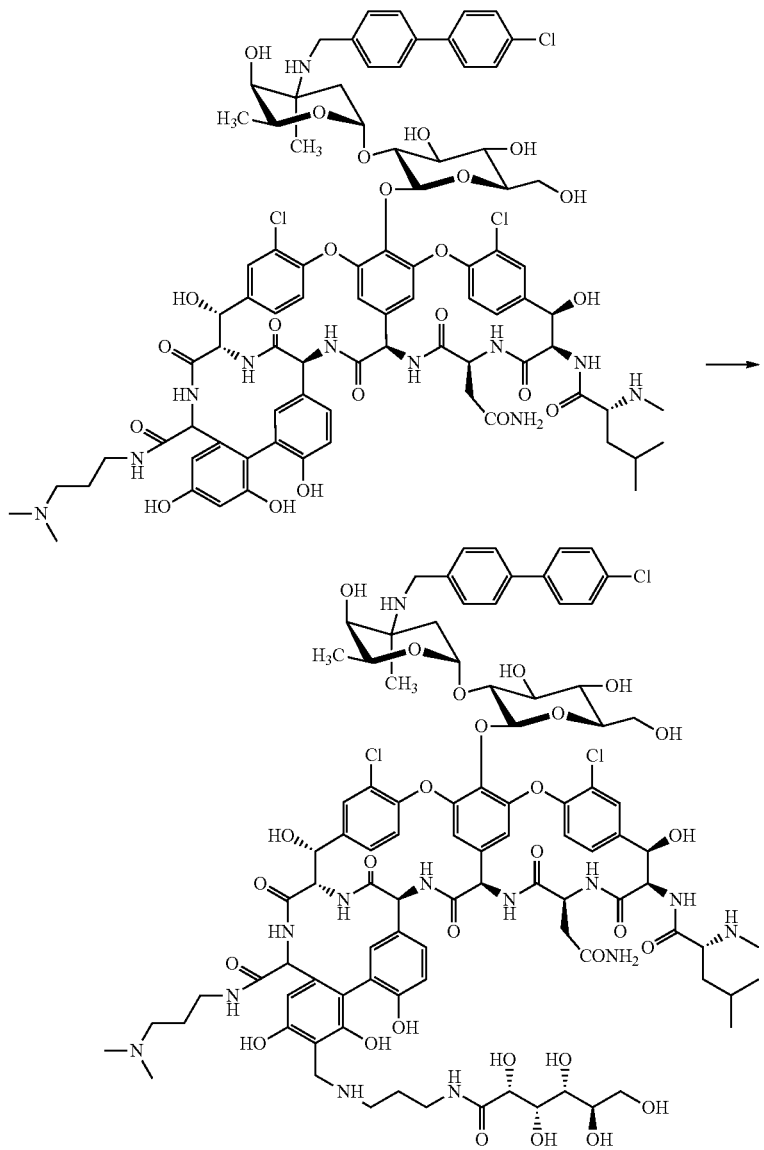

Van022 was prepared using the same needed materials, reagents and preparation method as those in example 21 except that 2-aminoethyl-α-D-mannopyranoside 2 in example 21 was replaced with the gluconolactone derivative 6. HRMS (ESI) calculated for $C_{94}H_{116}C_{13}N_{13}O_{29}$ [M+2H]$^{2+}$ 1995.7067, found 998.8520.
$^1$H NMR (600 MHz, DMSO-d$_6$) δ 7.82-7.81 (m, 1H), 7.75-7.70 (m, 4H), 7.69 (d, J=2.1 Hz, 1H), 7.56-7.52 (m, 4H), 7.52 (d, J=2.0 Hz, 1H), 7.50 (d, J=8.6 Hz, 1H), 7.47-7.45 (m, 1H), 7.30 (d, J=8.4 Hz, 1H), 7.24 (d, J=8.3 Hz, 1H), 7.20 (s, 1H), 6.85 (d, J=9.1 Hz, 1H), 6.77 (d, J=8.5 Hz, 1H), 6.48 (s, 1H), 5.72 (d, J=12.3 Hz, 2H), 5.35 (d, J=7.7 Hz, 1H), 5.30 (s, 1H), 5.13 (s, 1H), 5.11-5.10 (m, 1H), 4.81 (s, 1H), 4.65 (d, J=6.5 Hz, 1H), 4.48-4.46 (m, 1H), 4.29 (d, J=5.4 Hz, 1H), 4.17 (s, 1H), 4.06-4.04 (m, 2H), 4.02 (d, J=11.9 Hz, 2H), 4.00 (d, J=3.6 Hz, 1H), 3.88 (dd, J=3.7, 2.3 Hz, 1H), 3.67 (d, J=10.5 Hz, 1H), 3.56 (d, J=3.3 Hz, 1H), 3.54 (d, J=2.2 Hz, 1H), 3.52-3.49 (m, 2H), 3.36 (dd, J=10.5, 4.9 Hz, 2H), 3.26 (d, J=8.7 Hz, 2H). 3.11 (ddd, J=20.1, 13.4, 6.5 Hz, 4H), 2.99-2.94 (m, 3H), 2.93-2.89 (m, 2H), 2.73 (d, J=4.5 Hz, 6H), 2.61-2.59 (m, 1H), 2.57 (s, 3H), 2.38-2.36 (m, 1H), 2.10 (d, J=11.1 Hz, 3H). 1.84-1.76 (m, 6H), 1.66-1.62 (m, 2H), 1.50 (s, 3H), 1.11 (d, J=6.3 Hz, 3H), 0.91 (d, J=6.1 Hz, 3H), 0.86 (d, J=6.1 Hz, 3H).
Example 23
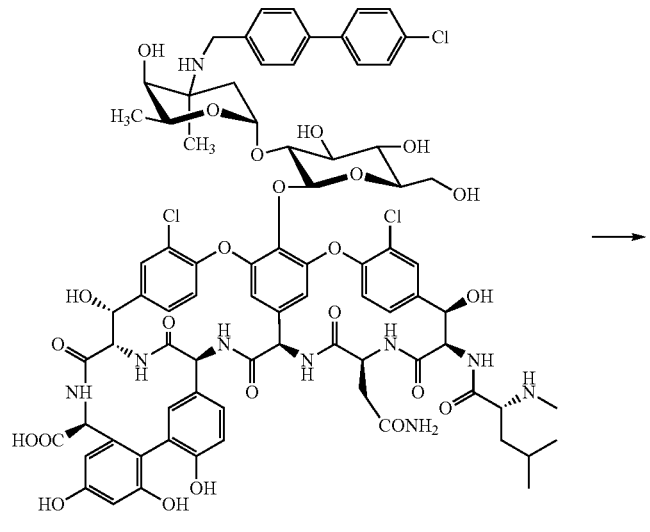
Van-b
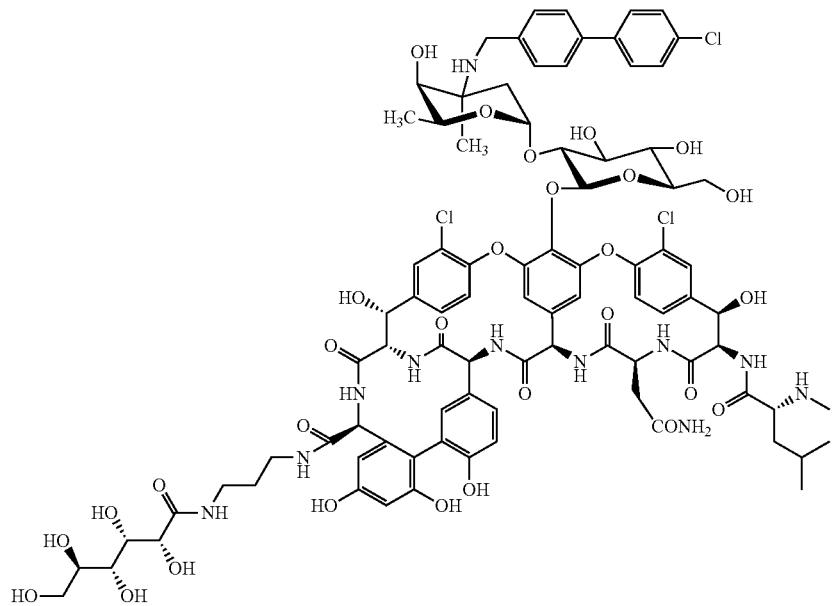

Van-b (50 mg, 30 μmol) was dissolved in 1 mL of DMF, added with HBTU (O-(benzotriazol-1-yl)-N,N,N',N'-tetramethyluronium hexafluorophosphate) (21 mg, 45 μmol) and DIPEA (25 μL, 150 μmol), and stirred at room temperature for 15 min. The gluconolactone derivative 6 (30 mg, 80 μmol) was added, and the reaction was stirred at room temperature for 24 h and monitored by HPLC. The reaction mixture was diluted with water, and the crude was purified by reverse-phase C18 HPLC and lyophilized to give Van023 as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for $C_{88}H_{102}C_{13}N_{11}O_{29}$ [M+2H]$^{2+}$ 1881.5910, found 941.7995.

$^1$H NMR (600 MHz, DMSO-d$_6$) δ 7.84 (s, 1H), 7.75-7.70 (m, 4H), 7.69 (d, J=2.1 Hz, 1H), 7.56-7.52 (m, 4H), 7.52-7.51 (m, 1H), 7.45 (d, J=8.5 Hz, 2H), 7.30 (d, J=8.4 Hz, 2H), 7.20 (q, J=8.4 Hz, 3H), 7.04 (d, J=10.4 Hz, 2H), 6.75 (d, J=9.0 Hz, 1H), 6.69 (d, J=8.5 Hz, 1H), 6.44-6.42 (m, 1H), 6.34 (d, J=2.3 Hz, 1H), 6.29-6.28 (m, 1H), 6.24 (d, J=2.4 Hz, 1H). 5.79 (d, J=6.6 Hz, 1H), 5.74 (d, J=7.2 Hz, 1H), 5.69 (s, 1H), 5.62 (s, 1H), 5.28 (s, 3H), 4.65 (d, J=6.6 Hz, 2H), 4.44 (s, 2H), 4.36 (d, J=5.4 Hz, 1H), 4.33 (d, J=5.7 Hz, 1H), 3.87 (t, J=2.8 Hz, 1H), 3.67 (d, J=10.9 Hz, 1H), 3.56 (d, J=8.4 Hz, 2H), 3.54-3.51 (m, 2H), 3.35-3.32 (m, 2H), 3.27-3.24 (m, 2H), 3.02 (s, 2H), 2.91 (s, 2H), 2.60 (d, J=3.4 Hz, 2H), 2.58 (s, 1H), 2.37 (d, J=3.6 Hz, 1H). 2.12-2.09 (m. 2H), 1.82 (d, J=13.3 Hz, 2H), 1.67-1.63 (m, 2H), 1.55 (d, J=8.8 Hz, 2H), 1.49 (s. 2H), 1.13-1.09 (m, 3H), 0.90 (d, J=6.3 Hz, 3H), 0.85 (t, =5.8 Hz, 3H).

Example 24

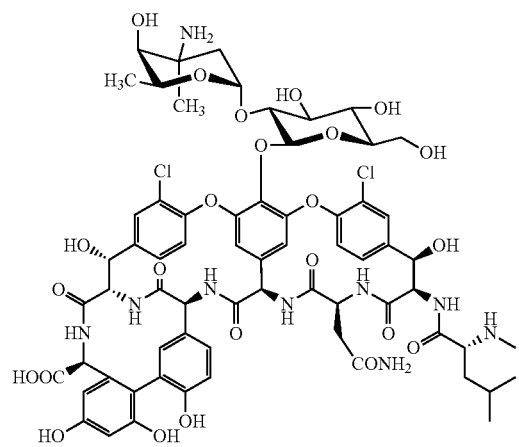

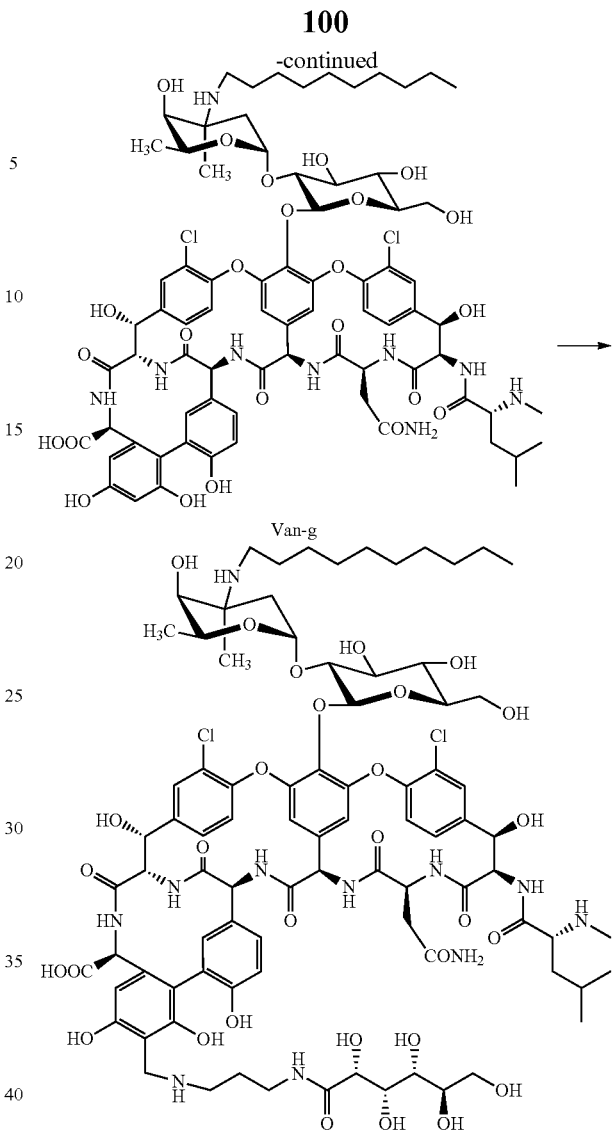

Step 1: Commercially available vancomycin (100 mg) and DIPEA (30 μL) were dissolved in 3 mL of DMF to give an opaque solution, which was heated to 50° C. to become clear. Decanal (30 μL) was added, and the mixture was heated under stirring for 4 h. Then, NaCNBH$_3$ (8 mg), 1 mL of methanol and 30 μL of TFA were added at room temperature, and the reaction was stirred overnight and monitored by HPLC. The reaction mixture was added with diethyl ether (50 mL) to generate precipitates, which was filtered to give a crude. The crude was purified by reverse-phase C18 HPLC and lyophilized to give Van-g (40 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for $C_{76}H_{95}Cl_2N_9O_{24}$ [M+2H]$^{2+}$ 1587.5867, found 794.8006.

$^1$H NMR (600 MHz, DMSO-d$_6$) δ 8.70 (s, 1H), 7.81 (d, J=1.9 Hz. 1H), 7.52 (d, J=8.6 Hz, 1H), 7.44 (dd, J=8.3, 1.8 Hz, 1H), 7.29 (d, J=8.4 Hz, 1H), 7.17 (d, J=8.4 Hz, 1H), 7.15-7.11 (m, 1H), 6.76 (dd, J=8.4, 2.0 Hz, 1H), 6.70 (d, J=8.4 Hz, 2H), 6.38 (d, J=2.3 Hz, 1H), 6.23 (d, J=2.3 Hz, 1H), 5.73 (d, J=7.8 Hz, 1H), 5.59 (s, 1H), 5.27 (dd, J=22.9, 6.0 Hz, 2H), 5.14 (dd, J=14.8, 2.8 Hz, 2H), 5.09 (s, 1H), 4.89 (s, 1H), 4.60 (d, J=6.7 Hz, 1H), 4.42 (dd, J=11.8, 5.6 Hz,

2H), 4.17 (s, 2H), 3.94 (s, 1H), 3.65 (d, J=10.8 Hz, 1H), 3.54 (t, J=8.5 Hz, 1H), 3.31-3.22 (m, 3H), 2.74 (s, 1H), 2.67 (d, J=7.2 Hz, 1H), 2.60 (s, 4H), 2.12 (d, J=12.6 Hz, 1H), 1.96 (d, J=11.6 Hz, 1H), 1.77 (d, J=13.1 Hz, 1H), 1.63 (ddd, J=26.5, 12.5, 6.7 Hz, 2H), 1.51 (s, 3H), 1.32 (s, 3H), 1.23 (d, J=18.1 Hz, 16H), 1.06 (d, J=6.3 Hz, 3H), 0.89 (d, J=6.2 Hz, 3H), 0.83 (td, J=7.1, 6.7, 3.6 Hz, 6H).

Step 2: Van024 was prepared using the same needed materials, reagents and preparation method as those in example 16 except that Van-c in example 16 was replaced with Van-g. HRMS (ESI$^+$) calculated for $C_{86}H_{115}Cl_2N_{11}O_{30}$ [M+2H]$^{2+}$ 1851.7188, found 926.8674.

$^1$H NMR (600 MHz, DMSO-d$_6$) δ 8.77 (s, 1H), 8.64 (s, 1H), 7.80 (d, J=1.9 Hz, 1H), 7.60 (s, 1H), 7.48 (d, J=8.5 Hz, 1H), 7.46-7.41 (m, 1H), 7.28 (d, J=8.3 Hz, 1H), 7.20 (d, J=8.3 Hz, 1H), 6.84 (dd, J=8.5, 1.9 Hz, 1H), 6.77 (d, J=8.4 Hz, 1H), 6.53 (s, 1H), 5.73-5.68 (m, 2H), 5.30 (d, J=7.7 Hz, 1H), 5.27 (d, J=4.1 Hz, 1H), 5.12 (s, 2H), 5.07 (d, J=2.0 Hz, 1H), 4.80 (s, 1H), 4.43 (s. 1H), 4.41 (d, J=5.8 Hz, 1H), 4.10-4.04 (m, 3H), 4.00 (d, J=3.6 Hz, 2H), 3.89 (dd, J=3.6, 2.2 Hz, 1H), 3.65 (d, J=10.6 Hz, 1H), 3.57-3.46 (m, 6H), 3.36 (dd, J=10.7, 5.0 Hz, 1H), 3.28-3.22 (m, 3H), 3.21-3.16 (m, 1H), 3.14 (dt, J=13.0, 6.2 Hz, 1H), 2.92 (s, 2H), 2.71 (d, J=39.8 Hz, 3H), 2.56 (s, 3H), 2.11 (s, 1H), 1.96 (d, J=10.7 Hz, 1H), 1.86-1.73 (m, 3H), 1.64 (d, J=9.9 Hz, 2H), 1.50 (s, 3H), 1.33 (s, 3H), 1.22 (s, 16H), 1.06 (d, J=6.3 Hz, 3H), 0.90 (d, J=6.1 Hz, 3H), 0.87-0.81 (m, 6H).

Example 25

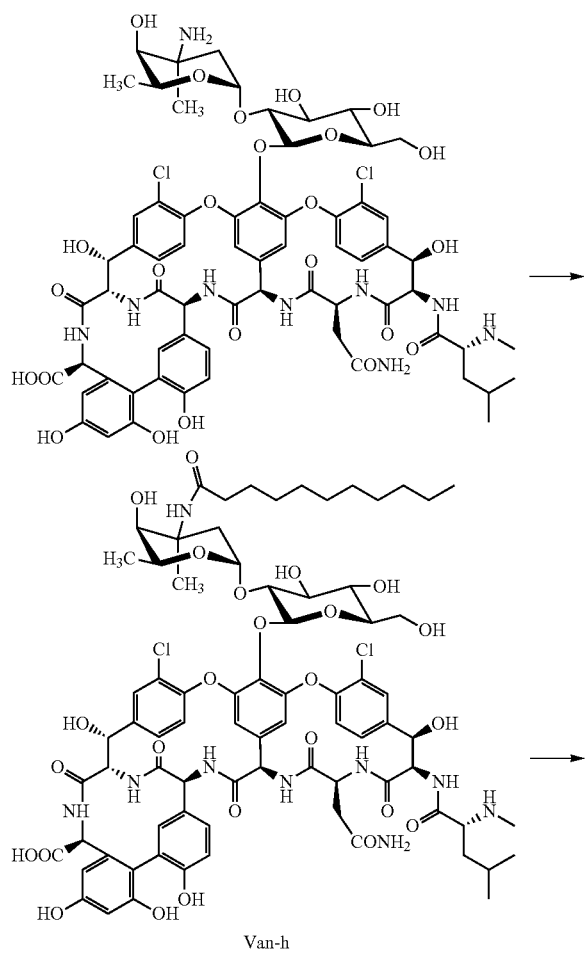

Van-h

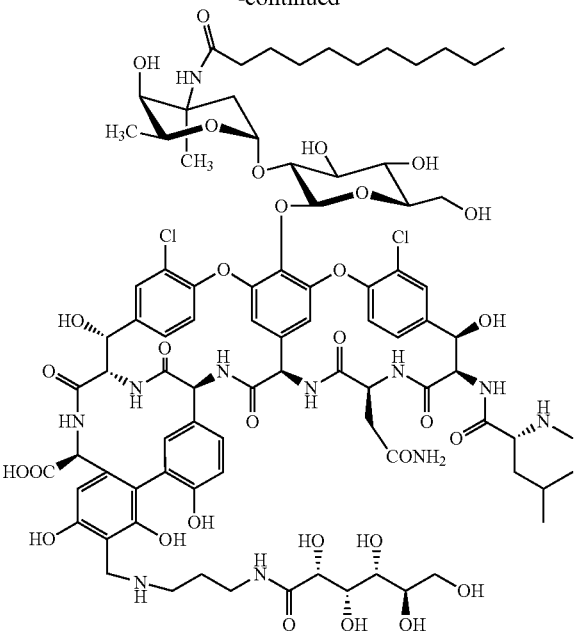

Step 1: commercially available vancomycin (100 mg) and DIPEA (30 μL) were dissolved in 3 mL of DMF. After the solution became clear, 15 μL of undecanoyl chloride was added in three portions under ice-water bath, and the reaction was stirred for 2 h under argon. The reaction mixture was added with diethyl ether (50 mL) to generate precipitates, which was filtered to give a crude. The crude was purified by reverse-phase C18 HPLC and lyophilized to give Van-h (40 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for $C_{77}H_{95}Cl_2N_9O_{25}$ [M+2H]$^{2+}$ 1615.5816, found 808.7978.

$^1$H NMR (600 MHz, DMSO-d$_6$) δ 8.63 (s, 1H), 8.46 (d, J=5.7 Hz, 1H), 7.80 (d, J=2.0 Hz, 1H), 7.46 (dd, J=8.4, 1.8 Hz, 1H), 7.43 (dd, J=8.1, 1.9 Hz, 1H), 7.34 (d, J=8.3 Hz, 1H), 7.22 (s, 1H), 7.17-7.15 (m, 1H), 7.00 (d, J=8.3 Hz, 1H), 6.76 (dd, J=8.5, 2.1 Hz, 1H), 6.70 (dd, J=8.5, 3.2 Hz, 2H), 6.39 (d, J=2.3 Hz, 1H), 6.22 (d, J=2.3 Hz, 1H), 5.69 (d, J=8.3 Hz, 1H), 5.48 (d, J=2.1 Hz, 1H), 5.26-5.17 (m, 4H), 5.13 (d, J=4.7 Hz, 1H), 5.08 (s, 1H), 4.77 (dd, J=9.8, 4.5 Hz, 1H), 4.66 (d, J=6.7 Hz, 1H), 4.45 (d, J=5.7 Hz, 2H), 4.41 (d, J=5.7 Hz, 1H), 4.18 (s, 1H), 3.64 (d/=10.8 Hz, 1H). 3.56-3.48 (m, 3H), 3.25 (d, J=5.5 Hz, 2H), 3.13 (s, 1H), 2.82 (s, 3H), 2.41-2.30 (m, 3H), 2.10 (d, J=12.7 Hz, 2H), 1.88 (d, J=11.0 Hz, 1H), 1.71 (d, J=13.1 Hz, 1H), 1.57 (d, J=7.7 Hz, 3H), 1.50-1.42 (m, 2H), 1.36 (d, J=7.3 Hz, 2H), 1.34-1.13 (m, 17H), 1.05 (d, J=6.4 Hz, 3H), 0.85 (dd, J=6.7, 2.4 Hz, 3H), 0.81 (t, J=7.1 Hz, 3H), 0.77 (d, J=6.6 Hz, 3H).

Step 2: Van025 was prepared using the same needed materials, reagents and preparation method as those in example 16 except that N$^{van}$-2-(4'-trifluoromethyl-biphenyl-methyl)-vancomycin (Van-c) in example 16 was replaced with N$^{van}$-2-(undecanoyl)-vancomycin (Van-h). HRMS (ESI$^+$) calculated for $C_{87}H_{115}Cl_2N_{11}O_{31}$ [M+2H]$^{2+}$ 1879.7138, found 940.8659.

$^1$H NMR (600 MHz, DMSO-d$_6$) δ 8.67 (s, 1H), 7.76 (s, 1H), 7.49-7.45 (m, 1H), 7.43 (d, J=8.7 Hz, 1H), 7.31 (d, J=8.4 Hz, 2H), 7.11 (s, 1H), 7.06 (d, J=8.1 Hz, 1H), 6.84 (dd, J=8.7, 2.1 Hz, 1H), 6.82-6.72 (m, 2H), 6.52 (s, 1H), 5.64 (d,

J=7.9 Hz, 1H), 5.57 (s, 1H), 5.22 (dt, J=11.7, 3.6 Hz, 3H), 5.17-5.05 (m, 3H), 4.74 (s, 1H), 4.65 (d, J=6.8 Hz, 1H), 4.44 (dd, J=16.5, 5.8 Hz, 2H), 4.07 (d, J=27.1 Hz, 3H), 4.00 (d, J=3.5 Hz, 1H), 3.92-3.86 (m, 1H), 3.64 (d, J=10.5 Hz, 1H), 3.58-3.50 (m, 4H), 3.36 (dd, J=10.5, 4.5 Hz, 1H), 3.26 (d, J=5.5 Hz, 2H), 3.23-3.08 (m, 3H), 2.92 (s, 2H), 2.42-2.28 (m, 2H), 1.88 (d, J=10.0 Hz, 1H), 1.71 (d, J=13.1 Hz, 1H), 1.54 (q, J=8.0 Hz, 4H), 1.38 (hept, J=6.7 Hz, 1H), 1.28 (d, J=8.2 Hz, 5H), 1.21 (dd, J=14.0, 6.4 Hz, 14H), 1.05 (d, J=6.5 Hz, 3H), 0.87 (d, J=6.5 Hz, 3H). 0.82 (t, J=7.0 Hz, 3H), 0.79 (d, J=6.5 Hz, 3H).

Example 26

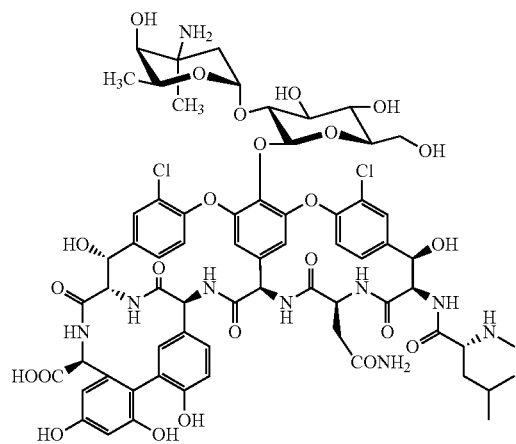

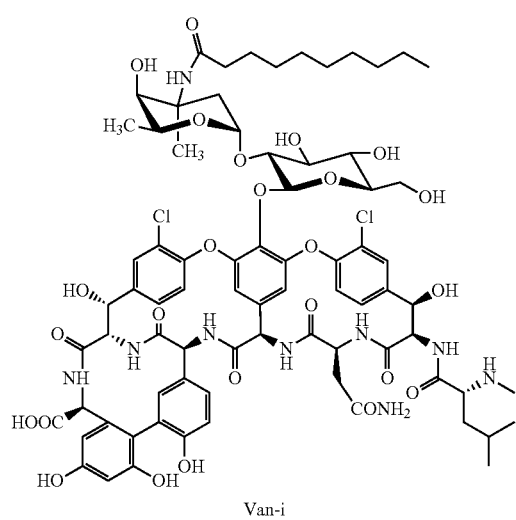

Van-i

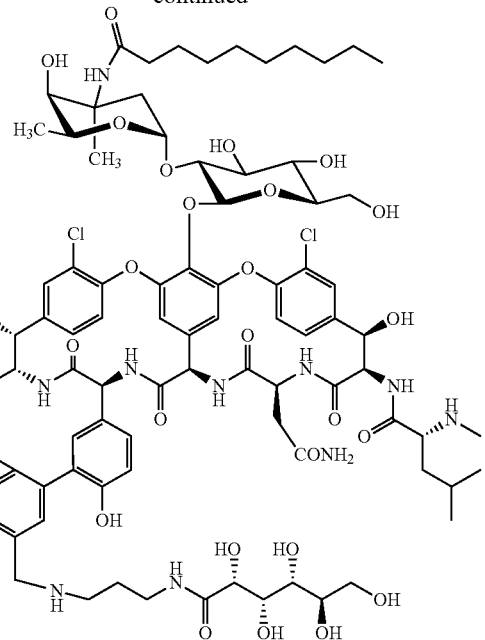

Step 1: commercially available vancomycin (100 mg) and DIPEA (30 μL) were dissolved in 3 mL of DMF. After the solution became clear, 15 μL of decanoyl chloride was added in three portions under ice-water bath and the reaction was stirred for 2 h under argon. The reaction mixture was added with diethyl ether (50 mL) to generate precipitates, which was filtered to give a crude. The crude was purified by reverse-phase C18 HPLC and lyophilized to give Van-i (40 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for $C_{76}H_{93}Cl_2N_9O_{25}$ [M+2H]$^{2+}$ 1601.5660, found 801.7908.

$^1$H NMR (600 MHz, DMSO-d$_6$) δ 8.63 (d, J=4.8 Hz, 1H), 7.80 (d, J=2.0 Hz, 1H), 7.49-7.38 (m, 2H), 7.34 (d, J=8.3 Hz, 1H), 7.22 (s, 1H), 7.16 (s, 2H), 7.00 (d, J=8.3 Hz, 1H), 6.76 (dd, J=8.4, 2.2 Hz, 1H), 6.70 (d, J=8.4 Hz, 2H), 6.39 (d, J=2.3 Hz, 1H), 6.22 (d, J=2.3 Hz, 1H), 5.69 (d, J=8.2 Hz, 1H), 5.48 (d, J=2.0 Hz, 1H), 5.29-5.16 (m, 4H), 5.13 (d, J=4.7 Hz, 1H), 5.08 (s, 1H), 4.77 (dd, J=9.5, 4.7 Hz, 1H), 4.66 (q, J=6.5 Hz, 1H), 4.45 (d, J=5.5 Hz, 1H), 4.41 (d, J=5.8 Hz, 1H), 4.18 (s, 1H), 3.64 (d, J=10.9 Hz, 1H), 3.59-3.47 (m, 3H), 3.25 (d, J=5.8 Hz, 2H), 3.13 (s, 1H), 2.82 (s, 3H), 2.42-2.29 (m, 2H), 2.18 (s, 1H), 2.14-2.07 (m, 1H), 1.88 (d, J=10.3 Hz, 1H), 1.70 (d, J=13.1 Hz, 1H), 1.57 (d, J=7.8 Hz, 3H), 1.46 (dt, J=13.7, 7.6 Hz, 1H), 1.42-1.34 (m, 1H), 1.30 (dd, J=9.8, 5.6 Hz, 2H), 1.26 (s, 3H), 1.21 (td, J=14.5, 11.7, 5.6 Hz, 10H), 1.05 (d, J=6.4 Hz, 3H), 0.85 (dd, J=6.7, 2.5 Hz, 3H), 0.84-0.79 (m, 3H), 0.77 (d, J=6.5 Hz, 3H).

Step 2: Van026 was prepared using the same needed materials, reagents and preparation method as those in example 25 except that Van-h in example 25 was replaced with Van-i. HRMS (ESI) calculated for $C_{86}H_{113}Cl_2N_{11}O_{31}$ [M+2H]$^{2+}$ 1865.6931. found 933.8577.

$^1$H NMR (600 MHz, DMSO-d$_6$) δ 8.66 (s, 1H), 7.46 (dd, J=8.3, 1.8 Hz, 1H), 7.45-7.39 (m, 1H), 7.31 (d, J=8.4 Hz, 2H), 7.13-6.98 (m, 2H), 6.84 (dd, J=8.6, 1.8 Hz, 2H), 6.77 (t, J=7.7 Hz, 2H), 6.52 (s, 1H), 5.64 (d, J=7.9 Hz, 1H), 5.57 (s, 1H), 5.22 (dt, J=11.7, 3.8 Hz, 3H), 5.17-5.06 (m, 3H), 4.65 (d, J=6.7 Hz, 1H), 4.44 (dd, J=16.4, 5.7 Hz, 2H), 4.13-4.01 (m, 3H), 4.00 (d, J=3.5 Hz, 1H), 3.89 (t, J=2.8 Hz, 1H), 3.64 (d, J=10.9 Hz, 1H), 3.61-3.48 (m, 4H), 3.36 (dd, J=9.1, 3.5 Hz, 1H), 3.26 (d, J=5.1 Hz, 2H), 3.19 (dt, J=13.4, 6.7 Hz, 1H), 3.14 (d, J=7.7 Hz, 2H), 2.92 (t, J=7.6 Hz, 2H), 2.83 (s, 3H), 2.43-2.27 (m, 2H), 1.88 (d, J=11.4 Hz, 1H), 1.81 (dq, J=14.2, 7.0 Hz, 2H), 1.71 (d, J=13.0 Hz, 1H), 1.54 (q, J=8.4, 7.5 Hz, 4H), 1.38 (dt, J=13.6, 6.6 Hz, 1H), 1.28 (d, J=8.8 Hz, 6H), 1.26-1.15 (m, 12H), 1.05 (d, J=6.3 Hz, 3H), 0.92-0.88 (m, 1H), 0.87 (d, J=6.6 Hz, 3H), 0.82 (t, J=6.8 Hz, 3H), 0.79 (d, J=6.5 Hz. 3H).

Example 27

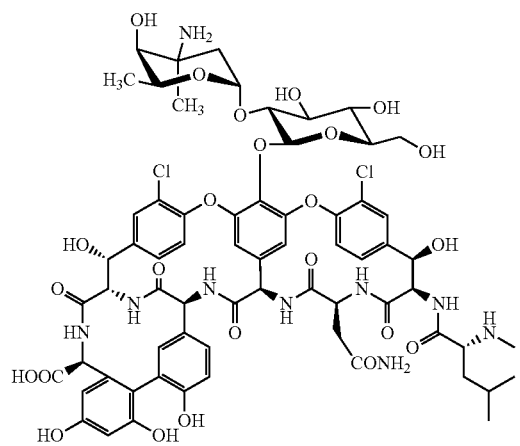

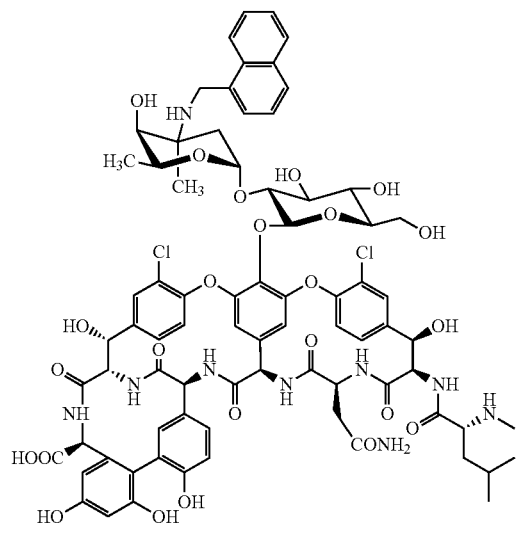

Van-j

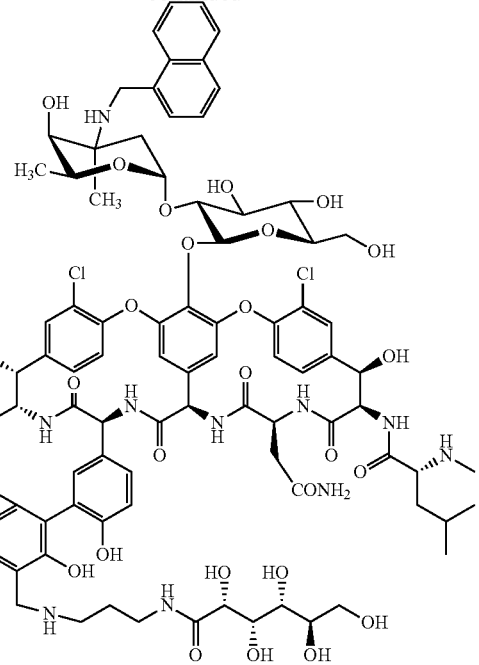

Step 1: Commercially available vancomycin (100 mg) and DIPEA (30 μL) were dissolved in 3 mL of DMF to give an opaque solution, which was heated to 50° C. to become clear. 2-naphthaldehyde (21 mg) was added, and the mixture was heated under stirring for 4 h. NaCNBH$_3$ (8 mg), 1 mL of methanol and 30 μL of TFA were added at room temperature, and the reaction was stirred overnight and monitored by HPLC. The reaction mixture was added with diethyl ether (50 mL) to generate precipitates, which was filtered to give a crude. The crude was purified by reverse-phase C18 HPLC and lyophilized to give Van-j (40 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for $C_{77}H_{83}Cl_2N_9O_{24}$ [M+2H]$^{2+}$ 1587.4928, found 794.7548.

$^1$H NMR (600 MHz, DMSO-d$_6$) δ 8.71 (s, 1H), 8.54 (d, J=5.5 Hz, 1H), 7.99 (s, 1H), 7.96 (d, J=8.5 Hz, 1H), 7.93 (dt, J=7.4, 3.1 Hz, 1H), 7.92-7.87 (m, 1H), 7.83 (d, J=1.8 Hz, 1H), 7.59-7.49 (m, 5H), 7.46 (dd, J=8.3, 1.8 Hz, 1H), 7.32 (d, J=8.4 Hz, 1H), 7.19 (d, J=8.4 Hz, 1H), 7.16-7.12 (m, 1H), 6.76 (dd, J=8.4, 2.0 Hz, 1H), 6.70 (d, J=8.5 Hz, 2H), 6.38 (d, J=2.3 Hz, 1H), 6.23 (d, J=2.3 Hz, 1H), 5.74 (d, J=7.8 Hz, 1H), 5.62 (s, 1H), 5.34 (d, J=7.7 Hz, 1H), 5.28 (d, J=4.3 Hz, 1H), 5.16 (dd, J=7.9, 2.8 Hz, 2H), 5.10 (s, 1H), 4.90 (s, 1H), 4.67 (d, J=6.6 Hz, 1H), 4.44 (d, J=5.6 Hz, 1H), 4.41 (d, J=5.7 Hz, 1H), 4.16 (t, J=10.4 Hz, 4H), 3.95 (s, 1H), 3.67 (d, J=10.6 Hz, 1H), 3.57 (t, J=8.5 Hz, 1H), 3.49 (s. 2H), 3.31-3.21 (m, 3H), 2.61 (s, 3H), 2.11 (d, J=11.5 Hz, 2H), 1.83 (d, J=13.2 Hz, 1H), 1.64 (ddd, J=28.9, 13.3, 6.2 Hz, 3H), 1.60-1.52 (m, 2H), 1.50 (s, 3H), 1.12 (d, J=6.2 Hz, 3H), 0.89 (d, J=6.2 Hz, 3H), 0.85 (d, J=6.3 Hz, 3H).

Step 2: Van027 was prepared using the same needed materials, reagents and preparation method as those in example 16 except that Van-c in example 16 was replaced with Van-j. HRMS (ESI$^+$) calculated for $C_{87}H_{103}Cl_2N_{11}O_{30}$ [M+2H]$^{2+}$ 1851.6249, found 926.8124.

$^1$H NMR (600 MHz, DMSO-d$_6$) δ 8.79 (s, 11-1), 8.65 (d, J=6.0 Hz, 1H), 7.99 (s, 1H), 7.98-7.92 (m, 2H), 7.92-7.87

(m, 1H), 7.60 (s, 1H), 7.59-7.54 (m, 3H), 7.50 (s, 1H), 7.49-7.43 (m, 1H), 7.31 (d, J=8.3 Hz, 1H), 7.22 (d, J=8.4 Hz, 1H), 6.77 (d, J=8.5 Hz, 1H), 6.53 (s, 1H), 5.75-5.70 (m, 2H), 5.34 (d, J=7.7 Hz, 1H), 5.29 (d, J=4.2 Hz, 1H), 5.12 (d, J=4.4 Hz, 2H), 5.09 (d, J 1.9 Hz, 1H), 4.67 (q, J=6.6 Hz, 1H), 4.45 (d, J=5.7 Hz, 1H), 4.41 (d, J=5.7 Hz, 1H), 4.06 (s, 5H), 4.00 (d, J=3.6 Hz, 2H), 3.89 (t, J=2.9 Hz, 1H), 3.66 (d, J=10.7 Hz, 1H), 3.60-3.49 (m, 4H), 3.38-3.33 (m, 1H), 3.31-3.22 (m, 2H), 3.16 (dp, J=26.2, 6.6 Hz, 2H), 2.92 (t, J=7.5 Hz, 2H), 2.57 (s, 3H), 2.11 (d, J=10.9 Hz, 2H), 1.82 (dq, J=14.2, 7.0, 6.1 Hz, 3H), 1.69-1.60 (m, 2H), 1.51 (s, 3H), 1.12 (d, J=6.4 Hz, 3H). 0.91 (d, J=6.1 Hz, 3H), 0.85 (d, J=6.0 Hz, 3H).

Example 28

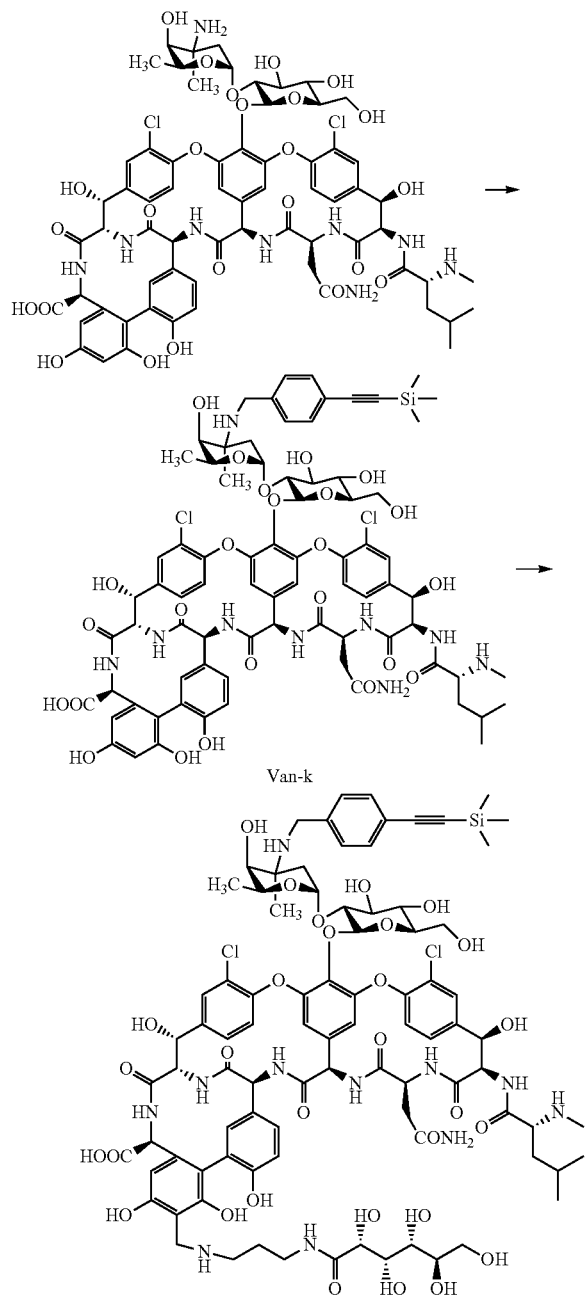

Step 1: Commercially available vancomycin (100 mg) and DIPEA (30 μL) were dissolved in 3 mL of DMF to give an opaque solution, which was heated to 50° C. to become clear. 4-((trimethylsilyl)ethynyl)benzaldehyde (27 mg) was added, and the mixture was heated under stirring for 4 h. NaCNBH$_3$ (8 mg), 1 mL of methanol and 30 μL of TFA were added at room temperature, and the reaction was stirred overnight and monitored by HPLC. The reaction mixture was added with diethyl ether (50 mL) to generate precipitates, which was filtered to give a crude. The crude was purified by reverse-phase C18 HPLC and lyophilized to give Van-k (40 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for $C_{78}H_{89}Cl_2N_9O_{24}Si$ [M+2H]$^{2+}$ 1633.5167, found 817.7670.

$^1$H NMR (600 MHz, DMSO-d$_6$) δ 8.70 (s, 1H), 7.82 (d, J=1.8 Hz, 1H), 7.51 (dd, J=19.0, 8.3 Hz, 4H), 7.45 (td, J=4.8, 2.1 Hz, 3H), 7.31 (d, J=8.4 Hz, 1H), 7.18 (d, J=8.4 Hz, 1H), 7.16-7.12 (m, 1H), 6.76 (dd, J=8.4, 2.0 Hz, 1H), 6.70 (d, J=8.5 Hz, 2H), 6.38 (d, J=2.3 Hz, 1H), 6.23 (d, J=2.3 Hz, 1H), 5.73 (d, J=7.8 Hz, 1H), 5.61 (s. 1H), 5.32 (d, J=7.6 Hz. 1H), 5.27 (d, J=4.2 Hz, 11-1), 5.15 (dd, J=11.8, 2.8 Hz, 2H), 5.09 (s, 1H), 4.90 (s, 1H), 4.65 (d, J=6.7 Hz, 1H), 4.42 (dd, J=15.8, 5.5 Hz, 2H), 3.96 (d, J=22.9 Hz, 3H), 3.66 (d, J=10.7 Hz, 1H), 3.56 (t, J=8.5 Hz, 1H), 3.30-3.21 (m, 3H), 2.61 (s, 3H), 2.09 (s, 3H), 1.80 (d, J=13.2 Hz, 1H), 1.64 (ddt, J=27.3, 12.8, 6.5 Hz, 3H), 1.54 (dt, J=13.2, 6.9 Hz, 21-1), 1.45 (s, 3H), 1.10 (d, J=6.2 Hz, 3H), 0.89 (d, J=6.2 Hz, 3H), 0.84 (d, J=6.2 Hz, 3H), 0.21 (s, 91-1).

Step 2: Van028 was prepared using the same needed materials, reagents and preparation method as those in example 16 except that Van-c in example 16 was replaced with Van-k. HRMS (ESI$^+$) calculated for $C_{88}H_{109}Cl_2N_{11}O_{30}Si$ [M+2H]$^{2+}$ 1897.6488, found 949.8331.

$^1$H NMR (600 MHz, DMSO-d$_6$) δ 8.78 (s, 1H), 8.65 (s, 1H), 7.61 (s, 1H), 7.50 (d, J=7.9 Hz, 3H), 7.46-7.43 (m, 2H), 7.30 (d, J=8.3 Hz, 1H), 7.21 (d, J=8.4 Hz, 1H), 6.84 (dd, J=8.4, 1.9 Hz, 1H), 6.77 (d, J=8.5 Hz, 2H), 6.53 (s, 1H), 5.72 (d, J=10.8 Hz, 2H), 5.32 (d, J=7.7 Hz, 1H), 5.28 (d, J=4.2 Hz, 1H), 5.12 (s, 2H), 5.08 (d, J=1.9 Hz, 1H), 4.80 (s, 1H), 4.64 (q, J=6.5 Hz, 2H), 4.44 (d, J=5.4 Hz, 1H), 4.41 (d, J=5.7 Hz, 1H), 3.89 (dd, J=3.6, 2.3 Hz, 1H), 3.66 (d, J=10.7 Hz, 1H), 3.59-3.52 (m, 3H), 3.39-3.32 (m, 2H), 3.29-3.22 (m, 3H), 3.16 (dq, J=25.9, 6.8 Hz, 3H), 2.92 (t, J=7.5 Hz, 21-1), 2.56 (s, 3H), 2.09 (s, 3H), 1.82 (td, J=15.9, 14.8, 8.3 Hz, 4H), 1.64 (q, J=6.7, 4.2 Hz, 2H), 1.46 (s, 51-1), 1.09 (d, J=6.3 Hz, 3H), 0.90 (d, J==6.0 Hz, 3H), 0.85 (d, J=6.1 Hz, 3H), 0.21 (s, 9H).

Example 29

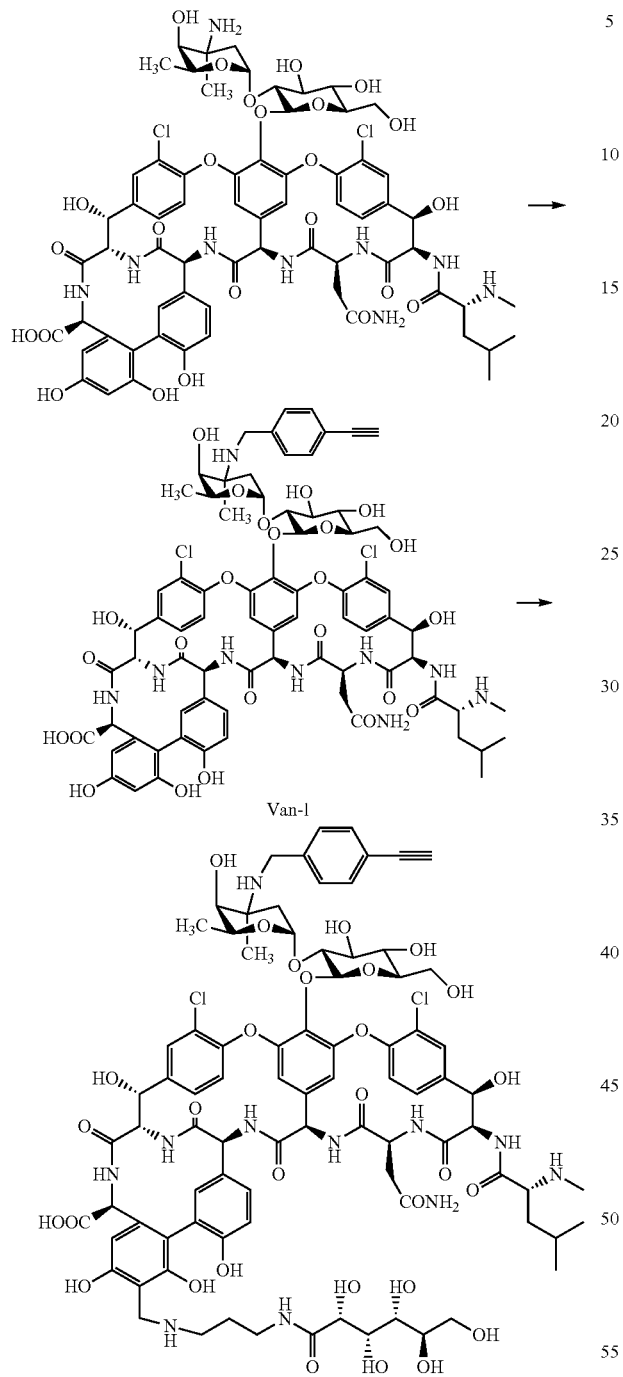

Van-1

Step 1: Commercially available vancomycin (100 mg) and DIPEA (30 μL) were dissolved in 3 mL of DMF to give an opaque solution, which was heated to 50° C. to become clear. 4-ethynylbenzaldehyde (24 mg) was added, and the mixture was heated under stirring for 4 h. NaCNBH$_3$ (8 mg), 1 mL of methanol and 30 μL of TFA were added at room temperature, and the reaction was stirred overnight and monitored by HPLC. The reaction mixture was added with diethyl ether (50 mL) to generate precipitates, which was filtered to give a crude. The crude was purified by reverse-phase C18 HPLC and lyophilized to give Van-1 (40 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for $C_{75}H_{81}Cl_2N_9O_{24}$ $[M+2H]^{2+}$ 1561.4771, found 781.7473.

$^1$H NMR (600 MHz, DMSO-d$_6$) 7.57-7.51 (m, 3H), 7.48 (dd, J=9.2, 4.0 Hz, 3H), 7.33 (d, J=8.4 Hz, 1H), 7.21 (d, J=8.3 Hz. 1H), 7.16 (s, 1H), 6.78 (dd, J=8.5, 2.0 Hz, 1H), 6.72 (d, J=8.7 Hz, 1H), 5.76 (d, J=7.3 Hz, 1H), 5.66-5.59 (m, 1H), 5.34 (d, J=7.7 Hz, 1H), 5.29 (d, J=4.4 Hz, 1H), 5.20-5.13 (m, 2H), 5.11 (s, 1H), 4.92 (s, 1H). 4.67 (t, J=6.6 Hz, 1H), 4.44 (dd, J=15.6, 5.6 Hz, 1H), 4.25 (d, J=2.9 Hz, 1H), 4.19 (s, 1H). 3.68 (d, J=10.7 Hz, 1H), 3.58 (t, J=8.5 Hz, 1H), 3.55-3.49 (m. 1H), 3.31-3.23 (m, 2H), 2.62 (s, 3H), 2.19-2.05 (m, 2H), 1.82 (d, J=13.3 Hz, 1H), 1.72-1.60 (m, 2H), 1.57 (dd, J=12.7, 6.3 Hz, 1H), 1.48 (d, J=8.6 Hz, 3H), 1.28-1.21 (m, 1H), 1.12 (d, J=6.4 Hz, 3H), 0.92 (d, J=6.2 Hz, 3H), 0.87 (d, J=6.2 Hz, 3H).

Step 2: Van029 was prepared using the same needed materials, reagents and preparation method as those in example 16 except that Van-c in example 16 was replaced with Van-1. HRMS (ESI$^+$) calculated for $C_{85}H_{101}Cl_2N_{11}O_{30}$ $[M+2H]^{2+}$ 1825.6093, found 913.8131.

$^1$H NMR (600 MHz, DMSO-d$_6$) δ 8.79 (s, 1H), 8.65 (s, 1H), 7.61 (s, 1H), 7.52 (d, J=7.8 Hz, 2H), 7.50-7.42 (m, 4H), 7.30 (d, J=8.3 Hz, 1H), 7.21 (d, J=8.4 Hz, 1H), 6.84 (dd, J=8.4, 1.9 Hz, 1H), 6.77 (d, J=8.5 Hz, 1H), 6.53 (s, 1H), 5.72 (d, J=10.5 Hz, 2H), 5.32 (d, J=7.7 Hz, 1H), 5.28 (d, J=4.1 Hz, 1H), 5.12 (d, J=3.5 Hz, 2H), 5.08 (d, J=2.0 Hz, 1H), 4.64 (d, J=6.7 Hz, 1H), 4.44 (d, J=5.4 Hz, 1H), 4.41 (d, J=5.7 Hz, 1H), 4.25-4.21 (m, 1H), 4.07 (d, J=16.7 Hz, 4H), 4.02-3.94 (m, 4H), 3.89 (t, J=2.8 Hz, 1H), 3.66 (d, J=10.6 Hz, 1H), 3.58-3.51 (m, 3H), 3.36 (dd, J=10.8, 5.3 Hz, 1H), 3.26 (s, 2H), 3.16 (dq, J=26.0, 6.8 Hz, 2H), 2.92 (t, J=7.3 Hz, 2H), 2.56 (s, 3H), 2.08 (s, 2H), 1.82 (td, J=14.1, 7.6 Hz, 3H), 1.69-1.60 (m, 2H), 1.45 (s, 4H), 1.09 (d, J=6.3 Hz, 3H), 0.91 (d, J=6.0 Hz, 3H), 0.85 (d, J=6.0 Hz, 3H).

Example 30

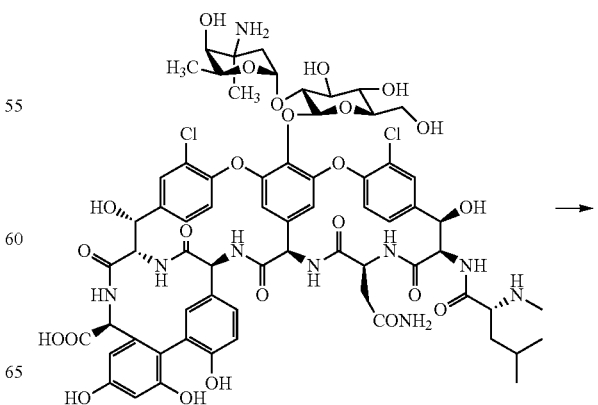

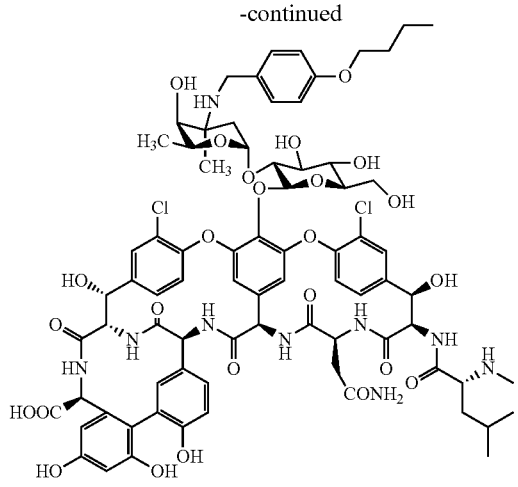

Van-m

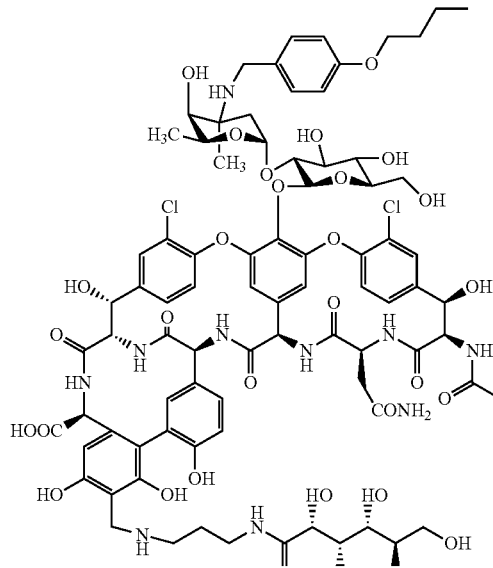

Step 1: commercially available vancomycin (100 mg) and DIPEA (30 μL) were dissolved in 3 mL of DMF to give an opaque solution, which was heated to 50° C. to become clear. 4-butoxybenzaldehyde (24 μL) was added and the mixture was heated under stirring for 4 h. NaCNBH$_3$ (8 mg), 1 mL of methanol and 30 μL of TFA were added at room temperature, and the reaction was stirred overnight and monitored by HPLC. The reaction mixture was added with diethyl ether (50 mL) to generate precipitates, which was filtered to give a crude. The crude was purified by reverse-phase C18 HPLC, lyophilized to give Van-m (40 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI$^+$) calculated for $C_{77}H_{88}Cl_2N_9O_{25}$ [M+2H]$^{2+}$ 1609.5347, found 805.7758.

$^1$H NMR (600 MHz, DMSO-d$_6$) δ 8.72 (s. 1H), 7.85 (d, J=1.9 Hz, 1H), 7.47 (dd, J=8.3, 1.8 Hz, 1H), 7.38-7.34 (m, 2H), 7.33 (d, J=8.4 Hz, 1H), 7.22 (d, J=8.3 Hz, 1H), 6.96 (d, J=8.6 Hz, 2H), 6.78 (dd, J=8.4, 2.0 Hz, 1H), 6.72 (d, J=8.6 Hz, 2H), 6.40 (d, J=2.3 Hz, 1H), 6.25 (d, J=2.3 Hz, 1H), 5.76 (d, J=5.2 Hz, 1H), 5.62 (s, 1H), 5.35 (d, J=7.8 Hz, 1H), 5.28 (d, J=4.3 Hz, 1H), 5.18 (dd, J=7.4, 2.9 Hz, 2H), 5.11 (s, 1H), 4.92 (s, 1H), 4.66 (q, J=6.5 Hz, 1H), 4.45 (d, J=5.5 Hz, 1H), 4.43 (d, J=5.8 Hz, 1H), 4.19 (s, 1H), 3.97 (t, J=6.5 Hz, 2H), 3.92 (q, J=12.6 Hz, 3H), 3.68 (d, J=10.7 Hz, 1H), 3.58 (t, J=8.5 Hz, 1H), 3.52 (dd, J=11.0, 4.3 Hz, 1H), 3.32-3.23 (m, 3H), 3.09 (q, J=7.3 Hz, 2H), 2.59 (s, 3H), 2.11 (s, 3H), 1.80 (d, J=13.2 Hz, 1H), 1.71-1.62 (m, 4H), 1.54 (s, 2H), 1.47 (s, 2H), 1.45-1.38 (m, 3H), 1.17 (t, J=7.3 Hz, 3H), 1.12 (d, J=6.2 Hz, 3H), 0.96-0.89 (m, 6H), 0.86 (d, J=6.0 Hz, 3H).

Step 2: Van030 was prepared using the same needed materials, reagents and preparation method as those in example 16 except that Van-c in example 16 was replaced with Van-m. HRMS (ESI$^±$) calculated for $C_{87}H_{109}Cl_2N_{11}O_{31}$ [M+2H]$^{2+}$ 1873.6668, found 937.8422.

$^1$H NMR (600 MHz, DMSO-d$_6$) δ 7.84 (s, 1H), 7.61 (s, 1H), 7.52-7.49 (m, 1H), 7.48 (dd, J=8.3, 1.8 Hz, 1H), 7.36 (d, J=8.4 Hz, 2H), 7.32 (d, J=8.4 Hz, 1H), 7.23 (d, J=8.4 Hz, 1H), 7.12 (s, 1H), 6.96 (d, J=8.5 Hz, 2H), 6.86 (dd, J=8.5, 2.0 Hz, 1H). 6.79 (d, J=8.5 Hz, 1H), 6.54 (s, 1H), 5.72 (d, J=12.4 Hz, 2H), 5.35 (d, J=7.6 Hz, 1H), 5.29 (d, J=4.2 Hz, 1H), 5.14 (s, 2H), 5.11 (d, J=2.0 Hz, 1H), 4.82 (s, 1H), 4.66 (q, J=6.6 Hz, 1H), 4.46 (d, J=5.5 Hz, 1H), 4.43 (d, J=6.1 Hz, 1H), 4.10 (d, J=28.9 Hz, 3H), 4.02 (d, J=3.6 Hz, 1H), 3.97 (t, J=6.5 Hz, 3H), 3.91 (dd, J=8.5, 6.0 Hz, 3H), 3.68 (d, J=10.6 Hz, 1H), 3.60-3.55 (m, 3H), 3.55-3.50 (m, 2H), 3.44 (s, 2H), 3.40-3.36 (m, 1H), 3.31-3.24 (m, 2H), 3.18 (ddq, J=31.3, 13.3, 6.4 Hz, 3H), 2.92 (s, 2H), 2.56 (s, 2H), 2.16-2.07 (m, 2H), 1.83 (tt, J=13.7, 6.9 Hz, 3H), 1.67 (td, J=12.1, 10.5, 6.1 Hz, 4H), 1.47 (s, 3H), 1.41 (dt, J=14.7, 7.5 Hz, 3H), 1.11 (d, J=6.3 Hz, 3H), 0.94-0.90 (m, 6H), 0.87 (d, J=6.2 Hz, 3H).

Example 31

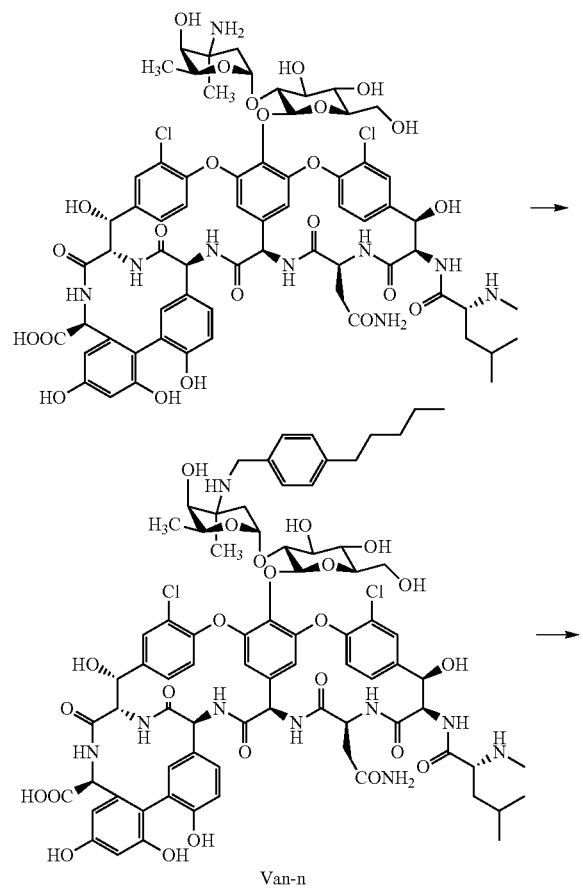

Van-n

-continued

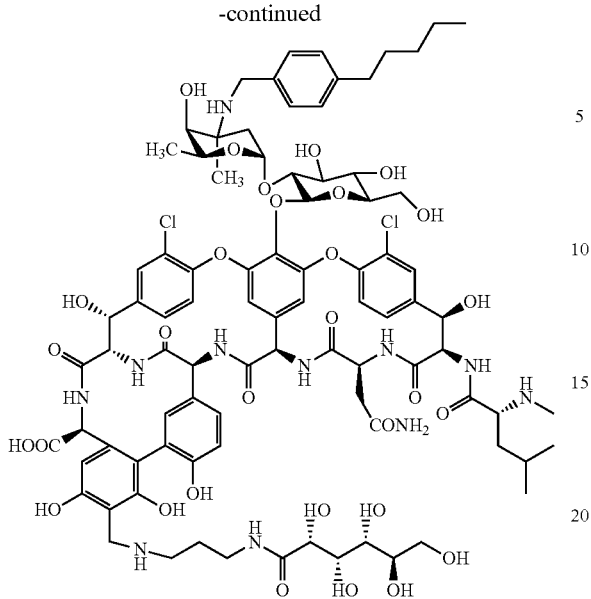

Step 1: Commercially available vancomycin (100 mg) and DIPEA (30 μL) were dissolved in 3 mL of DMF to give an opaque solution, which was heated to 50° C. to become clear. 4-pentylbenzaldehyde (24 μL) was added, and the mixture was heated under stirring for 4 h. NaCNBH₃ (8 mg), 1 mL of methanol and 30 μL of TFA were added at room temperature, and the reaction was stirred overnight and monitored by HPLC. The reaction mixture was added with diethyl ether (50 mL) to generate precipitates, which was filtered to give a crude. The crude was purified by reverse-phase C18 HPLC and lyophilized to give Van-n (40 mg) as a white solid. HPLC: C18 column (5 μm, 4.6×250 mm), UV detection at 214 nm, elution conditions: a gradient of 2-90% acetonitrile containing 0.1% v/v TFA over 30 min. HRMS (ESI⁺) calculated for $C_{78}H_{91}Cl_2N_9O_{24}$ $[M+2H]^{2+}$ 1607.5554, found 804.7777.

¹H NMR (600 MHz, DMSO-d₆) δ 8.56 (d, J=5.8 Hz, 1H), 7.85 (d, J=1.9 Hz, 1H), 7.57-7.53 (m, 1H), 7.47 (dd, J=8.3, 1.8 Hz, 1H), 7.36 (d, J=7.8 Hz, 2H), 7.33 (d, J=8.3 Hz, 1H), 7.24 (d, J=8.1 Hz, 2H), 7.20 (d, J=8.4 Hz, 1H), 7.16 (s, 1H), 6.78 (dd, J=8.4, 2.0 Hz, 1H), 6.72 (d, J=8.5 Hz, 2H), 6.40 (d, J=2.3 Hz, 1H), 6.25 (d, J=2.3 Hz, 1H), 5.76 (d, J=7.9 Hz, 1H), 5.63 (s, 1H), 5.35 (d, J=7.8 Hz, 1H), 5.28 (d, J=4.2 Hz, 1H), 5.19 (d, J=3.6 Hz, 1H), 5.17 (d, J=2.0 Hz, 1H), 5.11 (s, 1H), 4.92 (s, 1H), 4.66 (d, J=6.6 Hz, 1H), 4.45 (d, J=5.4 Hz, 1H), 4.43 (d, J=5.7 Hz, 1H), 4.20 (s, 2H), 3.96 (s, 4H), 3.68 (d, J=10.7 Hz, 1H), 3.58 (t, J=8.5 Hz, 1H), 3.28 (h, J=7.9, 7.4 Hz, 2H), 2.63 (s, 3H), 2.57 (t, J=7.6 Hz, 2H), 2.11 (d, J=11.1 Hz, 2H), 1.81 (d, J=13.2 Hz, 1H), 1.71-1.60 (m, 3H), 1.55 (h, J=7.5 Hz, 4H), 1.47 (s, 3H), 1.32-1.19 (m, 5H), 1.12 (d, J=6.3 Hz, 3H), 0.91 (d, J=6.2 Hz, 3H), 0.86 (d, J=6.9 Hz, 3H), 0.84 (d, J=7.2 Hz, 3H).

Step 2: Van031 was prepared using the same needed materials, reagents and preparation method as those in example 16 except that Van-c in example 16 was replaced with Van-n. HRMS (ESI⁺) calculated for $C_{89}H_{111}Cl_2N_{11}O_{30}$ $[M+2H]^{2+}$ 1871.6875, found 936.8522.

¹H NMR (600 MHz, DMSO-d₆) δ 8.80 (s, 1H), 8.67 (s, 1H), 7.85-7.83 (m, 1H), 7.62 (s, 1H), 7.52-7.49 (m, 1H), 7.48 (dd, J=8.3, 1.7 Hz, 1H), 7.36 (d, J=8.0 Hz, 2H), 7.32 (d, J=8.3 Hz, 1H), 7.24 (d, J=7.7 Hz, 3H), 7.12 (s, 1H), 6.86 (dd, J=8.6, 1.8 Hz, 1H), 6.79 (d, J=8.6 Hz, 1H), 6.54 (s, 1H), 5.75-5.71 (m, 2H), 5.35 (d, J=7.7 Hz, 1H), 5.30 (d, J=4.1 Hz, 1H), 5.14 (s, 2H), 5.11 (d, J=2.0 Hz, 1H), 4.82 (s, 1H), 4.66 (t, J=6.5 Hz, 1H), 4.46 (d, J=5.7 Hz, 1H), 4.43 (d, J=5.9 Hz, 1H), 4.07 (s, 4H), 4.02 (d, J=3.6 Hz, 1H), 3.98-3.93 (m, 21-1), 3.92-3.90 (m, 1H), 3.68 (d, J=10.5 Hz, 1H), 3.59-3.55 (m, 3H), 3.54-3.49 (m, 3H), 3.40-3.36 (m, 1H), 3.30-3.23 (m, 2H), 3.18 (dq, I=25.5, 6.9 Hz, 211), 2.93 (s, 1H), 2.57 (d, J=7.1 Hz, 5H), 2.12 (d, J=20.5 Hz, 2H), 1.86-1.78 (m, 3H), 1.66 (s, 2H), 1.55 (p, J=7.5 Hz, 3H), 1.48 (s, 3H), 1.31-1.22 (m, 5H), 1.11 (d, J=6.3 Hz, 3H), 0.92 (d, J=6.1 Hz, 3H), 0.87 (d, j=6.1 Hz, 3H), 0.85 (t, J=7.1 Hz, 3H).

Example 32

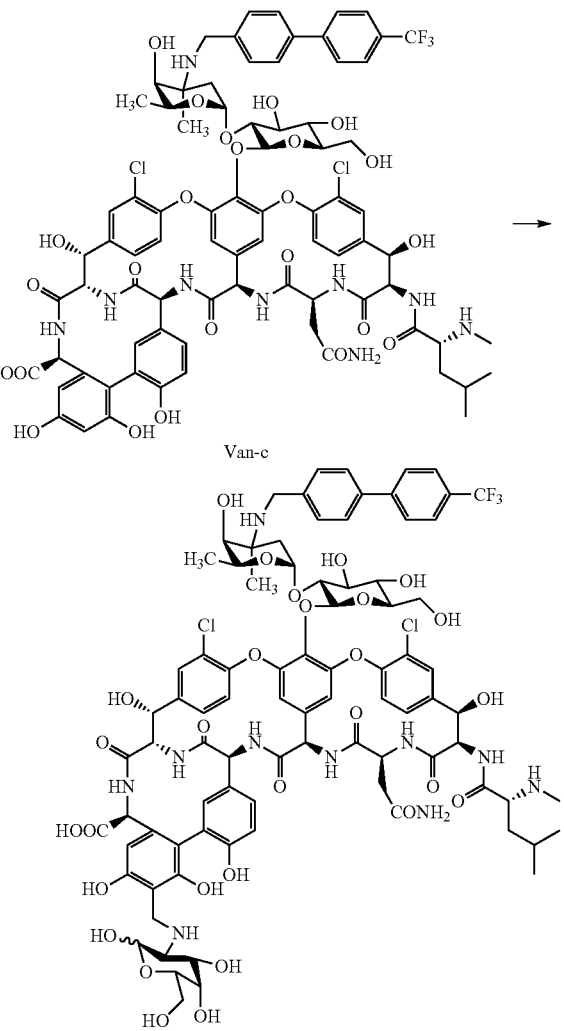

Van032 was prepared using the same needed materials, reagents and preparation method as those in example 8 except that $N^{van}$-2-(n-decylamine)ethyl-vancomycin (Van-a) in example 8 was replaced with $N^{van}$-2-(4'-trifluoromethyl-biphenylmethyl)-vancomycin (Van-c). HRMS (ESI) calculated for $C_{87}H_{97}Cl_2F_3N_{10}O_{29}$ $[M+2H]^{2+}$ 1872.5752, found 937.2960.

¹H NMR (600 MHz, DMSO-d₆) δ 8.83 (s, 1H), 7.92 (d, J=8.1 Hz, 2H), 7.84 (d, J=8.5 Hz, 3H), 7.84-7.79 (m, 2H), 7.62 (t, J=10.7 Hz, 3H), 7.54-7.44 (m, 2H), 7.33 (d, J=8.3 Hz, 1H), 7.23 (dd, J=8.4, 3.1 Hz, 1H), 7.16 (s, 1H), 6.90-

6.85 (m, 1H), 6.79 (t, J=9.0 Hz, 1H). 6.55 (d, J=4.7 Hz, 1H), 5.74 (d, J=9.7 Hz, 2H), 5.53 (d, J=3.5 Hz, 1H), 5.36 (d, J=7.7 Hz, 1H), 5.31 (s, 1H), 5.19-5.07 (m, 3H), 4.83 (s, 1H), 4.68 (d, J=6.9 Hz, 1H), 4.50 (s, 1H), 4.43 (t, J=5.8 Hz. 1H), 4.27 (d, J=15.9 Hz, 1H), 4.08 (d, J=14.2 Hz, 2H), 4.03 (d, J=8.3 Hz, 1H), 3.90-3.83 (m, 1H), 3.82 (t, J=6.5 Hz, 1H), 3.58 (t, J=8.5 Hz, 2H), 3.53 (dt, J=10.6, 4.4 Hz, 3H), 3.29 (s, 2H), 2.75 (s, 1H). 2.59 (s, 3H), 2.13 (d, J=13.0 Hz, 2H), 1.84 (d, J=13.2 Hz, 1H), 1.51 (s, 4H), 1.13 (d, J=6.3 Hz, 3H), 0.93 (d, J=6.0 Hz, 3H), 0.88 (d, J=6.1 Hz, 3H).

Example 33

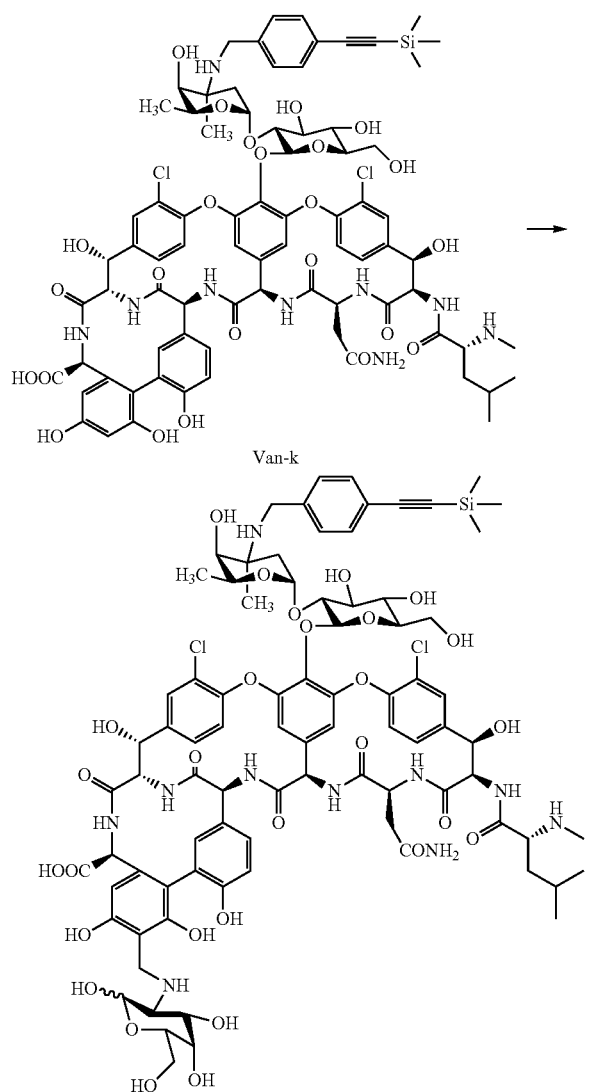

Van-k

Van033 was prepared using the same needed materials, reagents and preparation method as those in example 8 except that $N^{van}$-2-(n-decylamine)ethyl-vancomycin (Van-a) in example 8 was replaced with $N^{van}$-2-(4-((trimethylsilyl)ethynyl)benzyl)-vancomycin (Van-k). FIRMS (ESI$^+$) calculated for $C_{85}H_{102}Cl_2N_{10}O_{29}Si$ [M+2H]$^{2+}$ 1824.5960. found 913.3060.

$^1$H NMR (600 MHz, DMSO-d$_6$) δ 8.80 (s, 1H), 8.71 (s, 1H), 7.82 (d, J=8.1 Hz, 1H), 7.62 (s, 1H), 7.53-7.47 (m, 3H), 7.45 (d, J=7.7 Hz, 3H), 7.30 (d, J=8.3 Hz, 1H), 7.19 (d, J=8.3 Hz, 1H), 7.13 (s, 1H), 6.86 (d, J=8.9 Hz, 1H), 6.76 (d, J=8.5 Hz, 2H), 6.53 (d, J=4.6 Hz, 1H), 5.71 (s, 2H), 5.33 (d, J=7.7 Hz, 1H), 5.28 (s, 1H), 5.16-5.06 (m, 3H), 4.80 (s, 1H), 4.65 (d, J=6.8 Hz, 1H), 4.48 (s, 1H), 4.40 (t, J=5.9 Hz, 1H), 4.23 (s, 1H), 4.16-3.91 (m, 5H), 3.84 (d, J=10.9 Hz, OH), 3.80 (t, J=6.5 Hz, 1H), 3.73-3.63 (m, 1H), 3.55 (t, J=8.5 Hz, 1H), 3.50 (d, J=10.0 Hz, 2H), 3.26 (s, 2H), 2.72 (s, 1H), 2.57 (s, 3H), 2.17-2.03 (m, 2H), 1.80 (d, J=13.2 Hz, 1H), 1.64 (d, J=9.8 Hz, 2H), 1.46 (s, 3H), 1.21 (s, 1H), 1.09 (d, J=6.3 Hz, 3H), 0.91 (d, J=6.0 Hz, 3H), 0.86 (d, J=6.1 Hz, 3H), 0.21 (s, 9H).

Example 34

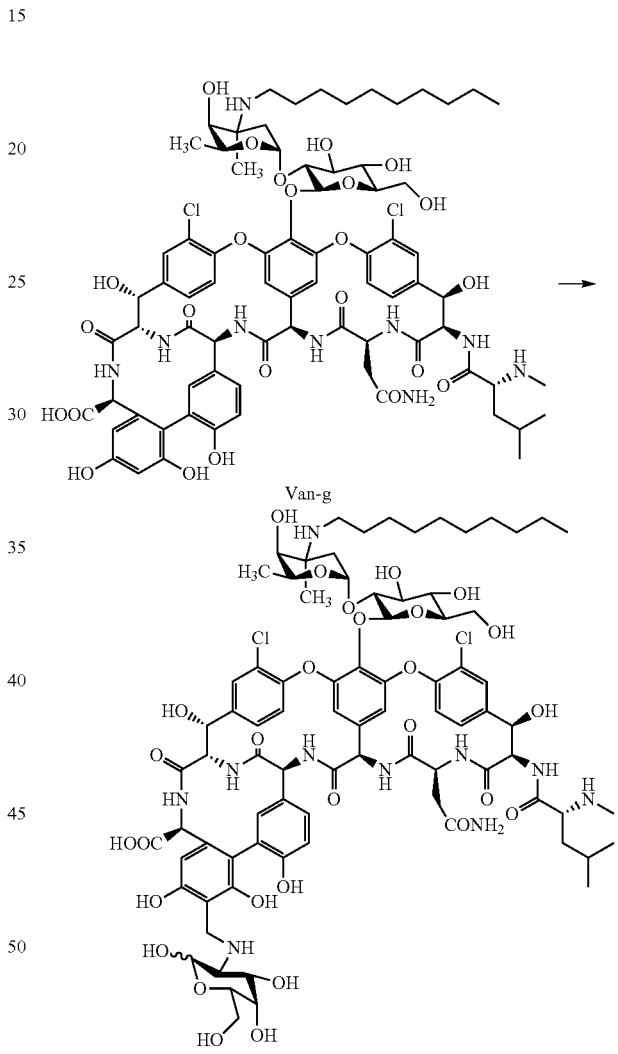

Van-g

Van034 was prepared using the same needed materials, reagents and preparation method as those in example 8 except that $N^{van}$-2-(n-decylamine)ethyl-vancomycin (Van-a) in example 8 was replaced with $N^{van}$-2-(decyl)-vancomycin (Van-g). HRMS (ESI$^+$) calculated for $C_{83}H_{108}Cl_2N_{10}O_{29}$ [M+2H]$^{2+}$ 1778.6661, found 890.3400.

$^1$H NMR (600 MHz, DMSO-d$_6$) δ 8.81 (s, 1H), 8.73 (s, OH), 7.83 (d, J=7.7 Hz, 1H), 7.62 (s, 1H), 7.50 (d, J=8.7 Hz, 1H), 7.47 (d, J=8.4 Hz, 1H), 7.31 (d, J=8.3 Hz, 1H), 7.20 (d, J=7.9 Hz, 1H), 7.15 (s, 1H), 6.87 (d, J=8.7 Hz, 1H), 6.78 (dd, J=8.5, 2.5 Hz, 1H), 6.55 (s, 1H), 5.76-5.68 (m, 1H), 5.32 (d, J=7.7 Hz, 1H), 5.29 (d, J=4.1 Hz, 1H), 5.17-5.05 (m, 2H), 4.82 (s, 1H), 4.61 (d, J=6.9 Hz, 1H), 4.42 (t, J=6.0 Hz, 1H), 4.25 (s, 1H), 4.18-3.94 (m, 3H), 3.86 (d, J=10.3 Hz, 0H), 3.82 (t, J=6.5 Hz, 0H), 3.67 (d, J=10.9 Hz, 1H), 3.56 (t, J=8.5 Hz, 1H), 3.52 (d, J=9.6 Hz, 2H), 3.44 (d, J=8.4 Hz, 3H), 3.27 (d, J=9.8 Hz, 3H), 2.73 (d, J=38.7 Hz, 2H), 2.58 (s, 2H), 2.14 (s, 1H), 1.98 (d, J=11.8 Hz, 1H), 1.79 (d, J=13.1 Hz, 1H), 1.66 (s, 2H), 1.35 (s, 3H), 1.24 (s, 15H), 1.08 (d, J=6.2 Hz, 3H), 0.93 (d, J=6.0 Hz, 3H), 0.89-0.83 (m, 6H).

Example 35

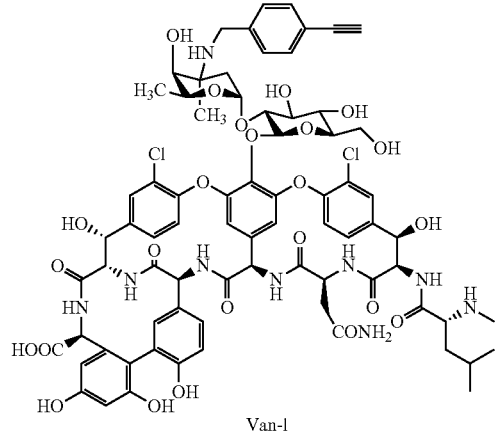

Van-l 3.47 (d, J=8.6 Hz, 1H), 3.37 (d, J=8.9 Hz, 2H), 3.32-3.22 (m, 3H), 2.59 (s, 3H), 2.20-2.05 (m, 2H), 1.82 (d, J=13.2 Hz, 1H), 1.67 (d, J=9.3 Hz, 2H), 1.48 (s, 3H), 1.12 (d, J=6.3 Hz, 3H), 0.93 (d, J=6.0 Hz, 3H), 0.88 (d, J=6.1 Hz, 3H).

Example 36

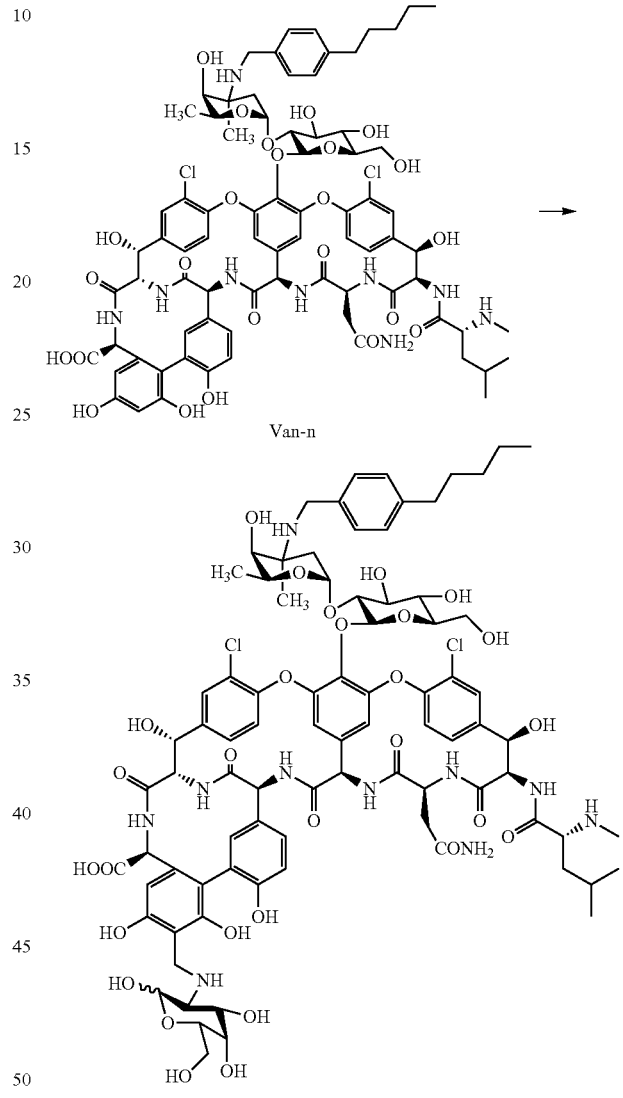

Van-n

Van035 was prepared using the same needed materials, reagents and preparation method as those in example 8 except that N$^{van}$-2-(n-decylamine)ethyl-vancomycin (Van-a) in example 8 was replaced with N$^{van}$-2-(4-ethynylbenzyl)-vancomycin (Van-l). FIRMS (ESI) calculated for $C_{82}H_{94}Cl_2N_{10}O_{29}$ [M+2H]$^{2+}$ 1752.5565, found 877.2869.

$^1$H NMR (600 MHz, DMSO-d$_6$) δ 8.81 (s, 1H), 7.85 (d, J=8.0 Hz, 1H), 7.63 (s, 1H). 7.55 (d, J=8.0 Hz, 2H), 7.50 (t, J=11.3 Hz, 4H), 7.33 (d, J=8.3 Hz, 1H), 7.22 (dd, J=8.6, 3.8 Hz, 1H), 6.87 (s, 1H), 6.79 (dd, I=10.3, 6.2 Hz, 1H), 5.74 (d, J=9.4 Hz, 2H), 5.35 (d, J=7.6 Hz, 1H), 5.30 (d, J=4.2 Hz, 1H), 5.19-5.06 (m, 3H), 4.83 (s, 1H), 4.67 (d, J=7.0 Hz, 1H), 4.43 (q, J=6.1 Hz, 1H), 4.27 (d, J=1.9 Hz, 2H), 3.69 (d, J=10.7 Hz, 1H), 3.58 (t, J=8.5 Hz, 1H), 3.55-3.49 (m, 2H),

Van036 was prepared using the same needed materials, reagents and preparation method as those in example 8 except that N$^{van}$-2-(n-decylamine)ethyl-vancomycin (Van-a) in example 8 was replaced with N$^{van}$-2-(4-pentylbenzyl)-vancomycin (Van-n). HRMS (ESI$^+$) calculated for $C_{85}H_{104}Cl_2N_{10}O_{29}$ [M+2H]$^{2+}$ 1798.6348, found 900.3265.

$^1$H NMR (600 MHz, DMSO-d$_6$) δ 8.80 (s, 1H), 8.72 (s, 1H), 7.82 (d, J=7.5 Hz, 1H), 7.61 (s, 1H), 7.49 (d, J=8.8 Hz, 1H), 7.46 (d, J=8.4 Hz, 1H), 7.34 (d, J=7.8 Hz, 2H), 7.30 (d, J=8.3 Hz, 1H), 7.21 (dd, J=15.1, 8.1 Hz, 3H), 6.85 (d, J=8.3 Hz, 1H), 6.77 (dd, J=10.3, 6.2 Hz, 1H), 6.53 (d, J=4.5 Hz, 1H), 6.45 (s, 0H), 5.72 (d, J=9.0 Hz, 2H), 5.51 (d, J=3.5 Hz, 0H), 5.33 (d, J=7.6 Hz, 1H), 5.28 (s, 1H), 5.16-5.07 (m, 3H). 4.80 (s, 1H). 4.64 (d, J=6.6 Hz, 1H), 4.48 (s, 1H), 4.40 (t, J=5.9 Hz, 1H), 4.23 (s, 1H), 4.09 (d, J=41.4 Hz, 2H), 4.00

(s, 1H), 3.93 (q, J=12.7 Hz, 2H), 3.84 (d, J=11.7 Hz, 0H), 3.80 (t, J=6.5 Hz, 1H), 3.72-3.64 (m, 1H), 3.55 (t, J=8.5 Hz, 1H), 3.53-3.46 (m, 3H), 3.25 (d, J=9.5 Hz, 2H), 2.73 (s, 1H), 2.56 (dd, J=10.3, 4.8 Hz, 4H), 2.09 (d, J=12.0 Hz, 2H), 1.79 (d, J=13.2 Hz, 1H), 1.53 (p, J=7.5 Hz, 3H), 1.46 (s, 3H), 1.30-1.18 (m, 4H), 1.09 (d, J=6.3 Hz, 3H), 0.91 (d, J=6.1 Hz, 3H), 0.86 (d, J=6.1 Hz, 3H), 0.83 (t, J=7.1 Hz, 3H).

Hz, 1H), 4.43 (d, J=6.0 Hz, 1H), 4.14 (p, J=10.0, 7.2 Hz, 4H), 4.06 (s, 3H), 3.95 (s, 2H), 3.69 (d, J=10.7 Hz, 2H), 3.63 (d, J=3.0 Hz, 1H), 3.59 (t, J=8.5 Hz, 2H), 3.55-3.49 (m, 5H), 3.35-3.22 (m, 5H), 2.54 (d, J=5.7 Hz, 2H), 2.14 (d, J=16.3 Hz, 2H), 1.84 (d, J=13.2 Hz, 1H), 1.71-1.58 (m, 3H), 1.51 (s, 4H), 1.17 (t, J=7.3 Hz, 1H), 1.13 (d, J=6.2 Hz, 3H), 0.92 (d, J=6.2 Hz, 3H), 0.87 (d, J=6.3 Hz, 3H).

Example 37

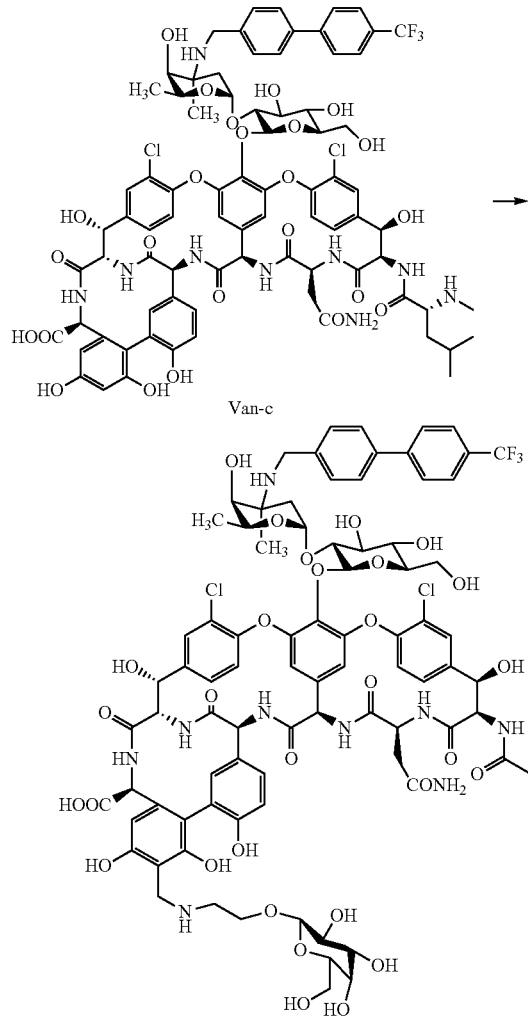

Example 38

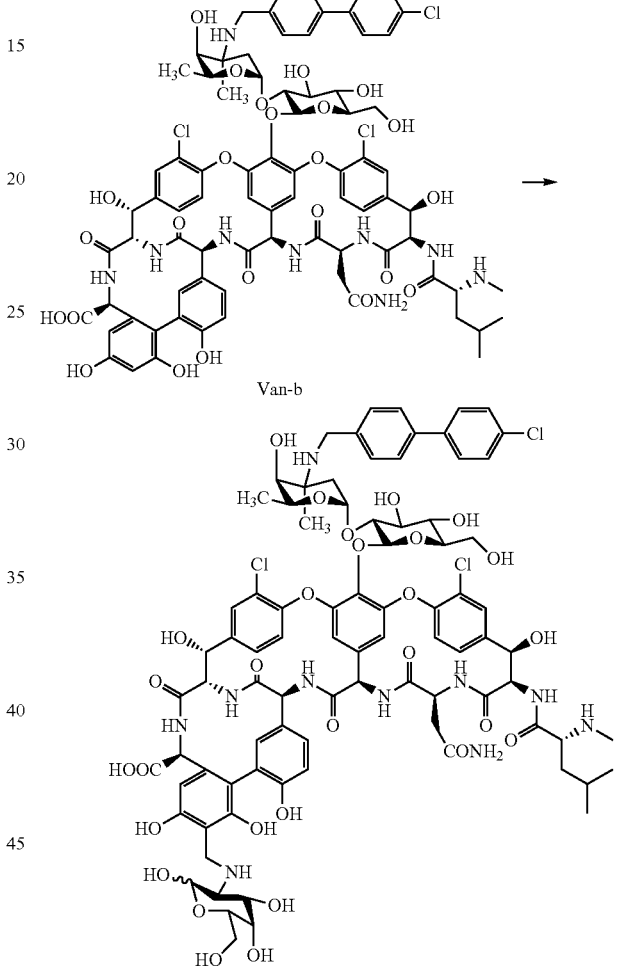

Van037 was prepared using the same needed materials, reagents and preparation method as those in example 2 except that $N^{van}$-2-(n-decylamine)ethyl-vancomycin (Van-a) in example 2 was replaced with $N^{van}$-2-(4'-trifluoromethyl-biphenylmethyl)-vancomycin (Van-c). HRMS (ESI$^+$) calculated for $C_{89}H_{101}Cl_2F_3N_{10}O_{30}$ [M+2H]$^{2+}$ 1916.6014, found 959.3086.

$^1$H NMR (600 MHz, DMSO-d$_6$) δ 8.79 (s, 1H), 7.92 (d, J=8.1 Hz, 2H), 7.84 (d, J=8.7 Hz, 3H), 7.82 (d, J=7.8 Hz, 2H), 7.61 (d, J=7.9 Hz, 3H), 7.52 (d, J=8.6 Hz, 1H), 7.49 (d, J=8.4 Hz, 1H), 7.33 (d, J=8.4 Hz, 1H), 7.25 (d, J=8.4 Hz, 1H), 7.15 (s, 1H), 6.86 (d, J=8.6 Hz, 1H), 6.78 (d, J=8.5 Hz, 1H), 6.51 (s, 1H), 5.75 (s, 1H), 5.70 (s, 1H), 5.37 (d, J=7.6 Hz, 1H), 5.31 (d, J=4.2 Hz, 1H), 5.14 (d, J=6.1 Hz, 3H), 4.83 (d, J=15.8 Hz, 1H), 4.69 (q, J=6.6 Hz, 1H), 4.47 (d, J=5.3

Van038 was prepared using the same needed materials, reagents and preparation method as those in example 8 except that $N^{van}$-2-(n-decylamine)ethyl-vancomycin (Van-a) in example 8 was replaced with $N^{van}$-2-(4'-chlorobiphenylmethyl)-vancomycin (Van-b). HRMS (ESI$^+$) calculated for $C_{86}H_{97}Cl_2N_{10}O_{29}$ [M+2H]$^2$ 1838.5489, found 920.2862.

$^1$H NMR (600 MHz, DMSO-d$_6$) δ 8.80 (s, 21-1), 8.72 (s, 2H), 7.85-7.81 (m, 1H), 7.75-7.67 (m, 4H), 7.61 (s, 2H), 7.58-7.53 (m, 3H), 7.52 (d, J=4.4 Hz, 2H), 7.51 (d, J=8.4 Hz, 1H), 7.46 (d, J=8.6 Hz, 2H), 7.31 (d, J=8.3 Hz, 1H), 7.20 (dd, J=8.4, 3.4 Hz, 1H), 6.86 (dd, J=8.4, 2.1 Hz, 1H), 6.77 (t, J=8.6 Hz, 2H), 6.53 (d, J=4.7 Hz, 1H), 5.72 (d, J=11.0 Hz, 2H), 5.51 (d, J=3.6 Hz, 1H), 5.33 (d, J=7.7 Hz, 1H), 5.29 (d, J=4.2 Hz, 2H), 5.16-5.07 (m, 3H), 4.80 (s, 1H), 4.66 (d, J=6.8 Hz, 2H), 4.48 (s, 1H), 4.40 (t, J=5.8 Hz, 2H), 4.23 (s, 1H), 4.05-3.97 (m, 3H), 3.86-3.81 (m, 1H), 3.79 (d, J=6.5

Hz, 1H), 3.75 (d, J=3.2 Hz, 1H), 3.66 (d, J=10.8 Hz, 2H), 3.56 (t, J=8.5 Hz, 2H), 3.42-3.37 (m, 2H), 3.29-3.23 (m, 2H), 3.15 (dd, J=10.5, 3.5 Hz, 1H), 2.71 (s, 214), 2.57 (s, 3H), 2.10 (d, J=12.8 Hz, 3H), 1.82 (d, J=13.2 Hz, 1H), 1.65 (s, 3H), 1.49 (s, 4H), 1.26-1.19 (m, 2H), 1.10 (d, J=6.3 Hz, 3H), 0.91 (d, J=6.0 Hz, 3H), 0.86 (d, J=6.1 Hz, 3H).

Activity Assay:

Biological Test Example 1 In Vitro Antibacterial Activity Assay 38 compounds of the present invention were subjected to in vitro antibacterial activity assay. The antimicrobial concentrations (Minimal Inhibitory concentration, MIC) of the vancomycin derivatives were measured according to the Clinical Laboratory Standardization Association (CLSI) 2006 reference method for dilution, and the results were shown in Table 1.

The vancomycin-sensitive Staphylococcus aureus Newman strain (Newman) and vancomycin-middle resistant Staphylococcus aureus Mu50 strain (Mu50) were selected as the strains to perform the assay.

Vancomycin was purchased from Wuhan Dahua Pharmaceutical Co., Ltd., batch number DH20160105, and telavancin was prepared according to the method described in US20020022590 A1.

Test method: The compounds to be tested were dissolved in DMSO to prepare a stock solution at 1.28 mg/mL, which was then diluted with DMSO to an initial concentration of 128 μg/mL. Further 1:2 serial dilutions were performed. On a 96-well cell culture plate, each row was added with 100 μL of a corresponding drug solution in an order from a low concentration of 0.125 μg/mL to a high concentration of 128 μg/mL. In the meantime, sterile control (no drugs and bacteria were added and only the culture was added), growth control (DMSO was added in the culture broth of the well without adding the drug), and positive control group (vancomycin) were set. Each test and growth control well was inoculated with 5 μL of bacterial suspension (100 μL of bacterial solution at a concentration of $10^5$ CFU/mL). The 96-well cell culture plate was incubated at 37° C. for 16 h. The lowest concentration to inhibit bacterial growth completely was considered as the MIC value of the compound.

TABLE 1

Test results of In vitro antibacterial activities of the inventive compounds

| Compd. | MIC (μg/mL) | |
|---|---|---|
| | Newman | Mu50 |
| Vanco. | 2 | 8 |
| Tela. | <0.0625 | 1 |
| Van001 | 1 | 2 |
| Van002 | 0.5 | 2 |
| Van003 | 4 | 16 |
| Van004 | 1 | 4 |
| Van005 | 1 | 4 |
| Van006 | 8 | 32 |
| Van007 | 4 | 8 |
| Van008 | ≤0.0625 | 0.25 |
| Van009 | 0.5 | 1 |
| Van010 | 0.25 | 1 |
| Van011 | ≤0.0625 | 1 |
| Van012 | 0.5 | 0.5 |
| Van013 | 2 | 4 |
| Van014 | 0.25 | 0.125 |
| Van015 | 0.25 | 0.5 |
| Van016 | ≤0.0625 | 0.25 |

TABLE 1-continued

Test results of In vitro antibacterial activities of the inventive compounds

| Compd. | MIC (μg/mL) | |
|---|---|---|
| | Newman | Mu50 |
| Van017 | 0.5 | 1 |
| Van018 | 4 | 8 |
| Van019 | 0.5 | 2 |
| Van020 | 1 | 1 |
| Van021 | 2 | 4 |
| Van022 | 1 | 2 |
| Van023 | 2 | 4 |
| Van024 | 0.125 | 0.5 |
| Van025 | 16 | 32 |
| Van026 | 32 | 64 |
| Van027 | 1 | 4 |
| Van028 | 1 | 2 |
| Van029 | 4 | 8 |
| Van030 | 1 | 2 |
| Van031 | 0.125 | 0.5 |
| Van032 | ≤0.0625 | ≤0.0625 |
| Van033 | 0.5 | 2 |
| Van034 | ≤0.0625 | 0.25 |
| Van035 | 2 | 8 |
| Van036 | 0.25 | 0.5 |
| Van037 | ≤0.0625 | 0.25 |
| Van038 | ≤0.0625 | 0.125 |

The above in vitro antibacterial activity studies showed that most of the vancomycin analogues of the present invention represented by the examples have more active antibacterial activities against vancomycin-resistant Staphylococcus aureus than vancomycin. The antibacterial activity of some preferred compounds was 10-100 times higher than vancomycin, and 4-10 times higher than telavancin that was marketed in 2009. Antibacterial experiments show that the modification strategies for the novel vancomycin analogs involved in the present invention can significantly enhance antibacterial activity.

Biological Test Example 2 In Vivo Antibacterial Assay in Mice

Van016, Van032, Van037, Van038 of the present invention, vancomycin and telavancin were dissolved in sterile re-distilled water (ddH$_2$O) to prepare a solution in which the concentration of each compound was about 2 mg/mL.

SPF female BALB/c mice were purchased from the Shanghai Lab. Animal Research Center and housed under environment free of specific microorganisms. Overnight cultured Staphylococcus aureus USA300 LAC strain (Community-acquired methicillin-resistant Staphylococcus aureus (CA-MRSA)) was transferred into a fresh tryptic soy broth (TSB) medium at 1:100, and further cultivated for 3 h to reach the exponential growth phase. The collected strains were washed twice with sterile PBS buffer and suspended in the same buffer.

105 BALB/c mice were randomly divided into 7 groups, namely, negative control group, Van016 group, Van032 group, Van037 group, Van038 group, vancomycin group and telavancin group, with 15 mice in each experimental group, and each mice weighed approximately 18 grams.

Six to eight week old female BALB/c mice were anesthetized with pentobarbital sodium (80 mg/kg, intraperitoneally), and infected by retro-orbital injection with a suspension of 2.35×10$^8$ colony-forming units (CFUs) of USA300 LAC. One hour after infection, the mice in the six groups other than the negative control group were administered intraperitoneally with a single dose of 7 mg/kg of the selected compounds and the positive control compounds, respectively. At the same time, mice in the negative control group were injected with the same amount of sterile ddH$_2$O. The numbers of dead mice were recorded for the next 10 consecutive days, and the survival percentage of mice was calculated. The results were shown in FIG. 1.

As shown in FIG. 1, after 10 days, the survival rate of the Van038 group was 93.3%, the survival rate of the Van037 group was 86.6%, the survival rate of the Van032 group was 73.3%, and the survival rate of the Van016 group was 60.0%. In the positive control groups, the survival rate of the telavancin group was 93.3% while that of the vancomycin group was 6.6%. All the mice in the negative control group died after 6 days, and the survival rate was 0%.

in the 6 groups of mice at different times. The pharmacokinetic software WinNonlin 6.4 was used to obtain the corresponding half-life ($T_{1/2}$), the area under the drug concentration-time curve (AUC), the plasma clearance rate (CL), the mean residence time (MRT), and the volume of distribution calculated when the drug reaches steady state in vivo ($V_{SS}$). The specific results are shown in Table 2 below.

From the results of Table 2, it can be seen that the four compounds of the present invention showed a half-life ($T_{1/2}$) longer than vancomycin and telavancin, and an area under the drug concentration-time curve (AUC) 10-20 times larger than vancomycin and comparable to telavancin. In terms of plasma clearance (CL), all of the four compounds showed clearance rates slower than vancomycin and comparable to telavancin, and thus have good druggability parameters superior to the positive compound.

TABLE 2

In vivo pharmacokinetic test results in mice of representative compounds of the invention

| Compd. | $T_{1/2}$ (h) | AUC$_{last}$ (h*ng/mL) | AUC$_{INF\_obs}$ (h*ng/mL) | CL$_{\_obs}$ (mL/min/kg) | MRT$_{INF\_obs}$ (h) | V$_{SS\_obs}$ (mL/kg) |
|---|---|---|---|---|---|---|
| Van016 | 3.72 ± 0.70 | 10666 ± 2063 | 13450 ± 12725 | 6.4 ± 1.39 | 4.79 ± 0.24 | 1826 ± 334 |
| Van032 | 3.45 ± 1.26 | 20105 ± 1714 | 24345 ± 2804 | 3.45 ± 0.40 | 4.41 ± 1.23 | 900 ± 180 |
| Van037 | 2.94 ± 1.39 | 16631 ± 4960 | 20047 ± 5489 | 4.42 ± 1.42 | 4.21 ± 2.08 | 1077 ± 449 |
| Van038 | 3.81 ± 0.31 | 12112 ± 2483 | 12238 ± 2486 | 7.0 ± 1.38 | 4.18 ± 0.34 | 1754 ± 380 |
| Vanco. | 0.597 ± 0.208 | 1242 ± 335 | 1271 ± 347 | 68.7 ± 18 | 0.790 ± 0.26 | 3076 ± 175 |
| Tela. | 1.13 ± 0.13 | 17143 ± 5611 | 17304 ± 5745 | 5.1 ± 1.5 | 1.71 ± 0.13 | 520 ± 121 |

Note:
AUC$_{last}$: area under the drug concentration-time curve of the measured time period;
AUC$_{INF\_obs}$: measured value of the area under the drug concentration-time curve of the theoretical full time period;
CL$_{\_obs}$: measured value of the plasma clearance;
MRT$_{INF\_obs}$: measured value of the mean retention time of the theoretical full time period;
VSS$_{\_obs}$: measured value of the volume of drug distribution at steady-state.
The subscript of obs is an abbreviation of observed, indicating the measured value observed. The subscript of INF is an abbreviation of infinity, and refers to the infinite time range, that is, the theoretical full time period. The subscript of last refers to the time range from the start point to the end point of the measured time, that is, the measured time period.

The above in vivo pharmacodynamic studies showed that all of the said four vancomycin analogs of the present invention showed antibacterial activity against methicillin-resistant *Staphylococcus aureus* higher than vancomycin, indicating that Van016, Van032, Van037, Van038 have obvious protective effects on Methicillin-resistant *Staphylococcus aureus* and have better activity than vancomycin. Among these compounds, Van038 and Van037 achieved comparable activities with telavancin.

Biological Test Example 3 In Vivo Pharmacokinetic Assay in Mice

Van016, Van032, Van037, Van038 prepared by the present invention and the positive compounds vancomycin and telavancin were selected to perform the in vivo pharmacokinetic assay in mice. CD-1 mice used in this assay were purchased from Shanghai Lingchang Biotechnology co., LTD, and grown to 18-22 g at 18-29° C. and a relative humidity of 30-70%.

Eighteen male CD-1 normal mice were randomly divided into 6 groups, namely, Van016 group, Van032 group, Van037 group, Van038 group, vancomycin group and telavancin group, with 3 in each group. The mice in each group were injected intravenously a single dose of 5 mg/kg with the corresponding compound solutions prepared in Biological Test Example 2. Blood samples were collected (from the femoral vein) at 0.05 h, 0.25 h, 0.75 h, 2 h, 4 h, 8 h, 24 h, 7 time points in total, after the injection. LC-MS/MS was used to detect the plasma concentration (ng/mL) of the drug Biological Test Example 4 Liver and Kidney Cytotoxicity Assays Van011, Van037, vancomycin and telavancin were used to perform the liver and kidney cytotoxicity experiments. Liver and kidney cell viability assays were performed using the Cell Activity Assay Kit CCK8 (Cell Counting Kit-8) method.

Figure 2:
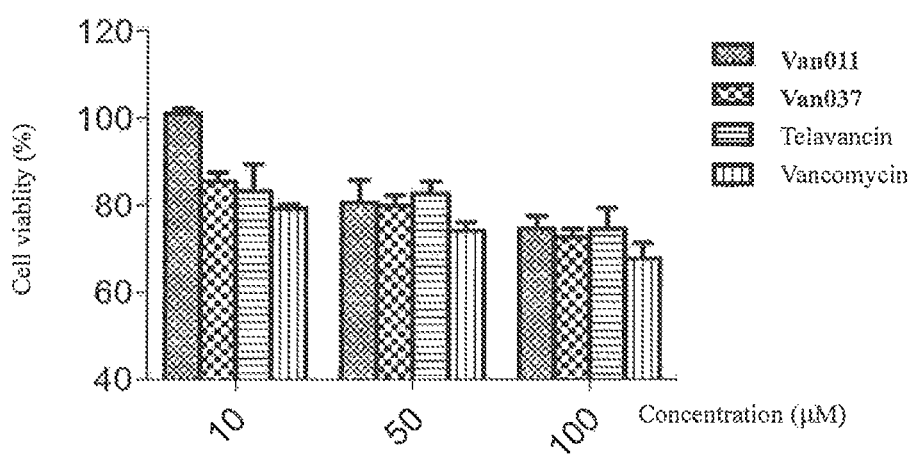
FIG. 2 shows the results of toxicity tests of Van011 and Van037 as well as vancomycin and telavancin in the HK-2 cell line model.
Figure 3:
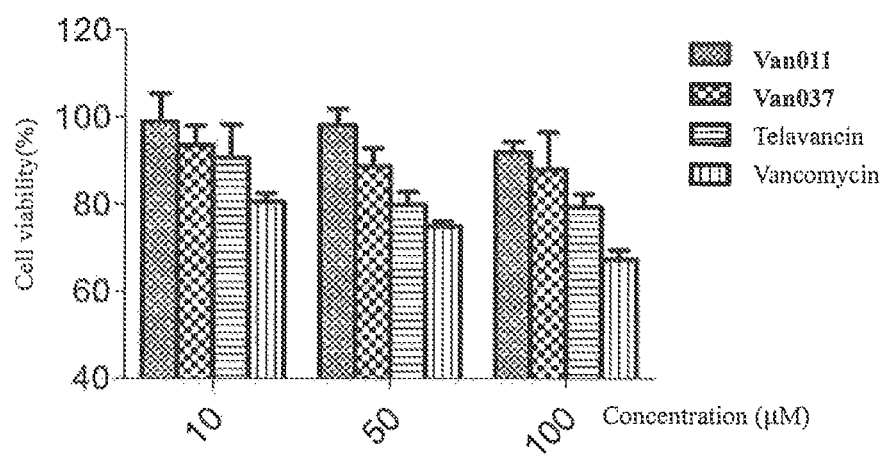
FIG. 3 shows the results of toxicity tests of Van011 and Van037 as well as vancomycin and telavancin in the HL-7702 cell line model.

HK-2 cells (human renal proximal tubular epithelial cells) and HL-7702 cells (human liver cells) in logarithmic growth phase were inoculated to a 96-well culture plate at a suitable density (about 5000 cells), at 100 μL per well. After overnight incubation, different concentrations (10 μM, 50 μM, 100 μM) of vancomycin, telavancin, Van011 or Van037 were added to treat for 72 h. Three replicate wells were set for each concentration, and the physiological saline vehicle control well corresponding to each concentration and a well for cell-free zero-adjustment were set. After the treatment, 10 μL of CCK8 detection solution was added into each well, the incubation was performed at 37° C. for about 1.5 h. The optical density (OD value) at 450 nm was measured on a VERSMax microplate reader. The OD value was converted to cell viability value according to the following equation:

Cell viability value=OD$_C$/OD$_{C=0}$×100, wherein, OD$_C$ represents the optical density obtained by different concentrations of the compounds to be tested, C represents the concentration of the compound, and OD$_{C=0}$ represents the optical density obtained without addition of the compound to be tested. And the results were shown in FIGS. 2 and 3.

The results showed that Van011 and Van037 of the present invention have less toxicity in liver cells than vancomycin and telavancin, and thus have better safety, while in kidney cells, they have toxicity less than vancomycin and comparable to telavancin.

The above is only a schematic description of the present invention, and those skilled in the art should understand that various modifications can be made to the present invention without departing from the working principle of the present invention, and thus fall in the protective scope of the present invention.

The invention claimed is:

1. A vancomycin derivative represented by the following Formula I-A or a pharmaceutically acceptable salt thereof:

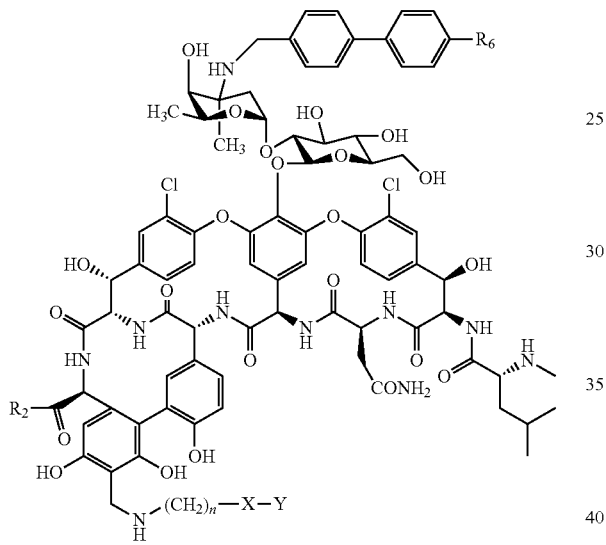

wherein, $R_6$ is selected from the group consisting of chlorine and trifluoromethyl, $R_2$ is selected from the group consisting of OH or the following groups:

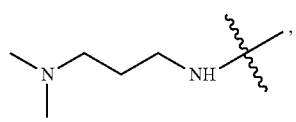

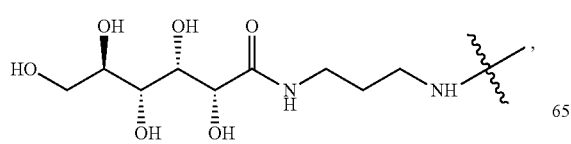

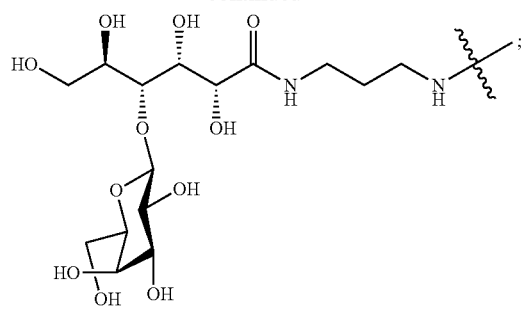

n is 2 or 3;

X is —O—, —NH—, —NHC(O)— or —$(CH_2)_q$—, wherein q is an integer between 0 and 2;

Y is a selected from the group consisting of:

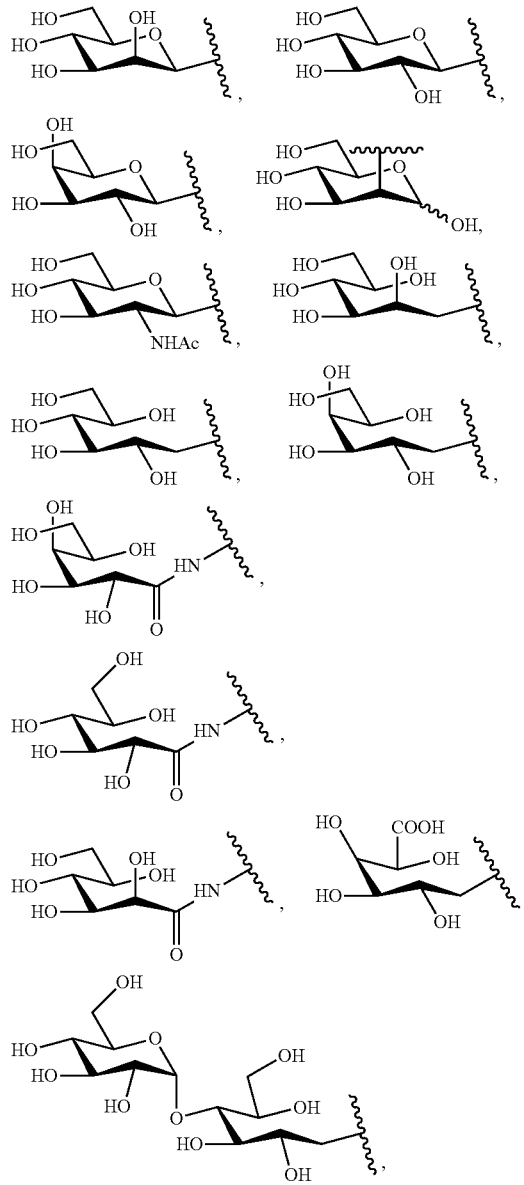

-continued

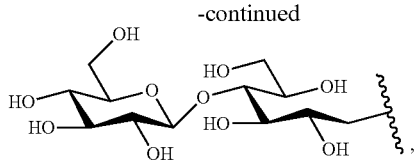,

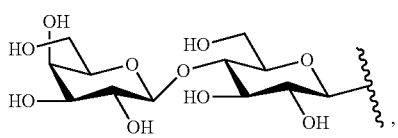,

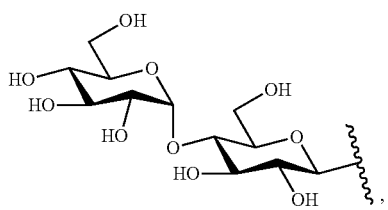,

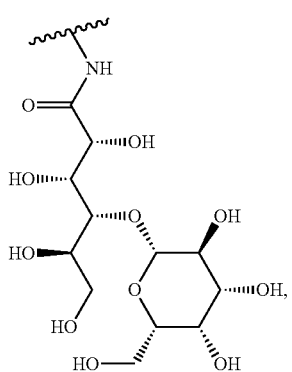,

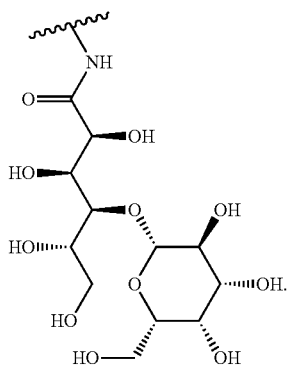.

2. A vancomycin derivative represented by the following Formula I-A or pharmaceutically acceptable salt thereof,

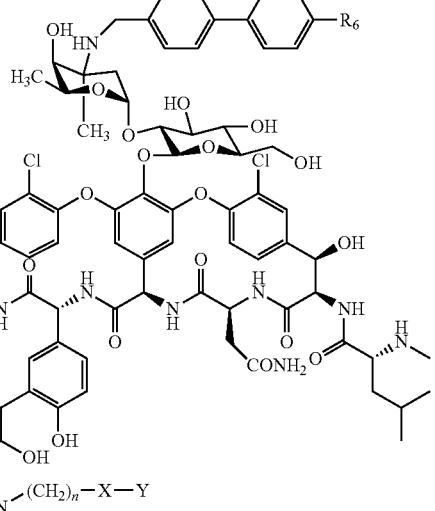

wherein, $R_6$ is selected from the group consisting of chlorine and trifluoromethyl, $R_2$ is selected from the group consisting of OH or the following groups:

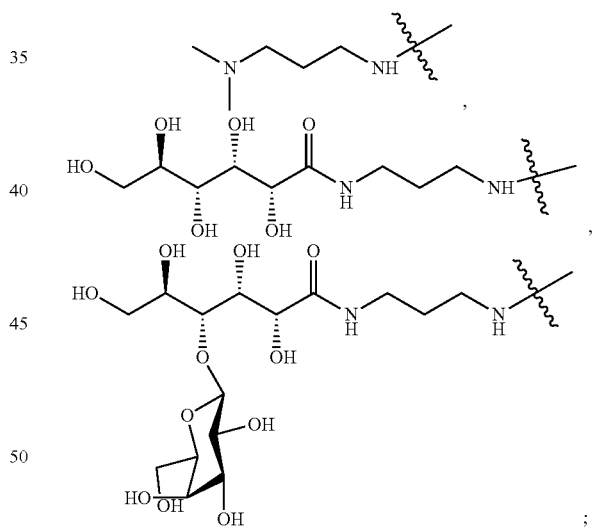;

n is 2 or 3;

X is —O—, —NH—, —NHC(O)— or —(CH$_2$)$_q$—, wherein q is an integer between 0 and 2;

Y is selected from the group consisting of:

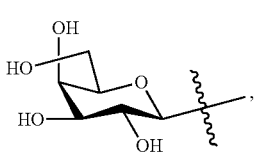,

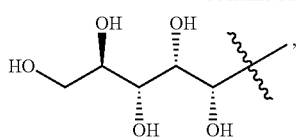

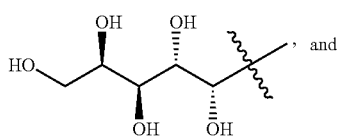

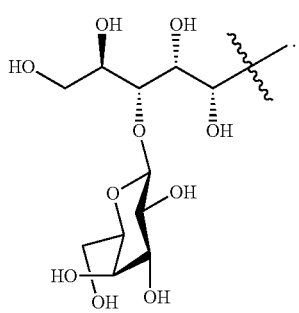

3. A vancomycin derivative or pharmaceutically acceptable salt thereof, wherein the compound is selected from the group consisting of:

| No. | Structure |
|---|---|
| Van016 | 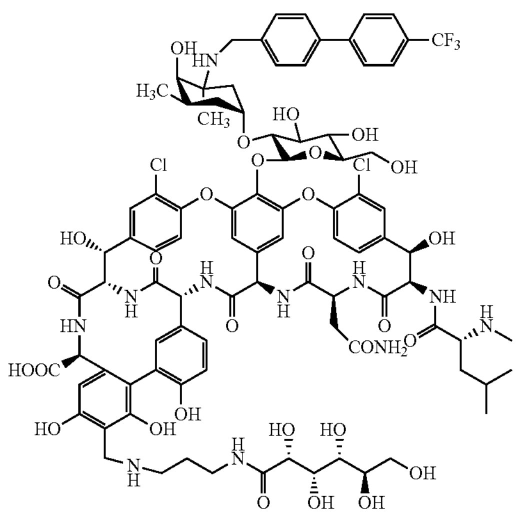 |
| Van037 | |

4. A pharmaceutical composition comprising a therapeutically effective amount of one or more selected from the group consisting of the vancomycin derivative and pharmaceutically acceptable salt thereof according to any one of claims 1, 2 and 3 as an active ingredient, and optionally, a pharmaceutically acceptable carrier, excipient, adjuvant, accessory, and/or diluent, and the said pharmaceutical composition may further comprise other pharmaceutically acceptable therapeutic agents.

5. A method for treatment and/or prevention of a bacterial infectious disease, comprising:
administering to a subject in need of such treatment an effective amount of the vancomycin derivative or pharmaceutically acceptable salt thereof according to claim 1.

6. The method according to claim 5, wherein the bacterial infectious disease is caused by a Gram-positive bacterium.

7. The method according to claim 6, wherein the Gram-positive bacterium is selected from the group consisting of *Staphylococcus, streptococcus, enterococcus, pneumococcus, Bacillus, Bacillus anthracis, Bacillus diphtherias, tetanus, Clostridium difficile,* and *Listeria monocytogenes.*

8. A method for treatment and/or prevention of a bacterial infectious disease, comprising: administering to a subject in need of such treatment an effective amount of the pharmaceutical composition according to claim 4.

9. The method according to claim 8, wherein the bacterial infectious disease is caused by a Gram-positive bacterium.

10. The method according to claim 9, wherein the Gram-positive bacterium is selected from the group consisting of *Staphylococcus, streptococcus, enterococcus, pneumococcus, Bacillus, Bacillus anthracis, Bacillus diphtherias, tetanus, Clostridium difficile,* and *Listeria monocytogenes.*

\* \* \* \* \*